(12) United States Patent
Heinz et al.

(10) Patent No.: US 12,297,489 B2
(45) Date of Patent: May 13, 2025

(54) METHOD FOR DETERMINING AT LEAST ONE QUALITY PARAMETER OF AN RNA SAMPLE

(71) Applicant: CureVac Manufacturing GmbH, Tübingen (DE)

(72) Inventors: Stefan Heinz, Heidelberg (DE); Tilmann Roos, Kusterdingen (DE)

(73) Assignee: CureVac Manufacturing GmbH, Tübingen (DE)

( * ) Notice: Subject to any disclaimer, the term of this patent is extended or adjusted under 35 U.S.C. 154(b) by 839 days.

(21) Appl. No.: 16/614,127

(22) PCT Filed: May 17, 2018

(86) PCT No.: PCT/EP2018/062998
§ 371 (c)(1),
(2) Date: Nov. 15, 2019

(87) PCT Pub. No.: WO2018/211038
PCT Pub. Date: Nov. 22, 2018

(65) Prior Publication Data
US 2023/0064106 A1  Mar. 2, 2023

(30) Foreign Application Priority Data

May 17, 2017 (WO) ................ PCT/EP2017/061859

(51) Int. Cl.
*C12Q 1/68* (2018.01)
*C12Q 1/6848* (2018.01)
*C12Q 1/6851* (2018.01)

(52) U.S. Cl.
CPC ......... *C12Q 1/6848* (2013.01); *C12Q 1/6851* (2013.01); *C12Q 2600/166* (2013.01)

(58) Field of Classification Search
CPC ............... C12Q 1/6848; C12Q 1/6851; C12Q 2600/166; C12Q 1/686
See application file for complete search history.

(56) References Cited

U.S. PATENT DOCUMENTS

| | | |
|---|---|---|
| 2005/0032730 A1 | 2/2005 | von der Mülbe et al. |
| 2005/0059624 A1 | 3/2005 | Hoerr et al. |
| 2005/0250723 A1 | 11/2005 | Hoerr et al. |
| 2006/0188490 A1 | 8/2006 | Hoerr et al. |
| 2008/0025944 A1 | 1/2008 | Hoerr et al. |
| 2008/0267873 A1 | 10/2008 | Hoerr et al. |
| 2009/0324584 A1 | 12/2009 | Hoerr et al. |
| 2010/0048883 A1 | 2/2010 | Ketterer et al. |
| 2010/0189729 A1 | 7/2010 | Hoerr et al. |
| 2010/0203076 A1 | 8/2010 | Fotin-Mleczek et al. |
| 2010/0291156 A1 | 11/2010 | Barner et al. |
| 2010/0305196 A1 | 12/2010 | Probst et al. |
| 2011/0053829 A1 | 3/2011 | Baumhof et al. |
| 2011/0250225 A1 | 10/2011 | Fotin-Mleczek et al. |
| 2012/0021043 A1 | 1/2012 | Kramps et al. |
| 2012/0258046 A1 | 10/2012 | Mutzke |
| 2013/0129754 A1 | 5/2013 | Thess et al. |
| 2013/0142818 A1 | 6/2013 | Baumhof et al. |
| 2013/0259879 A1 | 10/2013 | Baumhof et al. |
| 2013/0280283 A1 | 10/2013 | Lorenz et al. |
| 2013/0295043 A1 | 11/2013 | Kallen et al. |
| 2013/0336998 A1 | 12/2013 | Kallen et al. |
| 2015/0037326 A1 | 2/2015 | Butler-Ransohoff et al. |
| 2015/0050302 A1 | 2/2015 | Thess |
| 2015/0057340 A1 | 2/2015 | Thess et al. |
| 2015/0093413 A1 | 4/2015 | Thess et al. |
| 2015/0118183 A1 | 4/2015 | Baumhof |
| 2015/0118264 A1 | 4/2015 | Baumhof et al. |
| 2015/0165006 A1 | 6/2015 | Thess et al. |
| 2015/0184195 A1 | 7/2015 | Thess et al. |
| 2015/0218554 A1 | 8/2015 | Thess |
| 2015/0306249 A1 | 10/2015 | Baumhof et al. |
| 2015/0320847 A1 | 11/2015 | Thess et al. |
| 2016/0130345 A1 | 5/2016 | Fotin-Mleczek et al. |
| 2016/0166668 A1 | 6/2016 | Kallen et al. |
| 2016/0166678 A1 | 6/2016 | Kallen et al. |
| 2016/0166710 A1 | 6/2016 | Baumhof |
| 2016/0166711 A1 | 6/2016 | Schnee et al. |
| 2016/0168207 A1 | 6/2016 | Kramps et al. |
| 2016/0168227 A1 | 6/2016 | Kallen et al. |
| 2016/0235864 A1 | 8/2016 | Schlake et al. |
| 2016/0304883 A1 | 10/2016 | Grund et al. |

(Continued)

FOREIGN PATENT DOCUMENTS

| | | | |
|---|---|---|---|
| WO | WO 2016/180430 | 11/2016 | |
| WO | WO-2016180430 A1 * | 11/2016 | ......... C12N 15/1003 |

(Continued)

OTHER PUBLICATIONS

Rajeevan et al. (Methods, 2001, 25:443-451) (Year: 2001).*
Kiselinova et al. (PLoS One, 2014, 9(1):e85999, p. 1-8) (Year: 2014).*
Bustin et al., "Quantitative real-time RT-PCR—a perspective," *Journal of Molecular Endocrinology*, 34(3):597-601, 2005.
Chaudhari et al., "A review on good manufacturing practice (GMP) for medicinal products," *The Pharmatutor Magazine*, 2(9):8-19, 2014.
Devonshire et al., "Application of next generation qPCR and sequencing platforms to mRNA biomarker analysis," *Methods*, 59(1):89-100, 2013.
Loomis et al., "Strategies for modulating innate immune activation and protein production of in vitro transcribed mRNAs," *Journal of Materials Chemistry B*, 4(9):1619-1632, 2015.

(Continued)

*Primary Examiner* — Stephanie K Mummert
(74) *Attorney, Agent, or Firm* — Parker Highlander PLLC

(57) ABSTRACT

The present invention relates to a method for quality control analysis of an RNA sample comprising n different RNA molecule species using reverse transcription and a polymerase chain reaction (PCR) based assay, dPCR, preferably ddPCR, thereby determining at least one quality parameter. Moreover, the RNA molecules in the RNA sample may be in complexed form. In particular, the method is suitable for use in quality control during or following production of RNA samples for pharmaceutical use.

34 Claims, 10 Drawing Sheets

Specification includes a Sequence Listing.

(56) References Cited

U.S. PATENT DOCUMENTS

| | | |
|---|---|---|
| 2016/0304938 A1 | 10/2016 | Wochner |
| 2016/0326575 A1 | 11/2016 | von der Mülbe et al. |
| 2016/0331844 A1 | 11/2016 | Fotin-Mleczek et al. |
| 2017/0014496 A1 | 1/2017 | Fotin-Mleczek et al. |
| 2017/0029847 A1 | 2/2017 | Thess |
| 2017/0114378 A1 | 4/2017 | Wochner et al. |
| 2017/0252430 A1 | 9/2017 | Fotin-Mleczek et al. |
| 2017/0326225 A1 | 11/2017 | Rauch et al. |
| 2018/0044687 A1 | 2/2018 | Thess et al. |
| 2018/0080021 A1* | 3/2018 | Reuter ............ C12Q 1/6869 |
| 2018/0125952 A1 | 5/2018 | Fotin-Mleczek et al. |
| 2018/0126003 A1 | 5/2018 | Hoerr |
| 2018/0142275 A1 | 5/2018 | Roos et al. |
| 2018/0147146 A1 | 5/2018 | Eber et al. |
| 2018/0148727 A1 | 5/2018 | Grund et al. |
| 2018/0201967 A1 | 7/2018 | Eber et al. |
| 2018/0208957 A1 | 7/2018 | Roos et al. |
| 2018/0214537 A1 | 8/2018 | Mutzke et al. |
| 2018/0237786 A1 | 8/2018 | Schlake et al. |
| 2018/0237817 A1 | 8/2018 | Roos et al. |
| 2018/0243219 A1 | 8/2018 | Ketterer et al. |
| 2018/0296663 A1 | 10/2018 | Hipp et al. |
| 2018/0298372 A1 | 10/2018 | Funkner et al. |
| 2018/0312545 A1 | 11/2018 | Baumhof et al. |
| 2018/0371392 A1 | 12/2018 | Mayer et al. |
| 2019/0010485 A1 | 1/2019 | Yazdan Panah et al. |
| 2019/0017100 A1 | 1/2019 | Wochner et al. |
| 2019/0024096 A1 | 1/2019 | Schmid et al. |
| 2019/0040378 A1 | 2/2019 | Fotin-Mleczek et al. |
| 2019/0049414 A1 | 2/2019 | Wochner et al. |
| 2019/0083602 A1 | 3/2019 | Roos et al. |
| 2019/0100784 A1 | 4/2019 | Eber et al. |
| 2019/0125857 A1 | 5/2019 | Rauch et al. |
| 2019/0133950 A1 | 5/2019 | Eber et al. |
| 2019/0160164 A1 | 5/2019 | Rauch et al. |
| 2019/0177714 A1 | 6/2019 | Kunze et al. |
| 2019/0185859 A1 | 6/2019 | Fotin-Mleczek et al. |
| 2019/0194760 A1 | 6/2019 | Koch et al. |
| 2019/0225971 A1 | 7/2019 | Williams |
| 2019/0241633 A1 | 8/2019 | Fotin-Mleczek et al. |
| 2019/0249219 A1 | 8/2019 | Reichert et al. |
| 2019/0336608 A1 | 11/2019 | Baumhof et al. |
| 2019/0336611 A1 | 11/2019 | Baumhof et al. |
| 2019/0343933 A1 | 11/2019 | Horscroft et al. |
| 2019/0343942 A1 | 11/2019 | Fotin-Mleczek et al. |
| 2019/0351044 A1 | 11/2019 | Jasny et al. |
| 2019/0351047 A1 | 11/2019 | Jasny et al. |
| 2019/0351048 A1 | 11/2019 | Rauch |
| 2019/0381180 A1 | 12/2019 | Baumhof et al. |
| 2020/0023076 A1 | 1/2020 | Fotin-Mleczek et al. |
| 2020/0085852 A1 | 3/2020 | Fotin-Mleczek |
| 2020/0085944 A1 | 3/2020 | Heidenreich et al. |
| 2020/0149026 A1 | 5/2020 | Horscroft et al. |
| 2020/0163878 A1 | 5/2020 | Baumhof et al. |
| 2020/0179526 A1 | 6/2020 | Baumhof et al. |
| 2020/0318097 A1 | 10/2020 | Funkner et al. |
| 2020/0392572 A1 | 12/2020 | Yazdan Panah et al. |
| 2021/0030864 A1 | 2/2021 | Petsch et al. |
| 2021/0069315 A1 | 3/2021 | Baumhof et al. |
| 2021/0162037 A1 | 6/2021 | Jasny et al. |
| 2021/0170017 A1 | 6/2021 | Lutz et al. |
| 2021/0180106 A1 | 6/2021 | Wochner et al. |
| 2021/0205434 A1 | 7/2021 | Petsch et al. |
| 2021/0260178 A1 | 8/2021 | Jasny et al. |
| 2021/0261897 A1 | 8/2021 | Yazdan Panah et al. |
| 2021/0361761 A1 | 11/2021 | Lutz et al. |
| 2021/0379181 A1 | 12/2021 | Rauch et al. |
| 2021/0403925 A1 | 12/2021 | Chevessier-Tünnesen et al. |
| 2022/0040281 A1 | 2/2022 | Schwendt et al. |
| 2022/0073962 A1 | 3/2022 | Schwenger et al. |
| 2022/0133908 A1 | 5/2022 | Rejman et al. |
| 2022/0144877 A1 | 5/2022 | Heinz et al. |
| 2022/0211838 A1 | 7/2022 | Oostvogels et al. |

FOREIGN PATENT DOCUMENTS

| | | |
|---|---|---|
| WO | WO 2018/211038 | 11/2018 |
| WO | WO 2019/077001 | 4/2019 |
| WO | WO 2020/123300 | 6/2020 |
| WO | WO 2020/254535 | 12/2020 |
| WO | WO 2021/028439 | 2/2021 |
| WO | WO 2021/123332 | 6/2021 |

OTHER PUBLICATIONS

PCT International Search Report and Written Opinion issued in International Application No. PCT/EP2018/062998, mailed Jun. 27, 2018.

Vallazza et al., "Recombinant messenger RNA technology and its application in cancer immunotherapy, transcript replacement therapies, pluripotent stem cell induction, and beyond," *Wiley Interdisciplinary Reviews: RNA*, 6(5):471-499, 2015.

* cited by examiner

METHOD FOR DETERMINING AT LEAST ONE QUALITY PARAMETER OF AN RNA SAMPLE

This application is a national phase application under 35 U.S.C. § 371 of International Application No. PCT/EP2018/062998, filed May 17, 2018, which claims benefit of International Application No. PCT/EP2017/061859, filed May 17, 2017, the entire contents of each of which are hereby incorporated by reference.

FIELD OF THE INVENTION

The present invention relates to a method for quality control analysis of an RNA sample comprising n different RNA molecule species, i.e. for an RNA mixture. The method is suitable for use in quality control of RNA molecule mixtures during or following production. The invention relates to a method for determining at least one quality parameter of an RNA sample by using reverse transcription and digital PCR, wherein the RNA sample comprises n different RNA molecule species, wherein each of the n different RNA molecule species comprises one or more coding RNA molecules of synthetic origin, and wherein n is an integer of at least 1 or at least 2. The method is particularly suitable for analyzing mixtures of encapsulated and/or complexed RNA molecule mixtures, in particular for liposome, PEGylated peptide-based polymer and nanoparticle-formulated RNA molecule mixtures.

BACKGROUND OF THE INVENTION

Ribonucleic acid (RNA) molecules represent an emerging class of drugs. RNA-based therapeutics may be used in immunotherapy, gene therapy and genetic vaccination, belonging to the most promising and quickly developing therapeutic fields of modern medicine. RNA-based therapeutics may provide highly specific and individual treatment options for the therapy of a large variety of diseases.

For certain medical treatments and applications, it is desired to apply a mixture of RNA species. Examples of such RNA mixture based treatments may include the application of polyvalent RNA mixtures that provide protection against several serotypes of a pathogen (e.g., hemagglutinin (HA) from multiple serotypes of Influenza A and B virus); RNA mixtures that provide different antigens from one pathogen (e.g., different antigens from Influenza, such as HA, nucleoprotein (NP), neuraminidase (NA) etc.); RNA mixtures that provide protection against several isoforms or variants of a cancer antigen (e.g., prostate specific antigen (PSA) in the context of prostate carcinoma); RNA mixtures that provide different epitopes of an antigen; RNA mixtures that contain a cancer specific and/or patient specific mixture of cancer antigens (expressed antigens or mutated antigens); RNA mixtures that encode a variety of antibodies (e.g., antibodies that are targeted against different epitopes of one or more proteins), or any other therapeutically active RNA mixture (e.g., encoding different isoforms of an enzyme for molecular therapy, different therapeutic proteins for treatment of an indication wherein several proteins have to be supplemented).

For certain medical indications, the RNA molecules in the RNA (mixture) sample may be present in complexed form, i.e. in the form of at least one RNA-carrier complex. The complexation or encapsulation of RNA in RNA-carrier complexes facilitates successful in vivo delivery. Complexing carrier compounds used in the art typically include various types of peptides, polymers, carbohydrates, cholesterol, polyethylene glycol (PEG), lipids, phospholipids, PEGylated lipids, cationic and polycationic compounds, and combinations thereof, as well as other carrier compounds, which may be assembled into RNA-carrier complexes (see e.g. Gao, X., K. S. Kim, et al. (2007), AAPS J 9(1): E92-104). WO 2011/026641 describes polymeric nanoparticles comprising nucleic acids that are formed from disulfide-linked polyethyleneglycol/peptide conjugates, said nanoparticles being suitable for the in vivo and in vitro transfection of nucleic acids into cells.

For RNA mixture based therapeutics it is required that the n different components (n different RNA molecule species, complexed or free) of the drug product can be characterized, in terms of presence, integrity, ratio and quantity (quality control parameter). Such quality controls may be implemented during or following the RNA sample production, and/or during or following complexation of the RNA sample and/or as a batch release quality control.

As RNA mixture-based therapeutics can be composed of multiple RNA species of highly similar size and sequence (e.g., polyvalent vaccines composed of multiple similar antigens) standard methods for quality control to discriminate between RNA species of similar size such as agarose gel electrophoresis or analytic HPLC are not suitable. Further problems arise for the characterization of RNA mixtures comprising RNA-carrier complexes. For the precise characterization of the complexed RNA molecules, quality control analysis of a single RNA-carrier complex or of a defined number of RNA-carrier complexes is required as standard methods known in the art are not suitable.

An ideal method for the quality control of RNA mixtures should be fast, robust, and cost effective allowing for the characterization of any or all of the quality control parameters selected from the group consisting of presence, quantity, and integrity of at least one RNA molecule species and ratio of at least two RNA molecule species within an RNA sample comprising n different RNA molecule species.

Hence, there is a need for a method for RNA quality control analysis in particular in terms of cost-efficiency, robustness and the ability of the methods to discriminate highly similar RNA species in RNA samples comprising n different RNA molecule species.

SUMMARY OF THE INVENTION

Provided herein is a method for the quality control analysis of RNA samples comprising n different RNA molecule species. The analysis includes the determination of at least one quality parameter, preferably selected from quantity of the one or more coding RNA molecules of at least two RNA molecule species, presence of the one or more coding RNA molecules of at least two RNA molecule species, integrity of the one or more coding RNA molecules of at least two RNA molecule species and quantitative ratio between the one or more coding RNA molecules of at least two RNA molecule species. The method of the invention for quality control analysis of an RNA sample comprising n different RNA molecule species comprises using reverse transcription and a polymerase chain reaction (PCR) based assay, wherein each of the n different RNA molecule species comprises one or more coding RNA molecules of synthetic origin, wherein n is an integer of at least 1 or at least 2, wherein the PCR based assay is digital PCR (dPCR), preferably droplet digital (ddPCR).

The method of the invention is particularly useful to determine at least one quality parameter of RNA samples comprising n different RNA molecule species, wherein at least one of the one or more coding RNA molecules of the n different RNA molecule species is present in complexed form with at least one carrier compound, i.e. to determine at least one quality parameter of an RNA sample comprising at least one RNA-carrier complex comprising at least two RNA molecules belonging to at least two RNA molecule species.

Accordingly, the present invention relates to a method for quality control analysis of an RNA sample comprising n different RNA molecule species using reverse transcription and a polymerase chain reaction (PCR) based assay, wherein each of the n different RNA molecule species comprises one or more coding RNA molecules of synthetic origin, wherein n is an integer of at least 1 or at least 2, thereby determining at least one quality parameter. The analysis may be independent of the target sequence of the at least one RNA molecule species.

To solve the above mentioned problems in the art, the invention provides a method for quality control analysis of an RNA sample comprising n different RNA molecule species using reverse transcription and a polymerase chain reaction (PCR) based assay, wherein each of the n different RNA molecule species comprises one or more coding RNA molecules of synthetic origin, wherein n is an integer of at least 1, thereby determining at least one quality parameter. The PCR based assay is digital PCR (dPCR), preferably droplet digital (ddPCR).

In a particularly preferred embodiment, the RNA sample is a pharmaceutical RNA sample and further comprises a pharmaceutically acceptable carrier.

The method according to the invention may comprise the following steps:
a) simultaneous reverse transcription of the one or more coding RNA molecules of at least one RNA molecule species of the n different RNA molecule species in a single reaction vessel, thereby providing a cDNA sample comprising at least one cDNA molecule species, wherein each cDNA molecule species corresponds to one of the at least one RNA molecule species,
b) subjecting the cDNA sample to the PCR based assay, and
c) determining the at least one quality parameter of the RNA sample.

In a particularly preferred embodiment, n is an integer of at least 2, or at least 3, or is an integer in the range of 1 to 200 or 2 to 200.

In an embodiment, step b) comprises a step of
b1) simultaneous analysis of all cDNA molecule species in a single reaction vessel, or,
b2) if n is at least two, simultaneous analysis of two or more cDNA molecule species in a single reaction vessel, or
b3) analysis of each cDNA molecule species in a separate reaction vessel.

Preferably, the PCR based assay employs a detectable label. Optionally, the detectable label is a fluorescent probe, preferably comprising an intercalating dye or a fluorophore-quencher system. In preferred embodiments, the detectable label is selected from the group consisting of fluorescein, ethidiumbromide, SYBR™ green I (2-{2-[(3-dimethyl-amino-propyl)-propylamino]-1-phenyl-1H-chinoline-4-ylidenmethyl}-3-methyl-benzothiazol-3-ium-cation), LCgreen®, SYTO® 9, EvaGreen®, Resolight®, Chromofy, BOXTO, and monomethine dyes.

The PCR based assay may employ a sequence specific detectable label.

Optionally, in step b1) for each cDNA molecule species a different detectable label is used, or in step b2) for each cDNA molecule species to be analyzed in a single reaction vessel a different detectable label is used. The quality parameter is preferably selected from the group consisting of quantity of the one or more coding RNA molecules of the at least one RNA molecule species, presence of the one or more coding RNA molecules of the at least one RNA molecule species, integrity of the one or more coding RNA molecules of the at least one RNA molecule species and quantitative ratio between the one or more coding RNA molecules of at least two RNA molecule species.

In a preferred embodiment, the one or more coding RNA molecules are obtained by an in vitro method which is optionally in vitro transcription or chemical RNA synthesis.

Optionally, prior to step a) the one or more coding RNA molecules are purified, optionally using a method selected from the group consisting of high-performance liquid chromatography (HPLC), tangential flow filtration, oligo d(T) purification, ion exchange chromatography, hydroxyapatite chromatography, core bead flow-through chromatography, and combinations thereof.

In an embodiment of the invention, the one or more coding RNA molecules of each RNA molecule species encode a different amino acid sequence. Preferably, the one or more coding RNA molecules of each of the n different RNA molecule species encode for one of n different peptides. Also preferably, the RNA sequences of the one or more coding RNA molecules of each of the n different RNA molecule species are at least 80% identical to each other.

The n different RNA molecule species are optionally selected from a group consisting of n different RNA molecule species encoding n different proteins or peptides derived from different serotypes or strains of a pathogen, n different RNA molecule species encoding n different antigens from one pathogen, n different RNA molecule species encoding n different antigens from different pathogens, n different RNA molecule species encoding n different isoforms or variants of an antigen, preferably a cancer antigen, n different RNA molecule species encoding n different epitopes of an antigen, n different RNA molecule species encoding n different cancer specific and/or patient specific cancer antigens, n different RNA molecule species encoding n different antibodies or antibody chains, n different RNA molecule species encoding n different proteins of one or more metabolic pathways, n different RNA molecule species encoding for n different isoforms of a protein for molecular therapy, n different RNA molecule species encoding for n different therapeutically active RNA molecule species, and combinations thereof.

In a preferred embodiment of the present invention, at least one of the one or more coding RNA molecules is present in complexed form with at least one carrier compound, thereby forming at least one RNA-carrier complex.

Preferably, the at least one RNA-carrier complex comprises more than one of the one or more coding RNA molecules and/or comprises one or more coding RNA molecules of different RNA molecule species. Also preferably, at least 80% of the one or more coding RNA molecules in the RNA sample are present in the form of at least one RNA-carrier complex.

The at least one carrier compound is optionally a member selected from the group consisting of peptides, polymers, carbohydrates, cholesterol, polyethylene glycol (PEG), lipids, phospholipids, PEGylated lipids, cationic and polycationic compounds, and combinations thereof. Preferably, the cationic or polycationic compound is selected from the group consisting of cationic and polycationic polymers, cationic and polycationic peptides and proteins, preferably protamine and oligofectamine, cationic and polycationic polysaccharides, cationic and polycationic lipids, and combinations thereof.

In a very preferred embodiment, the at least one RNA-carrier complex comprises a member selected from the group consisting of liposome, lipid nanoparticle (LNP), and PEGylated peptide-based polymer complex and mixtures thereof.

Optionally, the method further comprises prior to step a) a step of
d) contacting the RNA sample with salt to release RNA molecules which are bound to the surface of the RNA-carrier complex.

Optionally, the method further comprises prior to step a) and, if present, after step d) a step of
e) contacting the RNA sample with at least one ribonuclease (RNase) under conditions suitable for said at least one ribonuclease to degrade RNA molecules which are not present in complexed form, and/or
f) subjecting the RNA sample to a method selected from the group consisting of gel filtration chromatography, molecular weight cut-off filtration, ultracentrifugation, and combinations thereof, to remove RNA molecules which are not present in complexed form.

The RNase may be selected from the group consisting of RNase A, RNase T1, RNase I, and combinations thereof.

In one embodiment, the method further comprises after step e) and prior to step a) a step of ee) inactivating the ribonuclease.

Step ee) may employ one or more members selected from the group consisting of RNase inhibitors, uridine 2',3'-cyclic vanadate, 5'-diphosphoadenosine 3'-phophate, 5'-diphosphoadenosine 2'-phophate, diethyl pyrocarbonate, guanidinium thiocyanate, 2-mercaptoethanol, heavy metal ions, mononucleotides, e.g. 2'-GMP or 3'-GMP, guanilyl-2',5'-guanosine, SDS, and combinations thereof.

The method optionally further comprises prior to step a) and, if present, after any one of steps d), e), f), and/or ee) a step of
g) partitioning of the RNA-carrier complexes.

Optionally, partitioning is performed using a fluorescence activated cell sorting (FACS) based assay and/or using acoustic liquid handling. Preferably, the FACS based assay comprises contacting the RNA-carrier complexes with an antibody and/or a fluorescent probe.

If the RNA-carrier complexes comprise PEG, the FACS based assay preferably comprises contacting the RNA-carrier complexes with an anti-PEG antibody and/or a secondary antibody comprising a fluorescent probe.

The inventive method further preferably comprises prior to step a) and, if present, after any one of steps d), e), f), ee), and/or g) a step of
h) contacting the RNA sample with a detergent, heparin and/or salt to release the at least one of the one or more coding RNA molecules which is present in complexed form, and/or
i) capturing the released one or more coding RNA molecules.

DEFINITIONS

Figure 1:
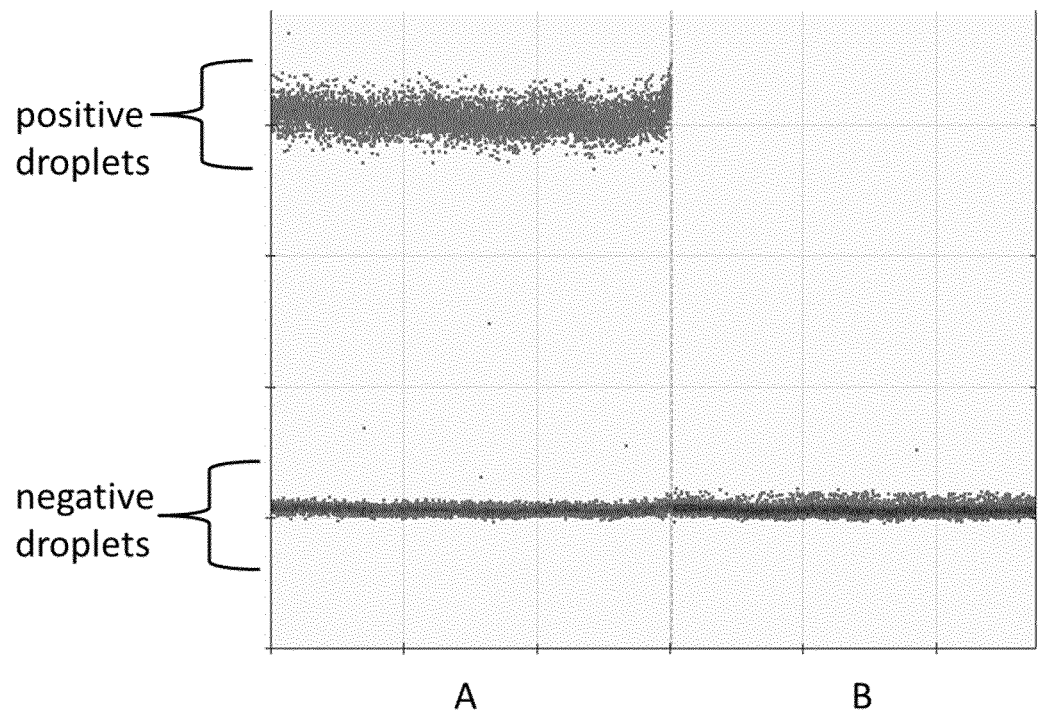
FIG. 1: ddPCR 1-D-plot of specificity testing of a primer combination detecting its target cDNA in a mixture of different cDNAs (left panel, A) vs. the same reaction in a cDNA mix without the target cDNA (right panel, B). The ratio of positive droplets detecting the target and negative droplets is then converted to target copies per µL reaction sample using Poisson's distribution algorithm. A detailed description of the experiment is provided in Example 2.

For the sake of clarity and readability, the following definitions are provided. Any technical feature mentioned for these definitions may be read on each and every embodiment of the invention. Additional definitions and explanations may be specifically provided in the context of these embodiments. Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization are those well-known and commonly employed in the art. Standard techniques are used for nucleic acid synthesis. The techniques and procedures are generally performed according to conventional methods in the art and various general references (e.g., Sambrook et al., 1989, Molecular Cloning: A Laboratory Manual, 2d ed. Cold Spring Harbor Laboratory Press, Cold Spring Harbor, NY), which are provided throughout this document.

RNA, mRNA: RNA is the usual abbreviation for ribonucleic acid. It is a nucleic acid molecule, i.e. a polymer consisting of nucleotide monomers. These nucleotides are usually adenosine-monophosphate (AMP), uridine-monophosphate (UMP), guanosine-monophosphate (GMP) and cytidine-monophosphate (CMP) monomers or analogs thereof, which are connected to each other along a so-called backbone. The backbone is formed by phosphodiester bonds between the sugar, i.e. ribose, of a first and a phosphate moiety of a second, adjacent monomer. The specific order of the monomers, i.e. the order of the bases linked to the sugar/phosphate-backbone, is called the RNA sequence. Usually RNA may be obtainable by transcription of a DNA sequence, e.g., inside a cell. In eukaryotic cells, transcription is typically performed inside the nucleus or the mitochondria. In vivo, transcription of DNA usually results in the so-called premature RNA which has to be processed into so-called messenger-RNA, usually abbreviated as mRNA. However, in the present invention, whenever the term "RNA" is used, it encompasses in particular "mRNA". Processing of the premature RNA, e.g. in eukaryotic organisms, comprises a variety of different posttranscriptional modifications such as splicing, 5'-capping, polyadenylation, export from the nucleus or the mitochondria and the like. The sum of these processes is also called maturation of RNA. The mature messenger RNA usually provides the nucleotide sequence that may be translated into an amino acid sequence of a particular peptide or protein. Typically, a mature mRNA comprises a 5'-cap, optionally a 5'UTR, a coding sequence, optionally a 3'UTR and a poly(A) sequence. If RNA molecules are of synthetic origin, the RNA molecules are meant not to be produced in vivo, i.e. inside a cell or purified from a cell, but in an in vitro method. Examples for suitable in vitro methods are in vitro transcription and chemical RNA synthesis.

In addition to messenger RNA, several non-coding types of RNA exist which may be involved in regulation of transcription and/or translation, and immunostimulation and which may also be produced by in vitro transcription. The term "RNA" further encompasses RNA molecules, such as viral RNA, retroviral RNA and replicon RNA, small interfering RNA (siRNA), antisense RNA, saRNA (small activating RNA), CRISPR RNA (small guide RNA, sgRNA), ribozymes, aptamers, riboswitches, immunostimulating RNA, transfer RNA (tRNA), ribosomal RNA (rRNA), small nuclear RNA (snRNA), small nucleolar RNA (snoRNA), microRNA (miRNA), and Piwi-interacting RNA (piRNA).

In vitro transcription: The term "in vitro transcription" or "RNA in vitro transcription" relates to a process wherein RNA is synthesized in a cell-free system (in vitro). In vitro transcription is thus one example for an in vitro method to obtain RNA molecules of synthetic origin. DNA, particularly plasmid DNA, is used as DNA template for the generation of RNA transcripts. RNA may be obtained by DNA-dependent in vitro transcription of an appropriate DNA template, which according to the present invention is preferably a linearized plasmid DNA template. The promoter for controlling in vitro transcription can be any promoter for any DNA-dependent RNA polymerase. Particular examples of DNA-dependent RNA polymerases are the T7, T3, and SP6 RNA polymerases. A DNA template for RNA in vitro transcription may be obtained by cloning of a nucleic acid, in particular cDNA corresponding to the respective RNA to be in vitro transcribed, and introducing it into an appropriate vector for in vitro transcription, for example into plasmid DNA. In a preferred embodiment of the present invention the DNA template is linearized with a suitable restriction enzyme, before it is transcribed in vitro. The cDNA may be obtained by reverse transcription of mRNA or chemical synthesis. Moreover, the DNA template for in vitro RNA synthesis may also be obtained by gene synthesis.

Methods for in vitro transcription are known in the art (Geall et al. (2013) Semin. Immunol. 25(2): 152-159; Brunelle et al. (2013) Methods Enzymol. 530:101-14). Reagents used in said method typically include:
1) a linearized DNA template with a promoter sequence that has a high binding affinity for its respective RNA polymerase such as bacteriophage-encoded RNA polymerases;
2) ribonucleoside triphosphates (NTPs) for the four bases (adenine, cytosine, guanine and uracil), optionally, the fraction of NTPs is optimized to the RNA sequence (according to WO 2015/188933);
3) optionally a cap analog as defined below (e.g. m7G (5')ppp(5')G (m7G));
4) a DNA-dependent RNA polymerase capable of binding to the promoter sequence within the linearized DNA template (e.g. T7, T3 or SP6 RNA polymerase);
5) optionally a ribonuclease (RNase) inhibitor to inactivate any contaminating RNase;
6) optionally a pyrophosphatase to degrade pyrophosphate, which may inhibit transcription;
7) $MgCl_2$, which supplies $Mg^{2+}$ ions as a co-factor for the polymerase;
8) a buffer to maintain a suitable pH value, which can also contain antioxidants (e.g. DTT), and/or polyamines such as spermidine at optimal concentrations.

Since the method of the invention is specifically directed to the analysis of RNA in a pharmaceutical sample, the RNA in said pharmaceutical sample preferably meets regulatory requirements necessary for the market approval of a medicinal product. Accordingly, the RNA is preferably a GMP-grade RNA (GMP=good manufacturing practice). GMP-grade RNA is produced using a manufacturing process approved by regulatory authorities, implementing various quality controls on DNA level and RNA level as described in detail in WO2016/180430A1.

In vitro transcribed RNA: An "in vitro transcribed RNA" or "RNA prepared by in vitro transcription" is an RNA molecule that has been synthesized from a DNA template, commonly a linearized and purified plasmid (template) DNA, a PCR product, or an oligonucleotide. Hence, the composition of the sample comprising in vitro transcribed RNA is determined by the DNA template which is subjected to in vitro transcription. If only one DNA template is present in the in vitro transcription reaction, the sample comprising in vitro transcribed RNA will only comprise one RNA species. If two or more different DNA templates are present in the in vitro transcription reaction, the sample comprising in vitro transcribed RNA will comprise two or more different RNA molecule species. The in vitro transcribed RNA is distinguished from the cellular RNA of an organism in that it comprises only a limited number of different RNA species, which number is determined by the number of the DNA template in the in vitro transcription reaction. "In vitro transcribed RNA" is to be understood as RNA or RNA molecules of synthetic origin according to the present invention.

RNA synthesis occurs in a cell free ("in vitro") assay catalyzed by DNA dependent RNA polymerases. Particular examples of DNA dependent RNA polymerases are the T7, T3, and SP6 RNA polymerases. An in vitro transcribed mRNA may comprise elements such as 5'-cap, optionally a 5'UTR, a coding sequence, optionally a 3'UTR and a poly (A) sequence. Aside from proteinogenic messenger RNA, several non-coding types of RNA exist which may be involved in regulation of transcription and/or translation. Such RNA molecules may also be synthesized by RNA in vitro transcription.

Template DNA: As used herein, the term "template DNA" (or "DNA template") typically relates to a DNA molecule comprising a nucleic acid sequence encoding the RNA sequence to be transcribed in vitro. The template DNA is used as template for RNA in vitro transcription in order to produce the RNA encoded by the template DNA. Therefore, the template DNA comprises all elements necessary for RNA in vitro transcription, particularly a promoter element for binding of a DNA dependent RNA polymerase as e.g. T3, T7 and SP6 RNA polymerases 5' of the DNA sequence encoding the target RNA sequence. Furthermore, the template DNA may comprise primer binding sites 5' and/or 3' of the DNA sequence encoding the target RNA sequence to determine the presence of the DNA sequence encoding the target RNA sequence e.g. by PCR or DNA sequencing. As used herein, the term 'template DNA' may also refer to a DNA vector, such as a plasmid DNA, which comprises a nucleic acid sequence encoding the RNA sequence. Further, the "template DNA" in the context of the present invention may be a linear or a circular DNA molecule.

RNA molecule species: The term "RNA molecule species" denotes at least one RNA molecule in a population of RNA molecules which do not differ in their RNA sequence and/or their sequence length. Hence, the RNA molecules within one RNA molecule species are encoded by the same template DNA. If the RNA present within the sample is a coding RNA, one RNA species may encode one target peptide or protein or variant thereof.

(n) different RNA molecule species: The term "(n) different RNA molecule species" denotes a group of (n) RNA molecules which may differ with respect to their RNA sequence and/or their sequence length. Hence, if an RNA sample comprises n different RNA molecule species and if n is 2, the RNA sample comprises RNA molecules which belong to either of the 2 RNA molecule species, i.e. have the same RNA sequence and/or their sequence length. In a typical RNA sample comprising 2 different RNA molecule species, the one or more RNA molecules of the first RNA molecule species do not differ in their RNA sequence and/or their sequence length among each other but differ from the RNA sequence and/or sequence length of the one or more RNA molecules of the second RNA molecule species. Each RNA molecule species comprises at least one RNA molecule, i.e. each RNA molecule species comprises one or more RNA molecules. Accordingly, if an RNA sample comprises n different RNA molecule species, the RNA sample comprises at least n RNA molecules (at least one RNA molecule per RNA molecule species). However, typically an RNA molecule species comprises a higher number of RNA molecules per RNA molecule species in one sample. In the present invention, the one or more RNA molecules of each RNA molecule species are coding RNA species of synthetic origin. If the RNA molecule species are coding RNA molecule species, each of the (n) different RNA molecule species preferably but not necessarily encodes one target peptide/protein or variant thereof. In a sample comprising (n) different RNA species which is analyzed by the method of the present invention, identical, similar or different amounts of each species may be present, preferably the amounts are identical or similar. The number of different RNA molecule species which are present in the RNA sample are reflected by the integer n which is at least 1 and thus can be 1, 2, 3, 4, 5, 6, 7, 8, 9, 10, 11, 12, 13, 14, 15, 16, 17, 18, 19, 20, 21 and so forth. Preferably, n is an integer of at least 2 or at least 3, or in the range of 1 to 200, or 2 to 200, more preferably of 2 to 150, even more preferably of 3 to 100, and most preferably of 4 to 50. A sample comprising n different RNA species may be prepared as described in PCT/EP2016/082487.

In the method of the present invention, the n different RNA molecule species may have a similar length, as the detection and discrimination of the n different RNA species is not dependent on differences in the length. For example, the length of the n different RNA species within the sample may differ by not more than 10% or 8%, preferably not more than 7% or 6%, more preferably by not more than 5% and most preferably by not more than 4%.

In particular, if the analysis is independent of the target sequence of the n different RNA molecule species, the RNA molecule species may have a similar target sequence. For example, the target sequences of the n different RNA molecule species within the sample or a part of these target sequences may have a sequence identity of at least 70% or 75%, of at least 80% or 85%, or of at least 90%, 95% or even 100%. The sequence identity may be over a region comprising 200 nucleotides, 300 nucleotides, 400 nucleotides, 500 nucleotides or 600 nucleotides or over the complete target sequence.

In the present invention, the RNA sequences of the one or more coding RNA molecules of each of the n different RNA molecule species may be at least 80% identical to each other, which considers the identity of the whole RNA molecule sequence and not only the target sequence.

Quality parameter: The method according to the present invention is suitable for determining at least one quality parameter. The term "quality parameter" comprises any parameter of the RNA sample which is related to a property of the RNA sample and typically obtained for quality control during or following production. Examples of quality parameters are quantity of the one or more coding RNA molecules of at least two RNA molecule species, presence of the one or more coding RNA molecules of at least two RNA molecule species, integrity of the one or more coding RNA molecules of at least two RNA molecule species and quantitative ratio between the one or more coding RNA molecules of at least two RNA molecule species. The quality parameter is useful to determine, e.g., whether an RNA sample comprises all required n different RNA molecule species, the quantitative ratio between at least two of the n different RNA molecule species, whether the RNA molecules of the n different RNA molecule species are present in intact form (integrity) and to determine the amount of each RNA molecule species in the RNA sample. By determining at least one quality control parameter, an RNA sample can be analyzed and rated according to regulatory requirements as necessary for marketing approval of a medicinal product. Since the method of the invention is specifically directed to the analysis of RNA samples comprising a mixture of n different RNA molecule species, the quality parameters are usually determined for at least two RNA molecule species.

Presence of the one or more coding RNA molecules of an or at least two RNA molecule species: In the analysis for presence of an RNA molecule species it is determined whether an RNA molecule with a specific nucleic acid sequence is present within an RNA sample prepared by an in vitro method, e.g. in vitro transcription or chemical RNA synthesis, to make sure that all species of the n different RNA molecule species are present in the RNA sample and to exclude those cases in which RNA molecule species were not produced, although the corresponding template DNA was subjected to an RNA in vitro transcription reaction or chemical RNA synthesis was performed and those cases in which the RNA is produced by in vitro transcription, but has errors within its sequence so that its sequence does not 100% correspond to the sequence of the template DNA.

Integrity of the one or more coding RNA molecules of an or at least two RNA molecule species: The term "integrity" describes whether the complete target RNA sequence is present in the sample of in vitro produced RNA. Low integrity could be due to, amongst others, degradation, cleavage, incorrect or incomplete chemical synthesis, incorrect base pairing, integration of modified nucleotides or the modification of already integrated nucleotides, lack of or incomplete capping, lack of or incomplete polyadenylation, or incomplete transcription. Within the method of the present invention the integrity of the RNA molecules of at least one RNA molecule species is determined by hybridizing at least two single-stranded nucleic acid molecules to different parts of the one or more RNA molecules of at least two RNA molecule species and detecting any double strands formed. Preferably one single-stranded nucleic acid molecule or set of primers binds to the 5' end of the RNA molecule of one RNA molecule species and another single-stranded nucleic acid molecule or set of primers binds to the 3' end of said RNA molecule of the same RNA molecule species.

Quantity of the one or more coding RNA molecules of an or at least two RNA molecule species: The quantity of the one or more coding RNA molecules of an RNA molecule species in an RNA sample is the number of copies of the RNA molecules belonging to said RNA molecule species present in said RNA sample.

Quantitative ratio between the one or more coding RNA molecules of at least two RNA molecule species: The quantitative ratio of the one or more coding RNA molecules of at least two RNA molecule species may be determined by determining the quantity of the one or more coding RNA molecules of at least two RNA molecule species and evaluating the quantitative ratio of both or more quantities. Since the method allows determining the quantity of the one or more coding RNA molecules of all RNA molecule species, it is possible to determine the quantitative ratio between all RNA molecule species.

Sequence of a nucleic acid molecule/nucleic acid sequence/Sequence of an RNA: The sequence of a nucleic acid molecule or sequence of an RNA molecule (species) is typically understood to be the particular and individual order, i.e. the succession of its nucleotides. Within the present invention the sequence of an RNA species within the sample comprises a target sequence and may additionally comprise sequences located 5' and/or 3' of the target sequence.

Target sequence, target sequence of an RNA species: In the broadest sense, the term "target sequence" describes any sequence element or sequence stretch of the one or more RNA molecules of the n different RNA molecule species (or the respective corresponding cDNA sequence) that is to be analyzed using the inventive PCR based method described herein. More specifically, in the context of the invention, "target sequence" is the sequence or part of the sequence of the RNA species which is intended to provide a specific biological effect e.g. when used as a medicament.

Examples of target sequences include the coding sequence of a peptide or protein (messenger RNA (mRNA)) or the sequence of viral RNA, retroviral RNA and replicon RNA, small interfering RNA (siRNA), antisense RNA, saRNA (small activating RNA), CRISPR RNA (small guide RNA, sgRNA), ribozymes, aptamers, riboswitches, immunostimulating RNA, transfer RNA (tRNA), ribosomal RNA (rRNA), small nuclear RNA (snRNA), small nucleolar RNA (snoRNA), microRNA (miRNA), and Piwi-interacting RNA (piRNA).

Coding sequence: The coding sequence of the one or more coding RNA molecules is the RNA sequence which is translated into a peptide or protein or variant thereof. It therefore comprises a start codon, a number of nucleotides encoding the amino acids of the peptide or protein or variant thereof which is produced and a stop codon. Due to the three-letter code the total number of nucleotides within the coding sequence can be divided by three. The coding sequence may be flanked by 5' and 3' untranslated regions (UTRs). The coding sequence of a peptide or protein or variant thereof may be identical to the sequence within the organism from which it is derived or it may be optimized for translation efficiency and/or stability of the RNA, for example by optimizing the GC content of the coding sequence.

5-untranslated region (5'-UTR): A 5'-UTR is typically understood to be a particular section of messenger RNA (mRNA). It is located 5' of the coding sequence of the mRNA. Typically, the 5'-UTR starts with the transcriptional start site and ends one nucleotide before the start codon of the coding sequence. The 5'-UTR may comprise elements for controlling gene expression, also called regulatory elements. Such regulatory elements may be, for example, ribosomal binding sites. The 5'-UTR may be post-transcriptionally modified, for example by addition of a 5' cap structure. In the context of the present invention, the term "5'-UTR" typically refers to the sequence of an mRNA, which is located between the 5' cap structure and the start codon. Preferably, the 5'-UTR is the sequence, which extends from a nucleotide located 3' to the 5' cap structure, preferably from the nucleotide located immediately 3' to the 5' cap structure, to a nucleotide located 5' to the start codon of the coding sequence, preferably to the nucleotide located immediately 5' to the start codon of the coding sequence.

3'-untranslated region (3'-UTR): Generally, the term "3'-UTR" refers to a part of the RNA molecule, which is located 3' (i.e. "downstream") of a coding sequence and which is not translated into protein. Typically, a 3'-UTR is the part of an mRNA which is located between the protein coding region (coding sequence (CDS)) and the 3' terminus of the mRNA. In the context of the invention, the term 3'-UTR may also comprise elements, which are not encoded in the template, from which an RNA is transcribed, but which are added after transcription during maturation, e.g. a poly(A) sequence (or poly(A) 'tail'). A 3'-UTR of the mRNA is not translated into an amino acid sequence. The 3'-UTR sequence is generally encoded by the DNA template, which is transcribed into the corresponding mRNA during the gene expression process. In the context of the present invention, a 3'-UTR corresponds to the sequence of a mature mRNA, which is located between the stop codon of the protein coding region, preferably immediately 3' to the stop codon of the protein coding region, and the poly(A) sequence of the mRNA.

Poly(A) sequence: A poly(A) sequence, also called poly (A) tail or 3'-poly(A) tail, is usually understood to be a sequence of adenine nucleotides, e.g., of up to about 400 adenosine nucleotides, e.g. from about 20 to about 400, preferably from about 50 to about 400, more preferably from about 50 to about 300, even more preferably from about 50 to about 250, most preferably from about 60 to about 250 adenosine nucleotides, which is preferably added to the 3'-terminus of an mRNA. A poly(A) sequence is typically located at the 3'-end of an RNA, in particular mRNA. A poly(A) sequence may be located within an (m)RNA or any other nucleic acid molecule, such as, e.g., in a vector, for example, in a vector serving as template for the generation of an RNA, preferably an mRNA, e.g., by transcription of the vector. Moreover, poly(A) sequences, or poly(A) tails may be generated by enzymatic polyadenylation of the RNA, e.g. by using Poly(A)polymerases (PAP) derived from e.g. E. coli or yeast. Polyadenylation of RNA can be achieved by using immobilized PAP enzymes e.g. in a polyadenylation reactor as described in WO 2016/174271. The term "poly(A) sequence" further comprises sequence elements, preferably artificial sequence elements, that are part of the 3'-UTR or located at the 3'-terminus of the artificial nucleic acid molecule, and which preferably comprise up to 1100 adenine nucleotides, more preferably at least 60, 70, 80, 90, 100, 110, 120, 130, 140, 150, 160, 170, 180, 190, 200, 210, 220, 230, 240, 250, 300, 350, 400, 500, 600, 700, 800, 900, or at least 1000 adenine nucleotides. In general, the poly(A) sequence consists of adenosine monophosphates.

Detectable label: A detectable label is a detectable compound which is attached directly or indirectly to another molecule. Within the method of the present invention the detectable label is attached to a single-stranded nucleic acid molecule. The skilled person knows methods for attaching labels to nucleic acid molecules. Specific, non-limiting examples of labels include fluorescent probes and fluorogenic moieties, chromogenic moieties, haptens, affinity tags and radioactive isotopes. The label can be detectable directly (e.g. optically) or indirectly (e.g. by interaction with one or more molecules which are in turn detectable). Within the method of the present invention preferably fluorescent probes are used. The method of detecting the double-stranded nucleic acid molecules produced in the PCR based assay of the invention depends on the detectable label attached to the nucleic acid probe. For example, if the nucleic acid probe is labeled with a radioactive isotope, the double-stranded nucleic acid molecules are detected by autoradiography. If the nucleic acid probe is labeled with a fluorescent probe, the double-stranded nucleic acid molecules are detected by fluorescence spectroscopy.

Complementary: Two nucleic acid sequences are complementary, if the bases forming a first nucleic acid sequence are able to form base pairs with the bases forming a second nucleic acid sequence by hydrogen bonds. Hydrogen bonds and therefore base pairs can be formed between a pyrimidine (i.e. cytosine, uracil, thymine and analogues thereof) and a purine (i.e. adenine, guanine and analogues thereof). In order to form a double strand two sequences do not need to be 100% complementary to each other. However, within the present invention the single-stranded nucleic acid molecules which serve as nucleic acid probes are preferably 100% complementary to the target sequence to enable a high level of quality control of the in vitro transcribed RNA.

Sequence identity: Two or more sequences are identical if they exhibit the same length and order of nucleotides or amino acids. The percentage of identity typically describes the extent, to which two sequences are identical, i.e. it typically describes the percentage of nucleotides that correspond in their sequence position to identical nucleotides of a reference sequence. For the determination of the degree of identity, the sequences to be compared are considered to exhibit the same length, i.e. the length of the longest sequence of the sequences to be compared. This means that a first sequence consisting of 8 nucleotides/amino acids is 80% identical to a second sequence consisting of 10 nucleotides/amino acids comprising the first sequence. In other words, in the context of the present invention, identity of sequences preferably relates to the percentage of nucleotides/amino acids of a sequence, which have the same position in two or more sequences having the same length. Gaps are usually regarded as non-identical positions, irrespective of their actual position in an alignment. The sequence identity may be determined using a series of programs, which are based on various algorithms, such as BLASTN, ScanProsite, the laser gene software, etc. As an alternative, the BLAST program package of the National Center for Biotechnology Information may be used with the default parameters. In addition, the program Sequencher (Gene Codes Corp., Ann Arbor, MI, USA) using the "dirtydata"-algorithm for sequence comparisons may be employed. The identity between two amino acid or nucleic acid sequences is defined as the identity calculated with the program needle in the version available in April 2011. Needle is part of the freely available program package EMBOSS, which can be downloaded from the corresponding website. The standard parameters used are: gapopen 10.0 ("gap open penalty"), gapextend 0.5 ("gap extension penalty"), datafile EONAFULL (matrix) in the case of nucleic acids.

Standard/reference curve: A standard curve or reference curve is a type of graph used for determining quantities of an analyte, e.g. in qPCR. It is established by measuring multiple samples with known concentration (i.e. the standards) and plotting these concentrations against the measured values, such as radioactivity or fluorescence.

Reverse transcription: Reverse transcription is the process of generating complementary DNA (cDNA) from RNA. In this process an RNA, i.e. one or more coding RNA molecules of at least two RNA molecule species of the n different RNA molecule species, is incubated with the enzyme reverse transcriptase, deoxynucleotides (dNTPs), and at least one suitable primer for a time and under conditions sufficient for cDNA synthesis to occur, e.g. incubation for thirty minutes to one hour at a temperature of about 37° C. to 42° C. The primer(s) used for reverse transcription may be random so that any RNA molecule, e.g. one or more coding RNA molecules of all n different RNA molecule species, present in a sample may be reverse transcribed into cDNA or may be target-specific so that only the target RNA, e.g. one or more coding RNA molecules of at least two RNA molecule species of the n different RNA molecule species, are reverse transcribed into the corresponding cDNA.

Polymerase chain reaction (PCR): The polymerase chain reaction (PCR) is a technology in molecular biology used to amplify a piece of DNA across several orders of magnitude, generating thousands to millions of copies of a particular DNA sequence. The method relies on thermal cycling, consisting of cycles of repeated heating and cooling of the reaction for DNA melting and enzymatic replication of the DNA. Primers (short DNA fragments) containing sequences complementary to the target sequence along with a heat-stable DNA polymerase, such as Taq polymerase, enable selective and repeated amplification. As PCR progresses, the DNA generated is itself used as a template for replication, setting in motion a chain reaction in which the DNA template is exponentially amplified. The DNA polymerase enzymatically assembles a new DNA strand from DNA building-blocks, the nucleotides, by using single-stranded DNA as a PCR template and DNA oligonucleotides (also called DNA primers), which are required for initiation of DNA synthesis. The vast majority of PCR methods use thermal cycling, i.e., alternately heating and cooling the PCR sample through a defined series of temperature steps. In the first step, the two strands of the DNA double helix are physically separated at a high temperature in a process called DNA melting. In the second step, the temperature is lowered and the two DNA strands become templates for DNA polymerase to selectively amplify the target DNA. The selectivity of PCR results from the use of primers that are complementary to the DNA region targeted for amplification under specific thermal cycling conditions.

PCR based assay: A PCR based assay is an assay that employs a PCR reaction, e.g. quantitative Polymerase chain reaction (qPCR), digital PCR (dPCR) or droplet digital PCR (ddPCR).

Quantitative Polymerase chain reaction (qPCR) or real-time polymerase chain reaction: A real-time polymerase chain reaction is a laboratory technique of molecular biology based on the polymerase chain reaction (PCR), which is used to amplify and simultaneously detect or quantify a targeted DNA molecule. The procedure follows the general principle of polymerase chain reaction (PCR); its key feature is that the amplified DNA is detected as the reaction progresses in "real time". Two common methods for the detection of products in quantitative PCR are: non-specific fluorescent dyes that intercalate with any double-stranded DNA, such as SYBR® Green and sequence-specific DNA probes consisting of oligonucleotides that are labelled with a fluorescent reporter, which permits detection only after hybridization of the probe with its complementary sequence to quantify nucleic acids.

Quantitative PCR is carried out in a thermal cycler with the capacity to illuminate each sample with a beam of light of a specified wavelength and detect the fluorescence emitted by the excited fluorophore. The thermal cycler is also able to rapidly heat and chill samples, thereby taking advantage of the physicochemical properties of the nucleic acids and DNA polymerase.

The PCR process generally consists of a series of temperature changes that are repeated 25-40 times. These cycles normally consist of three stages: the first, at around 95° C., allows the separation of the nucleic acid's double chain; the second, at a temperature of around 50-60° C., allows the binding of the primers with the DNA template; the third, at between 68-72° C., facilitates the polymerization carried out by the DNA polymerase. Due to the small size of the fragments the last step is usually omitted in this type of PCR as the enzyme is able to increase their number during the change between the alignment stage and the denaturing stage. In addition, some thermal cyclers add another short temperature phase lasting only a few seconds to each cycle, with a temperature of, for example, 80° C., in order to reduce the noise caused by the presence of primer dimers when a non-specific dye is used. The temperatures and the timings used for each cycle depend on a wide variety of parameters, such as: the enzyme used to synthesize the DNA, the concentration of divalent ions and deoxyribonucleotides (dNTPs) in the reaction and the bonding temperature of the primers. The type of quantitative PCR technique used depends on the DNA sequence in the samples, the technique can either use non-specific fluorochromes or hybridization probes.

RT-qPCR: An RT-qPCR assay involves a first step of reverse transcription and a second step of quantitative PCR as described above. The reverse transcription reaction and the quantitative PCR reaction may be performed separately so that in a first reaction the RNA is reverse transcribed into cDNA and in a second reaction the cDNA is transferred into a new reaction mixture for the quantitative PCR. Alternatively, the reverse transcription reaction and the quantitative PCR reaction may be performed in one step so that the reaction mixture comprises both the components of the reverse transcription reaction and the components of the quantitative PCR.

Multiplex assay: A multiplex assay is an assay which measures multiple analytes in one single assay, i.e. simultaneously. In the context of the present invention it refers to methods which allow the detection of at least two of the n different RNA molecule species within a mixture of n different RNA molecule species in one sample and in one run.

Digital PCR (dPCR), droplet digital PCR (ddPCR): In digital PCR (dPCR), respective PCR reactions are partitioned into multiple smaller reactions so that individual nucleic acid molecules within the sample are localized and amplified in many separate regions. Micro well plates, capillaries, oil emulsion (droplets), and arrays of miniaturized chambers with nucleic acid binding surfaces can be used to separate the RNA sample in multiple small reactions per reaction vessel. After multiple PCR amplification cycles, typically performed under saturating PCR conditions, the samples are analyzed for fluorescence signals with a binary readout of "0" (no signal) or "1" (signal). Using Poisson's law of small numbers, the distribution of target molecule within the sample can be accurately approximated allowing for a quantification of the target strand in the PCR product. Therefore, dPCR is not dependent on the number of amplification cycles to determine the initial sample amount, and thus eliminates the reliance on uncertain exponential data to quantify target nucleic acids. Therefore, dPCR allows absolute quantification of nucleic acids.

Suitable commercial systems that may be used to perform dPCR comprise chip-based QuantStudio™ 3D digital PCR System (Thermo Fisher, Waltham, MA, USA), Rain Drop Plus™ system (RainDance Technologies, Lexington, MA, USA), or QX200™, AutoDG™, and Droplet Digital™ PCR System (BioRad Laboratories, Hercules, CA, USA).

Chip-based digital PCR measures absolute quantities by counting nucleic acid molecules partitioned in independent reaction wells. Commercially available systems for chip-based dPCR comprise QuantStudio™ 3D digital PCR System (Thermo Fisher, Waltham, MA, USA). A PCR reaction is divided into around 20,000 independent reaction wells on a chip that either contain or not contain template. The sealed chip is then subjected to PCR amplification. Each well containing template is leading to PCR positive signals (positive well) and each well that is not containing template is leading to negative PCR signals (negative wells). Positive and negative wells are counted allowing quantitation of template concentration using Poisson distribution algorithm.

Droplet digital PCR (ddPCR) measures absolute quantities by counting nucleic acid molecules encapsulated in discrete, volumetrically defined water-in-oil droplet partitions. Commercially available systems for ddPCR comprise Droplet Digital™ PCR System (BioRad Laboratories, Hercules, CA, USA) or Rain Drop Plus™ system (RainDance Technologies, Lexington, MA, USA). A PCR reaction is divided into around 20,000 droplets that either contain or not contain template leading to PCR positive and negative droplets that are counted allowing quantitation of template concentration using Poisson distribution algorithm. The droplets are generated using a droplet generator. ddPCR enables more precise absolute quantification as compared to classic relative quantitation which is limited due to the doubling during each cycle.

ddPCR has several advantages over conventional methods (e.g. qPCR) because no standard curve is needed for quantification, it is a more robust method (even sub-optimal primer pairs that lead to false positive or false negative signals will be eventually give a correct concentration due to the Poisson distribution algorithm), and enables precise (diagnostic) quantification (Resolution of standard qPCR: 0.5 cycles (+/−50%) vs. 10% for ddPCR (using acoustic pipetting 1.5% accuracy possible).

Chemical modifications: The term "RNA modification" as used herein may refer to chemical modifications comprising backbone modifications as well as sugar modifications or base modifications.

In this context, a modified RNA molecule as defined herein may contain nucleotide analogues/modifications, e.g. backbone modifications, sugar modifications or base modifications. A backbone modification in connection with the present invention is a modification, in which phosphates of the backbone of the nucleotides contained in an RNA molecule as defined herein are chemically modified. A sugar modification in connection with the present invention is a chemical modification of the sugar of the nucleotides of the RNA molecule as defined herein. Furthermore, a base modification in connection with the present invention is a chemical modification of the base moiety of the nucleotides of the RNA molecule. In this context, nucleotide analogues or modifications are preferably selected from nucleotide analogues, which are applicable for transcription and/or translation.

Purification: As used herein, the term "purification" or "purifying" is understood to mean that the desired RNA in a sample is separated and/or isolated from impurities, intermediates, byproducts and/or reaction components present therein or that the impurities, intermediates, byproducts and/or reaction components are at least depleted from the sample comprising the RNA. Non-limiting examples of undesired constituents of RNA-containing samples which therefore need to be depleted may comprise degraded fragments or fragments which have arisen as a result of premature termination of transcription, or also excessively long transcripts if plasmids are not completely linearized. Furthermore, intermediates may be depleted from the sample such as e.g. template DNA (for RNA IVT). Additionally, reaction components such as enzymes, proteins, bacterial DNA and RNA, small molecules such as spermidine, buffer components etc. may have to be depleted from the RNA sample. In addition, impurities such as, organic solvents, and nucleotides or other small molecules may be separated.

Preferably, the RNA is purified by a HPLC procedure as described in WO 2008/077592 A1. RNA may also be purified by tangential flow filtration (WO 2016/193206 A1 or WO 2014/152966 A1), oligo d(T) purification (WO 2014/152031 A1), ion exchange chromatography (WO 2014/144767 A1), hydroxyapatite chromatography (WO 2014/140211 A1) or core bead flow-through chromatography (WO 2014/140211 A1), or combinations thereof. With respect to the specific methods, the disclosures of WO 2008/077592 A1, WO 2016/193206 A1, WO 2014/152031 A1, WO 2014/144767 A1, WO 2014/152966 A1, and WO 2014/140211 A1 are incorporated herewith by reference.

Ideally, the RNA sample has a higher purity and/or integrity after purification than the starting material. The purity may be determined by methods commonly known to the skilled person, e.g. by gas chromatography, quantitative PCR, analytical HPLC or gel electrophoresis. In preferred embodiments, the RNA sample is a purified RNA sample.

Purified RNA (sample), degree of RNA purity: As used herein, "purified RNA" or "pure RNA" has to be understood as RNA which has a higher purity after certain purification steps (e.g., HPLC, TFF, precipitation steps) than the starting material (e.g., in vitro transcribed RNA). Typical impurities that are essentially not present in purified RNA comprise peptides or proteins (e.g., enzymes derived from DNA dependent RNA in vitro transcription, e.g., RNA polymerases, RNases, BSA, pyrophosphatase, restriction endonuclease, DNase), spermidine, abortive RNA sequences, RNA fragments, free nucleotides (modified nucleotides, conventional NTPs, cap analogue), plasmid DNA fragments, buffer components (HEPES, TRIS, $MgCl_2$) etc. Other impurities that may be derived from e.g. fermentation procedures comprise bacterial impurities (bioburden, bacterial DNA) or impurities derived from purification procedures (organic solvents etc.). WO 2014/144039 provides an RNA production procedure that includes various quality control steps and purification steps to obtain purified RNA (with respect to the quality control steps and purification the disclosure of WO 2014/144039 is incorporated herein by reference).

Accordingly, it is desirable in this regard for the "degree of RNA purity" to be as close as possible to 100%. It is also desirable for the degree of RNA purity that the amount of full length RNA transcripts is as close as possible to 100%.

Accordingly, "pure RNA" or "purified RNA" as used herein has a degree of purity of more than 70%, 75%, 80%, 85%, very particularly 90%, 91%, 92%, 93%, 94%, 95%, 96%, 97%, 98% and most favorably 99% or more.

The degree of purity may for example be determined by an analytical HPLC, wherein the percentages provided above correspond to the ratio between the area of the peak for the target RNA and the total area of all peaks representing the by-products. Alternatively, the degree of purity may for example be determined by an analytical agarose gel electrophoresis or capillary gel electrophoresis.

Complexed RNA/RNA-carrier complex: The term "complexed RNA" ("packaged RNA", "encapsulated RNA") includes one or more RNA molecules which are present in complexed form with at least one carrier compound. RNA molecules complexed with at least one carrier compound are denoted as "RNA-carrier complex". "RNA-carrier complexes" encompass, e.g., RNA nanoparticles and RNA microparticles. Usually an RNA-carrier complex comprises more than one RNA molecules which can belong to the same or different RNA molecule species. In an ideal case, although not necessary, each RNA-carrier complex comprises at least one, preferably more than one, RNA molecules of each of the n different RNA molecule species.

Preferably, "complexed RNA" according to the invention comprises RNA molecules that are all or at least partially complexed or encapsulated or packaged with at least one carrier compound. In another preferred embodiment, different types of carrier compounds are present in one RNA-carrier complex. Typical forms of RNA-carrier complexes are liposomes, lipid nanoparticles (LNPs) and PEGylated peptide-based polymer complexes and protamine-complexed RNA nanoparticles. Of course, it is also possible to have different types of RNA-carrier complexes present in one RNA sample.

DETAILED DESCRIPTION OF THE INVENTION

As discussed above, the inventors found that reverse transcription in combination with a PCR based assay, reverse transcription-(droplet) digital PCR (RT-(d)dPCR), is an ideal method for the quality control of RNA mixtures, i.e. of an RNA sample comprising n different RNA molecule species, wherein each of the n different RNA molecule species comprises one or more coding RNA molecules of synthetic origin, wherein n is an integer of at least 1. Advantageously, the inventive method is fast, robust (provides reproducible results), easy to handle, automatable, and cost effective allowing for the characterization of presence, quantity, quantitative ratio and integrity of all n different RNA molecule species within a mixture of RNA molecule species. In addition, the inventors developed a method to analyze RNA mixtures comprising n different RNA molecule species, wherein each of the n different RNA molecule species comprises one or more coding RNA molecules of synthetic origin which are present in complexed form, wherein n is an integer of at least 1. For example, RNA samples comprising nanoparticles wherein single nanoparticles or defined numbers of nanoparticles may be analyzed with respect to the presence, quantity, quantitative ratio and integrity of each of the n different RNA molecule species complexed or encapsulated in the respective nanoparticle or in the defined number of nanoparticles. Accordingly, the present invention relates to a method for quality control analysis of an RNA sample comprising n different RNA molecule species using reverse transcription and a polymerase chain reaction (PCR) based assay, wherein each of the n different RNA molecule species comprises one or more coding RNA molecules of synthetic origin, wherein n is an integer of at least 1 or at least 2, thereby determining at least one quality parameter.

As already explained above, the method of the present invention relates to the quality control analysis of an RNA sample. Optionally, this RNA sample is a pharmaceutical sample which further comprises a pharmaceutically acceptable carrier and optionally further pharmaceutically acceptable excipients. Hence, the method may be used to analyze a pharmaceutical sample ready to be administered to a patient or to analyze a sample during or after manufacture. However, typically, the method is used for quality control of an RNA containing sample which is intended for use as a medicament, independent from whether the sample already contains necessary pharmaceutically acceptable carriers and/or excipients which are required for administration or according to regulatory matters or whether the sample does not contain necessary pharmaceutically acceptable carriers and/or excipients for administration. Although suitable for analyzing any RNA samples, the method is particularly intended for quality control of RNA based medicaments and pharmaceutical RNA compositions. Typical pharmaceuticals carriers include water, usually pyrogen-free water, isotonic saline or buffered (aqueous) solutions, oils and other pharmaceutically acceptable liquids, gases and solid compounds which may be useful to administer the RNA sample to a patient in need thereof. Typical pharmaceutically acceptable excipients include buffering agents, salts, tonicity modifiers, sugars, sugar alcohols, lipids, preservatives, polymers, proteins, peptides, amino acids, alcohols, further pharmaceutically acceptable agents, complexing carriers as mentioned herein and so forth. Pharmaceutically acceptable carriers and excipients are known to the skilled person in the field of pharmaceutical formulation and medicament development. It may be necessary to remove some of the pharmaceutically acceptable carriers and/or excipients from the RNA sample prior to analysis by the inventive method. Methods to do so are known to the skilled person.

The method of the present invention comprises reverse transcription and a PCR based assay. By reverse transcription, the RNA molecules in the RNA sample are used for the in vitro production of complementary DNA (cDNA). Reverse transcriptases use the RNA molecules and a short primer complementary to the 3' end of the RNA to direct the synthesis of the first strand cDNA, which can then be used as a template for the PCR based assay, (d)dPCR.

The skilled person knows conditions which are sufficient for reverse transcription to occur. The RNA is typically incubated with a reverse transcriptase, at least one primer and deoxynucleotides in a suitable buffer at a temperature of about 37° C. to about 42° C. for about one hour (reaction conditions depend on the used reverse transcriptase enzyme and can be easily adapted by the experimenter). The primer(s) used for reverse transcription may be random, for example hexanucleotides with a random sequence or an oligo(dT) primer hybridizing to the poly(A) stretch of mRNA, or may be target specific. In general, "target specific" means that the primer or any other molecule to bind is specific for a single RNA/cDNA molecule species. Therefore, e.g. the primer only binds to the target RNA/cDNA molecule species as the n different RNA/cDNA species in the sample may differ from each other in their nucleic acid sequence and/or length.

In a preferred embodiment, the method comprises the following steps:

a) simultaneous reverse transcription of the one or more coding RNA molecules of at least one RNA molecule species of the n different RNA molecule species in a single reaction vessel, thereby providing a cDNA sample comprising at least one cDNA molecule species, wherein each cDNA molecule species corresponds to one of the at least one RNA molecule species, b) subjecting the cDNA sample to the PCR based assay, and c) determining the at least one quality parameter of the RNA sample.

Preferably, n is an integer of at least 2, or at least 3, 4, 5, 6, 7, 8, 9, 10, 11, 12, 15, 20, 25, 30, 50, 75. 100, 125, 150, 175, 200, 220, or is an integer in the range of 1 to 200, preferably is in the range of 25-175, more preferably of 30-150, even more preferably of 50-125.

Each cDNA molecule species corresponds to one of the at least two RNA molecule species, wherein "corresponds" is a term well understood by the skilled person in the field of reverse transcription and other RNA/DNA handling methods and means that one cDNA molecule species has a DNA sequence which is complementary to the RNA sequence of an RNA molecule of the respective RNA molecule species.

Step a) includes that the RNA sample comprising the one or more RNA molecules of all RNA molecule species is subjected to reverse transcription without prior separation of the RNA molecule species. Hence, reverse transcription is performed on the RNA sample, comprising one (n=1) or more (n>1) RNA molecule species. However, in an alternative embodiment, the one or more RNA molecules may be separated according to the RNA molecule species they belong to. In this embodiment, for each RNA molecule species a single reverse transcription reaction is performed in separate reaction vessels. The RNA molecule species may be separated e.g. by HPLC, agarose gel electrophoresis and preparative polyacrylamide gel electrophoresis.

In an alternative embodiment, the method comprises the following steps:

a1) separate reverse transcription of the one or more coding RNA molecules of each RNA molecule species of the n different RNA molecule species in a separate reaction vessel, thereby providing n different cDNA samples each comprising one cDNA molecule species, wherein each cDNA molecule species corresponds to one of the at least two RNA molecule species, b) subjecting the cDNA samples to the PCR based assay, and c) determining the at least one quality parameter of the RNA sample.

In case step a1) is present, after step a1) all of the n different cDNA samples may be united (pooled) and step b1) be performed. Or, in case step a1) is present, after step a1) two or more of the n different cDNA samples may be united (pooled) and step b2) be performed.

Additionally, suitable quality control steps during or after reverse transcription of the produced cDNA molecule species may be introduced to evaluate whether all n different cDNA molecule species have been produced. Methods for evaluating the presence of the cDNA molecule species are well known to the skilled person.

Preferably, step b) comprises a step of b1) simultaneous analysis of all cDNA molecule species in a single reaction vessel, or b2) analysis of two or more cDNA molecule species in a single reaction vessel, or b3) analysis of each cDNA molecule species in a separate reaction vessel.

Preferably, the PCR based assay (dPCR, preferably ddPCR) is performed in a parallel fashion (for each target one individual PCR reaction is performed) as in step b3). This means that the cDNA molecule species may be separated via standard methods in the art, e.g. micropreparative capillary gel electrophoresis, agarose gel electrophoresis. Preferably, the obtained cDNA molecule species are not separated and for each target one individual PCR reaction with target specific primer(s) and the same detectable label is performed.

Alternatively, the PCR based assay (dPCR, preferably ddPCR) is performed in one simultaneous (multiplexed) reaction using different detectable labels and, optionally, different primers per target.

In step b1), all cDNA molecule species are simultaneously subjected to the PCR based assay in a single reaction vessel. In case of step a), wherein a simultaneous reverse transcription of the one or more coding RNA molecules of at least two, preferably all or any number between 2 and n, RNA molecule species of the n different RNA molecule species in a single reaction vessel, the sample may directly be subjected to the PCR based assay.

In step b2), two or more cDNA molecule species are subjected to the PCR based assay in a single reaction vessel. This embodiment includes that subgroups of two or more, e.g. 2, 3, 4, 5, 6, 7, 8, 9, 10 and more, cDNA molecule species are subjected to the PCR based assay in separate reaction vessels. If all n cDNA molecule species are separately subjected to the PCR based assay, step b3) applies. Step b2) also covers embodiments, wherein n, n/2, n/3, n/4 and so forth cDNA molecule species are subjected to separate PCR based assay reaction vessels. The experimenter can individually select the number of cDNA species which are to be analyzed together in a single reaction vessel in the PCR based assay. The only restriction is that in case of more than one cDNA molecule species which is analyzed in one single reaction vessel, the detection of each distinct cDNA molecule species must be possible e.g. by selecting a different fluorescent probe for each cDNA molecule species or by selecting target-specific fluorescent probes. This will be discussed in more detail below.

Step a) and b) may be performed in a single step/simultaneous and in one reaction vessel. In case of steps b2) and b3), the cDNA sample is divided by the number of reactions which are to be performed in separate reaction vessels. In case of step b3) and if all n different RNA molecule species are to be analyzed, the cDNA sample is divided into n separate reaction vessels. This implies that the method of the invention comprises that not all of the n different RNA molecule species in the RNA sample may need to be analyzed. The choice of which and how many of the n different RNA molecule species in the RNA sample is analyzed lies completely with the experimenter.

The PCR based assay is digital PCR (dPCR), more preferably droplet digital (ddPCR). In a highly preferred embodiment, RT-dPCR or RT-ddPCR is employed.

Digital PCR may be a system selected from a group consisting of micro well plate systems, capillary based systems, oil emulsion (droplets) based systems, and arrays of miniaturized chambers. Accordingly, in preferred embodiments, the digital PCR is a system selected from the group consisting of micro well plate digital PCR, capillary digital PCR, droplets digital PCR, and array digital PCR. Suitable commercial systems that may be used to perform dPCR comprise chip-based QuantStudio™ 3D digital PCR System (Thermo Fisher, Waltham, MA, USA), Rain Drop Plus™ system (RainDance Technologies, Lexington, MA, USA), or QX200™, AutoDG™, and Droplet Digital™ PCR System (BioRad, Hercules, CA, USA). In embodiments where digital PCR is used, the method does not additionally comprise a step of generating a reference standard curve.

In a preferred embodiment, droplet dPCR is used as PCR based assay to quantify the at least two cDNA molecules in the cDNA sample obtained by reverse transcription. Droplet dPCR (ddPCR) measures absolute quantities by counting nucleic acid molecules encapsulated in discrete, volumetrically defined water-in-oil droplet partitions. In ddPCR, each PCR reaction is divided into around 20,000 droplets (the number of droplets may depend on the used ddPCR device and can be easily adapted by the skilled experimenter) that either contain or not contain template leading to droplets with either PCR positive (signal) or negative (no signal) droplets that are counted and thus allow for the quantitation of template concentration in the RNA sample using Poisson's distribution algorithm. ddPCR enables more precise absolute quantification as compared to classic relative quantitation which is limited due to the doubling during each cycle. In such an embodiment, step b) comprises contacting the cDNA molecule sample with at least one set of PCR primers under conditions sufficient for PCR amplification of the cDNA, wherein each PCR primer binds specifically to a part of a cDNA molecule of each cDNA molecule species. Either after the reverse transcription step a) or a1) or simultaneously thereto, the cDNA is amplified in a dPCR reaction as defined above. The primers used for the dPCR reaction are selected such that they bind to a part of the sequence of the cDNA corresponding to the RNA species so that this part is amplified in the PCR reaction. Preferably, the PCR reaction conditions are chosen to allow for a saturating amplification of the cDNA.

In a particularly preferred embodiment, the digital PCR is an oil emulsion based PCR system, performed e.g. using Droplet Digital™ PCR System (BioRad, Hercules, CA, USA).

Prior to performing dPCR, a cDNA dilution step may be required. For example, the cDNA sample obtained in step a) or a1) is diluted so that 1,000 to 100,000, more preferably 5,000 to 50,000, and most preferably about 20,000 cDNA molecules are present in the cDNA sample subjected to the dPCR in step b). The cDNA sample obtained in step a) or diluted as explained above may be partitioned for dPCR, e.g. using a droplet generator (e.g. GX200 droplet generator (Bio-Rad, Hercules, CA, USA)) and used for the dPCR amplification reaction.

ddPCR has several advantages over conventional methods because no standard curve is needed for quantification, it is a more robust method (even sub-optimal primer pairs that lead to false positive or false negative signals may give a correct concentration due to the Poisson's distribution algorithm), and enables precise (diagnostic) quantification of about 10% accuracy (using (automated) acoustic pipetting about 1.5% accuracy may be possible as the impact of human error in e.g. pipetting is largely reduced).

Preferably, all pipetting steps in the disclosed procedure are performed using an acoustic liquid handler to avoid inaccuracy due to human handling. Acoustic liquid handlers are e.g. available from Labcyte Inc., Sunnyvale, CA, USA, and are used according to the manufacturer's instructions.

In a preferred embodiment, the PCR based assay employs a detectable label. More preferably, the detectable label is a fluorescent probe, preferably comprising an intercalating dye or a fluorophore-quencher system. In a particularly preferred embodiment, the detectable label is a cyanine dye.

Suitable intercalating dyes are ethidiumbromide, SYBR™ green etc. Other suitable detectable probes comprise TaqMan probes that derive their fluorescence signal from the hydrolysis of the probe by 5' to 3' exonuclease activity. The hydrolysis separates fluorescein from a quenching dye and results in an increased fluorescein signal which may be detected, subsequently.

Preferably, detectable labels comprise fluorophore-quencher system, wherein the probe only emits light in the presence of the cDNA molecule to be detected. Such probes comprise EvaGreen®.

In a preferred embodiment, the PCR based assay employs a (target) sequence specific detectable label. Alternatively, or in addition to the fluorescent probes mentioned above, target-sequence-specific fluorescent probes (hybridization probes) may be used, e.g. target specific fluorophore-quencher probes. Such probes may be chosen to hybridize between the two primers of the amplicon. "Target specific" or "sequence specific" in this context means that the fluorescent probes binds to the cDNA molecules of a specific cDNA molecule species. In general, "target specific" or "sequence specific" means that a compound, probe or short nucleic acid sequence molecule binds to a specific nucleic acid sequence and not randomly to all nucleic acid sequences, i.e. is nucleic acid sequence-specific.

Preferably, the detectable label is selected from the group consisting of fluorescein, ethidiumbromide, SYBR™ green I (2-{2-[(3-dimethylamino-propyl)-propylamino]-1-phenyl-1H-chinoline-4-ylidenmethyl}-3-methyl-benzothiazol-3-ium-cation), LCgreen®, SYTO® 9, EvaGreen®, Resolight®, Chromofy, BOXTO, and monomethine dyes.

Optionally, in step b1) for each cDNA molecule species a different detectable label is used, or in step b2) for each cDNA molecule species to be analyzed in a single reaction vessel a different detectable label is used. Step b1) comprises the simultaneous analysis of all cDNA molecule species in a single reaction vessel. Step b2) comprises the simultaneous analysis of two or more cDNA molecule species of the n different cDNA molecule species in a single reaction vessel, i.e. that subgroups of the cDNA molecule species are united (pooled) in a single reaction vessel and are analyzed simultaneous. For example, if n=10, step b2) may comprise that 5 cDNA molecule species are analyzed simultaneously in a single reaction vessel, or may comprise that 2, 4 and 4 cDNA molecule species are analyzed in a single reaction vessel. The skilled person understands that of course any other combination is also possible and envisaged in the method of this invention. The cDNA molecule species which are formed in step a) but are not to be analyzed in a specific reaction vessel in step b2) or step b3), may or may not be removed or separated from the cDNA sample to be analyzed.

In one embodiment, (d)dPCR is performed in a parallel manner (see step b3)), i.e. each cDNA molecule species is analyzed in a separate reaction vessel meaning that for each target cDNA species a separate (d)dPCR reaction is performed. In this case, the same or different detectable labels can be used for the cDNA molecule species, preferably the detectable label is EvaGreen®.

According to step b1), the n different cDNA molecule species can be analyzed simultaneously, i.e. in a multiplexed reaction, so that the sample comprising all cDNA molecule species is contacted with n detectable probes, wherein each detectable probe is sequence specific for the cDNA molecules of one of the n different cDNA molecule species corresponding to one of the n different RNA molecule species in a single reaction vessel. In this case, for each cDNA molecule species present in the single reaction vessel a different or distinguishable detectable label has to be used so that the double-stranded nucleic acid molecules which are formed in the PCR based assay can be distinguished from each other. If the detectable labels in the multiplexed reaction are fluorescent labels, the n different labels should be selected so that they can be distinguished from each other (detection of light emission of the n different fluorescent labels; alternatively: spectral unmixing of light spectrum emitted by all fluorescent labels). Ideally the n different fluorescent labels should not interfere with each other, i.e. that the spectrum of light emitted by the fluorescent labels does not overlap. In step b1) thus preferably target/sequence specific fluorescent probes are used and or fluorophore-quencher systems. The same applies in step b2) for the cDNA molecule species which are to be analyzed simultaneously in a single reaction vessel.

The quality parameter is preferably selected from the group consisting of quantity of the one or more coding RNA molecules of at least two RNA molecule species, presence of the one or more coding RNA molecules of at least two RNA molecule species, integrity of the one or more coding RNA molecules of at least two RNA molecule species and quantitative ratio between the one or more coding RNA molecules of at least two RNA molecule species.

For determining the quantity of the at least one RNA species in dPCR, no reference curve is necessary. The obtained fluorescence signals, detected e.g. using a QX200 droplet reader (Bio-Rad), are transferred into a binary read-out of "0" (no signal) or "1" (signal) as explained above. By approximation of the binary signals using Poisson's law of small numbers, the quantity of each RNA molecule species can be determined.

The determination of presence of a specific RNA molecule species is based on the same principle. Using a target/sequence specific detectable probe, the presence is confirmed if a positive signal of the respective detectable probe is recognized in case that more than one cDNA molecule species is to be analyzed in a single reaction vessel.

For determining the ratio between the one or more coding RNA molecules of at least two RNA molecule species, the quantity of both RNA molecule species to be analyzed is determined and set in relation to each other.

The PCR based assay (RT-(d)dPCR) may also be used to determine the integrity of the RNA molecule species, i.e. whether the one or more coding RNA molecules of synthetic origin of the RNA molecule species to be analyzed are intact, i.e. neither amended in their nucleic acid sequence nor truncated or elongated, by contacting the cDNA molecule species corresponding to the RNA molecule species to be analyzed with at least two different primer sets, wherein each of the at least two primer sets binds to and amplifies a different part of the cDNA molecule sequence corresponding to the RNA molecule species to be analyzed, leading to two different PCR products corresponding to the different parts of the cDNA sequence. The amount of each PCR product can be determined as described above (a standard curve is not required). If the amount of the first PCR product is substantially the same as the amount of the second PCR product, the corresponding RNA species is considered to have integrity. Also here target/sequence specific detectable probes are to be used if more than one cDNA species is to be analyzed in a single reaction vessel.

Preferably, the first and second primer sets bind to opposite ends of the cDNA corresponding to the at least one RNA species, such as the 5' end of the cDNA and the 3' end of the cDNA. If the analysis is independent of the target sequence, the first and second primer sets preferably bind to cDNA sequences located 5' of the sequence corresponding to the target sequence and 3' of the sequence corresponding to the target sequence, such as a sequence in the 5' untranslated and the 3' untranslated region, if the target sequence is a coding sequence.

Alternatively, the one primer set binds to and amplifies the whole coding sequence or essentially the whole cDNA sequence, and at least one primer set binds to the 5' end of the cDNA and/or the 3' end of the cDNA. If the amount of the first PCR product corresponding to the whole coding sequence/the whole cDNA sequence is substantially the same as the amount of the at least one PCR product corresponding to the 5' end and/or 3' end of the cDNA, the corresponding RNA species is considered to have integrity.

The PCR reactions with the at least two different primer sets can take place in parallel reactions, so that one part of the cDNA sample corresponding to the RNA molecule species to be analyzed is amplified using the first primer set and another part of said cDNA sample is amplified using the second primer set in a separate reaction. In this case, the detectable label used for detecting and quantifying the PCR products may be the same in both reactions.

In embodiments, the RNA sample comprises one RNA molecule species, i.e. n is 1.

In preferred embodiments, the RNA sample comprises n different RNA molecule species which differ in their nucleic acid sequence, either in the length of the nucleic acid sequence and/or in the sequence of the nucleic acids within the RNA molecule. Often, the RNA molecule species have a comparable length, i.e. the length differs not more than 10% but differ in the nucleic acid sequence. Hence, each RNA sample comprises n different populations of RNA molecules, i.e. RNA molecule species, wherein n is an integer of at least 1 or at least 2 (thereby forming an RNA mixture). The integer n can be at least 1 and therefore e.g. can be 1, 2, 3, 4, 5, 6, 7, 8, 9, 10, 11, 12, 13, 14, 15, 16, 17, 18, 19, 20, 21 and so forth. Preferably, n is an integer of at least 3 or in the range of 1 to 200, more preferably of 3 to 150, even more preferably of 4 to 100, and most preferably of 5 to 50. Each of the n different RNA molecule species comprises one or more coding RNA molecules of synthetic origin. In a preferred embodiment, if n is 2, the one or more RNA molecules of a first RNA molecule species code for a first protein, peptide or variant thereof and the one or more RNA molecules of a second RNA molecule species code for a second protein, peptide or variant thereof. In another embodiment, if n is 3, the RNA sample comprises a third RNA molecule species comprising one or more RNA molecules which code for a third protein, peptide or variant thereof and so forth for n=4, 5, 6 and higher.

In alternative embodiments, some of the n different RNA molecule species may code for the same protein, peptide or variant thereof but may differ in their nucleic acid coding sequence (e.g., different sequence adaptations, GC content, CAI) and/or differ in their non-coding regions (e.g., different UTR elements). Such RNA molecule species are also considered different RNA molecule species.

The skilled person understands that the RNA sample of the invention may comprise at least one RNA molecule species, preferably at least 2 RNA molecule species each comprising one or more RNA molecules, i.e. at a minimum an RNA sample comprises two RNA molecules, wherein each of the two RNA molecules belong to one of the two RNA molecule species. However, typically an RNA sample comprises a group of RNA molecules belonging to either one of the at least 2 RNA molecule species in the sample. The RNA molecules belonging to each RNA molecule species may be present in different amounts or may be present in the same amount.

The one or more RNA molecules are coding RNA molecules and thus may be mRNA. However, the invention also provides a method for quality control analysis of an RNA sample comprising n different RNA molecule species using reverse transcription and a polymerase chain reaction (PCR) based assay, wherein each of the n different RNA molecule species comprises one or more RNA molecules of synthetic origin, wherein n is an integer of at least 2, thereby determining at least one quality parameter, wherein the one or more RNA molecules are selected from the group consisting of mRNA, non-coding immunostimulating RNA (isRNA), replicon RNA, small interfering RNA (siRNA), saRNA (small activating RNA), antisense RNA, CRISPR RNA (small guide RNA, sgRNA), microRNA (miRNA), and Piwi-interacting RNA (piRNA). All embodiments described herein also relate to the aforementioned method even if only mentioned in connection with coding RNA molecules. In a preferred embodiment, the one or more RNA molecules are mRNA or non-coding isRNA. In a preferred embodiment, the one or more RNA molecules are of synthetic origin and thus are non-cellular RNA, i.e. are not purified from a living cell, either from cell culture or from a living human or animal or microorganism.

Preferably, the one or more coding RNA molecules are obtained by an in vitro method. More preferably, the in vitro method is in vitro transcription, e.g. DNA dependent RNA in vitro transcription, or chemical RNA synthesis.

In a preferred embodiment, the one or more (coding) RNA molecules are not non-coding RNAs, e.g. long non-coding (lncRNA) 21A and NDM29. In another preferred embodiment, the one or more (coding) RNA molecules are not cell derived extracellular RNA molecules. In another preferred embodiment, the one or more (coding) RNA molecules of one RNA molecule species are not ERCC-25 and of another RNA molecule species present in the RNA sample are not ERCC-99. In another preferred embodiment, the one or more (coding) RNA molecules of one RNA molecule species are not MMP1 and of another RNA molecule species present in the RNA sample are not UBC. In another preferred embodiments, the one or more (coding) RNA molecules of one RNA molecule species are not ERCC-25 and of another RNA molecule species present in the RNA sample are not UBC. In another preferred embodiment, the RNA sample does not comprise a member selected from the group consisting of lncRNA 21A, NDM29, ERCC-25, ERCC-99, MMP1 and UBC. In another preferred embodiment, the RNA sample does not comprise a member selected from the group consisting of lncRNA 21A, NDM29, ERCC-25, ERCC-99, MMP1 and UBC.

Moreover preferred is that prior to step a) the one or more coding RNA molecules are purified, optionally using a method selected from the group consisting of high-performance liquid chromatography (HPLC), tangential flow filtration, oligo d(T) purification, ion exchange chromatography, hydroxyapatite chromatography, core bead flow-through chromatography, and combinations thereof. Further information on RNA purification is given elsewhere in the description. Preferred in that context is high-performance liquid chromatography (HPLC), in particular reverse phase HPLC (RP-HPLC).

In a particularly preferred embodiment, the one or more RNA molecules are coding RNA molecules and the one or more RNA molecules of each RNA molecule species encode a different amino acid sequence. Most preferably, the one or more coding RNA molecules of each of the n different RNA molecule species encodes for one of n different peptides.

In another preferred embodiment, the RNA sequences of the one or more coding RNA molecules of each of the n different RNA molecule species are at least 80% identical to each other.

More preferably, the n different RNA molecule species are selected from a group consisting of n different RNA molecule species encoding n different proteins or peptides derived from different serotypes or strains of a pathogen, n different RNA molecule species encoding n different antigens from one pathogen, n different RNA molecule species encoding n different antigens from different pathogens, n different RNA molecule species encoding n different isoforms or variants of an antigen, preferably a cancer antigen, n different RNA molecule species encoding n different epitopes of an antigen, n different RNA molecule species encoding n different cancer specific and/or patient specific cancer antigens, n different RNA molecule species encoding n different antibodies or antibody chains, n different RNA molecule species encoding n different proteins of one or more metabolic pathways, n different RNA molecule species encoding for n different isoforms of a protein for molecular therapy, n different RNA molecule species encoding for n different therapeutically active RNA molecule species, and combinations thereof.

Preferably, each of the n different RNA molecule species encodes for an antigen of different serotypes or strains of a pathogen or a different pathogen, for a different allergen, for a different autoimmune antigen, for a different antigen of a pathogen, for a different isoform or variant of a cancer or tumor antigen, for a different tumor antigen of one patient, for one antibody among a group of antibodies which target different epitopes of a protein or of a group of proteins, for different proteins of a metabolic pathway, for a single protein among a group of proteins which are defect in a subject, or for a different isoform of a protein for molecular therapy.

More preferably, the pathogen is selected from the group consisting of a virus, bacterium, protozoon, prion, fungus, viroid, and parasite.

The n different RNA molecule species may also each encode a different allergen associated with allergy or an allergic disease (allergens or allergenic antigens).

The n different RNA molecule species may also each encode for a different autoimmune self-antigens (autoantigens).

The n different RNA molecule species may also each encode a different therapeutic antibody selected from the group consisting of antibodies which are used inter alia for the treatment of cancer or tumour diseases, immune disorders, infectious diseases, Alzheimer's disease, asthma, and antibodies which are used for the treatment of diverse disorders, e.g. osteoporosis, tooth decay, idiopathic pulmonary fibrosis, focal segmental glomerulosclerosis, pain, muscular dystrophy, and Neovascular age-related macular degeneration.

The n different RNA molecule species may also each encode a different isoform or variant of a therapeutic protein which can be used inter alia in the treatment of metabolic or endocrine disorders.

These and other proteins are understood to be therapeutic, as they are meant to treat the subject by replacing its defective endogenous production of a functional protein in sufficient amounts. Accordingly, such therapeutic proteins are typically mammalian, in particular human proteins.

For the treatment of blood disorders, diseases of the circulatory system, diseases of the respiratory system, cancer or tumor diseases, infectious diseases or immunodeficiency therapeutic proteins may be encoded by the n different RNA molecule species of the invention.

The n different RNA molecule species may also each encode a different isoform or variant of adjuvant proteins.

In a particularly preferred embodiment, at least one of the one or more coding RNA molecules is present in complexed form with at least one carrier compound, thereby forming at least one RNA-carrier complex. A "carrier compound" is thus a chemical compound which can form an RNA-carrier complex with one or more RNA molecules. Typical forms of RNA-carrier complexes are liposomes, PEGylated peptide-based polymer complexes, lipoplexes and lipid nanoparticles (LNPs) complexing RNA molecules. More preferably, the at least one RNA-carrier complex comprises more than one of the one or more coding RNA molecules and/or comprises one or more coding RNA molecules of different or the same RNA molecule species. Typically but not necessarily, a great variety of RNA-carrier complexes is present in an RNA sample comprising complexed RNA molecules. Each RNA-carrier complex may comprise different amounts of RNA molecules belonging to different or the same RNA molecule species. Each RNA-carrier complex present in the RNA sample may comprise a different total number of RNA molecules and a different RNA molecule species composition. It is also possible that "empty" carrier complexes are present which do not comprise RNA molecules but only carrier compounds. It may also happen, although not preferred, that one RNA carrier-complex comprises only RNA molecules of a single RNA molecule species. It is further possible that not all of the RNA molecules present in the RNA sample are present in complexed form. Non-complexed RNA molecules may be present freely in the RNA sample ("free" or "non-complexed" RNA molecules and RNA molecules which are bound to the outer surface of the RNA-carrier complexes). However, preferably, at least 80% of the one or more coding RNA molecules in the RNA sample are present in the form of at least one RNA-carrier complex. More preferably, at least 85%, even more preferably at least 90%, 95%, 96%, 97%, 98% and most preferably at least 99% or 100% or the one or more RNA molecules present in the RNA sample are present in complexed form, i.e. present in one or more RNA-carrier complexes. According to the present invention, "complexed RNA" comprises RNA molecules that may be all or partially (i.e. at least one RNA molecule but not necessarily all RNA molecules) complexed with lipids or other carrier compounds to form one or more liposomes, PEGylated peptide-based polymer complexes, or lipid nanoparticles. Therefore, in some embodiments, "complexed RNA" comprises liposomes (comprising lipoplexes, which are herein to be understood as a complex of RNA molecules and lipids), PEGylated peptide-based polymer complex, and/or lipid nanoparticles (LNPs).

Preferably, the at least one carrier compound is a member selected from the group consisting of peptides, polymers, carbohydrates, cholesterol, polyethylene glycol (PEG), lipids, phospholipids, PEGylated lipids, cationic and polycationic compounds, and combinations thereof. The cationic or polycationic compound may be selected from the group consisting of cationic and polycationic polymers, cationic and polycationic peptides and proteins, preferably protamine, cationic and polycationic polysaccharides, cationic and polycationic lipids, and combinations thereof. As already explained above, the RNA-carrier complexes in the RNA sample comprising complexed RNA molecules may comprise different total amounts of RNA molecules and different amounts of the one or more RNA molecule species of the n different RNA molecule species. Moreover, each RNA-carrier compound complex may comprise a different RNA molecule species composition. Of course, it is also possible that different amounts of a specific carrier compound are present in each RNA-carrier complex and/or that the RNA-carrier complexes differ in their total amounts of carrier compound as well as of RNA molecules. The RNA-carrier complexes in an RNA sample may also differ with respect to their individual carrier compound composition. In one RNA sample, each RNA-carrier complex may contain different amounts of carrier compounds and RNA molecules and a different composition of carrier compounds and a different composition of RNA molecule species. Each RNA-carrier complex may further comprise a different total amount of RNA molecules, different amounts of the RNA molecules of each of n different RNA molecule species and a different composition of RNA molecules.

In preferred embodiments, the RNA molecules in the "complexed RNA" or "RNA-carrier complexes" are formulated together with a carrier compound being a cationic or polycationic compound and/or with a polymeric carrier.

Cationic or polycationic compounds, being particularly preferred carrier compounds in this context include protamine, nucleoline, spermine or spermidine, or other cationic peptides or proteins, such as poly-L-lysine (PLL), poly-arginine, basic polypeptides, cell penetrating peptides (CPPs), including HIV-binding peptides, HIV-1 Tat (HIV), Tat-derived peptides, penetratin, VP22 derived or analog peptides, HSV VP22 (Herpes simplex), MAP, KALA or protein transduction domains (PTDs), PpT620, proline-rich peptides, arginine-rich peptides, lysine-rich peptides, MPG-peptide(s), Pep-1, L-oligomers, calcitonin peptide(s), antennapedia-derived peptides (particularly from *Drosophila antennapedia*), pAntp, pIsl, FGF, lactoferrin, transportan, Buforin-2, Bac715-24, SynB, SynB(1), pVEC, hCT-derived peptides, SAP, or histones. More preferably, the mRNA/RNA molecules according to the invention are complexed with one or more polycations, preferably with protamine or oligofectamine, most preferably with protamine. In this context, protamine is particularly preferred.

Further preferred cationic or polycationic compounds, which can be used as carrier compounds to generate "complexed RNA" or "RNA-carrier complexes" may include cationic polysaccharides, for example chitosan, polybrene, cationic polymers, e.g. polyethyleneimine (PEI), cationic lipids, e.g. DOTMA ([1-(2,3-sioleyloxy)propyl)]-N,N,N-trimethyl¬ammonium chloride), DMRIE, di-C14-amidine, DOTIM, SAINT, DC-Chol, BGTC, CTAP, DOPC, DODAP, DOPE (Dioleyl phosphatidylethanol-amine), DOSPA, DODAB, DOIC, DMEPC, DOGS: Dioctadecylamidoglicyl-spermin, DIMRI (Dimyristo-oxypropyl dimethyl hydroxyethyl ammonium bromide), DOTAP (dioleoyloxy-3-(trimethylammonio)propane), DC-6-14 (O,O-ditetradecanoyl-N-(-trimethylammonioacetyl)diethanolamine chloride), CLIP1 (rac-[(2,3-dioctadecyloxy-propyl)(2-hydroxyethyl)]-dimethylammonium chloride), CLIP6 (rac-[2(2,3-dihexa-decyloxypropyl-oxymethyloxy)ethyl]trimethylammonium), CLIP9 (rac-2(2,3-dihexa-decyloxypropyl-oxysuccinyloxy)ethyl-trimethylammonium), oligo¬fectamine, or cationic or polycationic polymers, e.g. modified polyaminoacids, such as alpha-aminoacid-polymers or reversed polyamides, etc., modified polyethylenes, such as PVP (poly(N-ethyl-4-vinylpyridinium bromide)), etc., modified acrylates, such as pDMAEMA (poly(dimethylaminoethyl methylacrylate)), etc., modified amido-amines such as pAMAM (poly(amidoamine)), etc., modified polybetaamino¬ester (PBAE), such as diamine end modified 1,4 butanediol diacrylate-co- 5-amino-1-pentanol polymers, etc., dendrimers, such as polypropylamine dendrimers or pAMAM based dendrimers, etc., polyimine(s), such as PEI: poly(ethyleneimine), poly (propyleneimine), etc., polyallylamine, sugar backbone based polymers, such as cyclodextrin based polymers, dextran based polymers, chitosan, etc., silan backbone based polymers, such as PMOXA-PDMS copolymers, etc., block-polymers consisting of a combination of one or more cationic blocks (cationic blocks e.g. selected from a cationic polymer as mentioned above) and of one or more hydrophilic or hydrophobic blocks (e.g. polyethylene glycole); etc.

In a preferred embodiment, the at least one RNA-carrier complex comprises a member selected from the group consisting of liposome, lipid nanoparticle (LNP), and PEGylated peptide-based polymer complex and mixtures thereof. Hence, the carrier compounds assemble to form a liposome, LNP and/or PEGylated peptide-based polymer complex together with the at least one of the one or more coding RNA molecules which is thus present in complexed form. In the sense of the present invention, the terms "complexed RNA", "complexed RNA molecules" and "RNA-carrier complexes" do not encompass RNA molecules which are present in extracellular vesicles derived from cells.

In a preferred embodiment, the at least one RNA-carrier complex comprises a lipid nanoparticle (LNP).

In the context of the present invention, the term "lipid nanoparticle", also referred to as LNP, is not restricted to any particular morphology, and include any morphology generated when a cationic lipid and optionally one or more further lipids are combined, e.g. in an aqueous environment and/or in the presence of an RNA. For example, a liposome, a lipid complex, a lipoplex and the like are within the scope of a lipid nanoparticle (LNP). LNPs typically comprise a cationic lipid and one or more excipients selected from neutral lipids, charged lipids, steroids and polymer conjugated lipids (e.g., PEGylated lipid). The RNA may be encapsulated in the lipid portion of the LNP or an aqueous space enveloped by some or the entire lipid portion of the LNP. The RNA or a portion thereof may also be associated and complexed with the LNP.

The LNP comprising the one or more RNA molecule may have a mean diameter of from about 30 nm to about 150 nm, from about 50 nm to about 150 nm, from about 70 nm to about 100 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm, and are substantially non-toxic. The one or more RNA molecules, when present in one or more LNPs, are typically resistant to degradation with a nuclease in aqueous solution.

An LNP may comprise any lipid capable of forming a particle to which the one or more RNA molecules are attached, or in which the one or more RNA molecules are encapsulated. Preferably, the LNP comprising one or more RNA molecules comprises one or more cationic lipids, and one or more stabilizing lipids. Stabilizing lipids include neutral lipids and PEGylated lipids.

In one embodiment, the LNP consists essentially of (i) at least one cationic lipid; (ii) a neutral lipid; (iii) a sterol, e.g. cholesterol; and (iv) a PEG-lipid, e.g. PEG-DMG or PEG-cDMA, in a molar ratio of about 20-60% cationic lipid: 5-25% neutral lipid: 25-55% sterol; 0.5-15% PEG-lipid.

A preferred sterol is cholesterol. The sterol can be about 10 mol % to about 60 mol % or about 25 mol % to about 40 mol % of the lipid particle. In one embodiment, the sterol is about 10, 15, 20, 25, 30, 35, 40, 45, 50, 55, or about 60 mol % of the total lipid present in the lipid particle. In another embodiment, the LNPs include from about 5% to about 50% on a molar basis of the sterol, e.g., about 15% to about 45%, about 20% to about 40%, about 48%, about 40%, about 38.5%, about 35%, about 34.4%, about 31.5% or about 31% on a molar basis (based upon 100% total moles of lipid in the lipid nanoparticle).

The cationic lipid of an LNP may be cationisable, i.e. it becomes protonated as the pH is lowered below the pK of the ionizable group of the lipid, but is progressively more neutral at higher pH values. At pH values below the pK, the lipid is then able to associate with negatively charged nucleic acids. In certain embodiments, the cationic lipid comprises a zwitterionic lipid that assumes a positive charge on pH decrease.

The LNP may comprise any further cationic or cationisable lipid, i.e. any of a number of lipid species which carry a net positive charge at a selective pH, such as physiological pH.

Such lipids include, but are not limited to, N,N-dioleyl-N,N-dimethylammonium chloride (DODAC); N-(2,3-dioleyloxy)propyl)-N,N,N-trimethylammonium chloride (DOTMA); N,N-distearyl-N,N-dimethylammonium bromide (DDAB); N-(2,3dioleoyloxy)propyl)-N,N,N-trimethylammonium chloride (DOTAP); 3-(N-(N',N'dimethylaminoethane)-carbamoyl)cholesterol (DC-Chol), N-(1-(2,3-dioleoyloxy)propyl)N-2-(sperminecarboxamido)ethyl)-N,N-dimethylammonium trifluoroacetate (DOSPA), dioctadecylamidoglycyl carboxyspermine (DOGS), 1,2-dioleoyl-3-dimethylammonium propane (DODAP), N,N-dimethyl-2,3-dioleoyl-oxy)propylamine (DODMA), and N-(1, 2dimyristyloxyprop-3-yl)-N,N-dimethyl-N-hydroxyethyl ammonium bromide (DMRIE).

Additionally, a number of commercial preparations of cationic lipids are available which can be used in the present invention. These include, for example, LIPOFECTIN® (commercially available cationic liposomes comprising DOTMA and 1,2-dioleoyl-sn-3phosphoethanolamine (DOPE), from GIBCO/BRL, Grand Island, N.Y.); LIPOFECTAMINE® (commercially available cationic liposomes comprising N-(1-(2,3dioleyloxy)propyl)-N-(2-(sperminecarboxamido)ethyl)-N,N-dimethylammonium trifluoroacetate (DOSPA) and (DOPE), from GIBCO/BRL); and TRANSFECTAM® (commercially available cationic lipids comprising dioctadecylamidoglycyl carboxyspermine (DOGS) in ethanol from Promega Corp., Madison, WI, USA). The following lipids are cationic and have a positive charge at below physiological pH: DODAP, DODMA, DMDMA, 1,2-dilinoleyloxy-N,N-dimethylaminopropane (DLinDMA), 1,2-dilinolenyloxy-N,N-dimethylaminopropane (DLenDMA).

The further cationic lipid may also be an amino lipid. Representative amino lipids include, but are not limited to, 1,2-dilinoleyoxy-3-(dimethylamino)acetoxypropane (DLin-DAC), 1,2-dilinoleyoxy-3morpholinopropane (DLin-MA), 1,2-dilinoleoyl-3-dimethylaminopropane (DLinDAP), 1,2-dilinoleylthio-3-dimethylaminopropane (DLin-S-DMA), 1-linoleoyl-2-linoleyloxy-3dimethylaminopropane (DLin-2-DMAP), 1,2-dilinoleyloxy-3-trimethylaminopropane chloride salt (DLin-TMA.CI), 1,2-dilinoleoyl-3-trimethylaminopropane chloride salt (DLin-TAP.CI), 1,2-dilinoleyloxy-3-(N-methylpiperazino)propane (DLin-MPZ), 3-(N, Ndilinoleylamino)-1,2-propanediol (DLinAP), 3-(N,N-dioleylamino)-1,2-propanediol (DOAP), 1,2-dilinoleyloxo-3-(2-N,N-dimethylamino)ethoxypropane (DLin-EG-DMA), and 2,2-dilinoleyl-4-dimethylaminomethyl-[1,3]-dioxolane (DLin-K-DMA), 2,2-dilinoleyl-4-(2-dimethylaminoethyl)-

[1,3]-dioxolane (DLin-KC2-DMA); dilinoleyl-methyl-4-dimethylaminobutyrate (DLin-MC3-DMA); MC3 (the information hereon is incorporated by reference from US 2010/0324120).

The amount of the permanently cationic lipid or lipidoid may be selected taking the amount of the RNA cargo into account. In one embodiment, these amounts are selected such as to result in an N/P ratio of the nanoparticle(s) or of the composition in the range from about 0.1 to about 20. In this context, the N/P ratio is defined as the mole ratio of the nitrogen atoms ("N") of the basic nitrogen-containing groups of the lipid or lipidoid to the phosphate groups ("P") of the RNA which is used as cargo. The N/P ratio may be calculated on the basis that, for example, 1 µg RNA typically contains about 3 nmol phosphate residues, provided that the RNA exhibits a statistical distribution of bases. The "N"-value of the lipid or lipidoid may be calculated on the basis of its molecular weight and the relative content of permanently cationic and—if present—cationisable groups.

In certain embodiments, the LNP comprises one or more additional lipids which stabilize the formation of particles during their formation.

Suitable stabilizing lipids include neutral lipids and anionic lipids. The term "neutral lipid" refers to any one of a number of lipid species that exist in either an uncharged or neutral zwitterionic form at physiological pH. Representative neutral lipids include diacylphosphatidylcholines, diacylphosphatidylethanolamines, ceramides, sphingomyelins, dihydro sphingomyelins, cephalins, and cerebrosides. Exemplary neutral lipids include, for example, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1 carboxylate (DOPE-mal), dipalmitoyl phosphatidyl ethanolamine (DPPE), dimyristoylphosphoethanolamine (DMPE), distearoyl-phosphatidylethanolamine (DSPE), 16-O-monomethyl PE, 16-O-dimethyl PE, 18-1-trans PE, 1-stearioyl-2-oleoyl-phosphatidyethanol amine (SOPE), and 1,2-dielaidoyl-sn-glycero-3-phophoethanolamine (transDOPE). In one embodiment, the neutral lipid is 1,2-distearoyl-sn-glycero-3phosphocholine (DSPC).

In some embodiments, the LNPs comprise a neutral lipid selected from DSPC, DPPC, DMPC, DOPC, POPC, DOPE and SM. In various embodiments, the molar ratio of the cationic lipid to the neutral lipid ranges from about 2:1 to about 8:1.

LNP in vivo characteristics and behavior can be modified by addition of a hydrophilic polymer coating, e.g. polyethylene glycol (PEG), to the LNP surface to confer steric stabilization. Furthermore, LNPs can be used for specific targeting by attaching ligands (e.g., antibodies, peptides, and carbohydrates) to its surface or to the terminal end of the attached PEG chains (e.g. via PEGylated lipids).

In some embodiments, the LNPs comprise a polymer conjugated lipid. The term "polymer conjugated lipid" refers to a molecule comprising both a lipid portion and a polymer portion. An example of a polymer conjugated lipid is a PEGylated lipid. The term "PEGylated lipid" refers to a molecule comprising both a lipid portion and a polyethylene glycol portion. PEGylated lipids are known in the art and include 1-(monomethoxy-polyethylene glycol)-2,3-dimyristoylglycerol (PEG-s-DMG) and the like.

In certain embodiments, the LNP comprises an additional, stabilizing-lipid which is a polyethylene glycol-lipid (PEGylated lipid). Suitable polyethylene glycol-lipids include PEG-modified phosphatidylethanolamine, PEG-modified phosphatidic acid, PEG-modified ceramides (e.g., PEG-$CerC_{14}$ or PEG-$CerC_{20}$), PEG-modified dialkylamines, PEG-modified diacylglycerols, PEG-modified dialkylglycerols. Representative polyethylene glycol-lipids include PEG-c-DOMG, PEG-c-DMA, and PEG-s-DMG. In one embodiment, the polyethylene glycol-lipid is N-[(methoxy poly(ethylene glycol)2000)carbamyl]-1,2-dimyristyloxlpropyl-3-amine (PEG-c-DMA). In one embodiment, the polyethylene glycol-lipid is PEG-c-DOMG). In other embodiments, the LNPs comprise a PEGylated diacylglycerol (PEG-DAG) such as 1-(monomethoxy-polyethyleneglycol)-2,3-dimyristoylglycerol (PEG-DMG), a pegylated phosphatidylethanoloamine (PEG-PE), a PEG succinate diacylglycerol (PEG-S-DAG) such as 4-O-(2',3'-di(tetradecanoyloxy)propyl-1-O-(ω-methoxy(polyethoxy)ethyl)butanedioate (PEG-S-DMG), a PEGylated ceramide (PEG-cer), or a PEG dialkoxypropylcarbamate such as ω-methoxy(polyethoxy)ethyl-N-(2,3di(tetradecanoxy)propyl)carbamate or 2,3-di(tetradecanoxy)propyl-N-(ω-methoxy(polyethoxy)ethyl) carbamate. In various embodiments, the molar ratio of the cationic lipid to the PEGylated lipid ranges from about 100:1 to about 25:1.

The total amount of mRNA in the lipid nanoparticles varies and may be defined depending on the mRNA to total lipid w/w ratio. In one embodiment of the invention the invention the mRNA to total lipid ratio is less than 0.06 w/w, preferably between 0.03 and 0.04 w/w.

Therefore, in some embodiments at least one of the one or more RNA molecules is complexed with cationic lipids and/or neutral lipids and thereby form LNPs, preferably PEGylated LNPs.

In preferred embodiments, the RNA molecules in the "complexed RNA" or "RNA-carrier complexes" are formulated together with cationic peptides or proteins, preferably as specified below.

Additionally, preferred cationic or polycationic proteins or peptides may be selected from the following proteins or peptides having the following total formula (I):

$$(Arg)_l(Lys)_m(His)_r(Orn)_o(Xaa)_x, \quad \text{(formula (I))}$$

wherein l+m+r+o+x=7-20, and l, m, r and o are independently selected integers from 0, 1, 2, 3, 4, 5, 6, 7, 8, 9, 10, 11, 12, 13, 14 or 15, provided that the overall content of Arg, Lys, His and Orn represents at least 50% of all amino acids of the oligopeptide; and Xaa may be any amino acid selected from native (=naturally occurring) or non-native amino acids except of Arg, Lys, His or Orn; and x may be an integer selected from 0, 1, 2, 3 or 4, provided, that the overall content of Xaa does not exceed 50% of all amino acids of the oligopeptide according to formula (I). Formula (I) is to be understood as total formula giving the total number of amino acids present and which amino acids are present in the peptide. However, formula (I) is not to be understood as giving any amino acid sequence of the peptide the amino acid sequence of which is variable. Particularly preferred cationic peptides in this context are e.g. $Arg_7$, $Arg_8$, $Arg_9$, $H_3R_9$, $R_9H_3$, $H_3R_9H_3$, $YSSR_9SSY$, $(RKH)_4$, $Y(RKH)_2R$, etc. With respect to cationic or polycationic proteins or peptides, the disclosure of WO 2009/030481 is incorporated herewith by reference.

According to preferred embodiments, the "complexed RNA" or "RNA-carrier complexes" comprises the RNA molecules as defined herein and a polymeric carrier compound. A polymeric carrier compound used according to the invention might be a polymeric carrier compound formed by disulfide-crosslinked cationic compounds. The disulfide-crosslinked cationic compounds may be the same or different from each other. The polymeric carrier compound can also contain further compounds. It is also particularly preferred that the polymeric carrier compound used according to the present invention comprises mixtures of cationic peptides, proteins or polymers and optionally further compounds as defined herein, which are crosslinked by disulfide bonds as described herein. In the context of polymeric carrier compounds, the disclosure of WO 2012/013326 is incorporated herein by reference.

In this context, the cationic compounds, which form basis for the polymeric carrier compounds by disulfide-crosslinkage, are typically selected from any suitable cationic or polycationic peptide, protein or polymer suitable for this purpose, particularly any cationic or polycationic peptide, protein or polymer capable of complexing the RNA molecules as defined herein or a further nucleic acid comprised in the RNA sample, and thereby preferably condensing the RNA molecules or the nucleic acid to form "complexed RNA"/"RNA-carrier complexes". The cationic or polycationic peptide, protein or polymer, is preferably a linear molecule, however, branched cationic or polycationic peptides, proteins or polymers may also be used.

Every disulfide-crosslinking cationic or polycationic protein, peptide or polymer of the polymeric carrier compound, which may be used to complex the RNA molecules according to the invention, contains at least one —SH moiety, most preferably at least one cysteine residue or any further chemical group exhibiting an —SH moiety, capable of forming a disulfide linkage upon condensation with at least one further cationic or polycationic protein, peptide or polymer as cationic component of the polymeric carrier compound as mentioned herein.

As defined above, the polymeric carrier compound, which may be used to complex the RNA molecules may be formed by disulfide-crosslinked cationic (or polycationic) components. Preferably, such cationic or polycationic peptides or proteins or polymers of the polymeric carrier compound, which comprise or are additionally modified to comprise at least one —SH moiety, are selected from, proteins, peptides and polymers as defined herein for carrier compound.

In further embodiments, the polymeric carrier compound which may be used to complex the RNA molecules as defined herein or any further nucleic acid comprised in the (pharmaceutical) RNA sample or vaccine according to the invention may be selected from a polymeric carrier compound according to generic formula (II):

     formula (II)

wherein, $P^1$ and $P^3$ are different or identical to each other and represent a linear or branched hydrophilic polymer chain, each $P^1$ and $P^3$ exhibiting at least one —SH-moiety, capable to form a disulfide linkage upon condensation with component $P^2$, or alternatively with (AA, "AA"=amino acid), $(AA)_q$, or $[(AA)_q]_z$ if such components are used as a linker between $P^1$ and $P^2$ or $P^3$ and $P^2$) and/or with further components (e.g. (AA), $(AA)_q$, $[(AA)_q]_z$ or L), the linear or branched hydrophilic polymer chain selected independent from each other from polyethylene glycol (PEG), poly-N-(2-hydroxy-propyl)methacrylamide, poly-2-(methacryloyloxy)ethyl phosphorylcholines, poly(hydroxyalkyl L-asparagine), poly(2-(methacryloyloxy)ethyl phosphorylcholine), hydroxyethyl starch or poly(hydroxylalkyl L-glutamine), wherein the hydrophilic polymer chain exhibits a molecular weight of about 1 kDa to about 100 kDa, preferably of about 2 kDa to about 25 kDa; or more preferably of about 2 kDa to about 10 kDa, e.g. about 5 kDa to about 25 kDa or 5 kDa to about 10 kDa;

$P^2$ is a cationic or polycationic peptide or protein, e.g. as defined above for the polymeric carrier formed by disulfide-crosslinked cationic components, and preferably having a length of about 3 to about 100 amino acids, more preferably having a length of about 3 to about 50 amino acids, even more preferably having a length of about 3 to about 25 amino acids, e.g. a length of about 3 to 10, 5 to 15, 10 to 20 or 15 to 25 amino acids, more preferably a length of about 5 to about 20 and even more preferably a length of about 10 to about 20; or is a cationic or polycationic polymer, e.g. as defined above for the polymeric carrier formed by disulfide-crosslinked cationic components, typically having a molecular weight of about 0.5 kDa to about 30 kDa, including a molecular weight of about 1 kDa to about 20 kDa, even more preferably of about 1.5 kDa to about 10 kDa, or having a molecular weight of about 0.5 kDa to about 100 kDa, including a molecular weight of about 10 kDa to about 50 kDa, even more preferably of about 10 kDa to about 30 kDa;

each $P^2$ exhibiting at least two —SH-moieties, capable to form a disulfide linkage upon condensation with further components $P^2$ or component(s) $P^1$ and/or $P^3$ or alternatively with further components (e.g. (AA), $(AA)_q$, or $[(AA)_q]_z$);

—S—S— is a (reversible) disulfide bond (the brackets are omitted for better readability), wherein S preferably represents sulphur or a —SH carrying moiety, which has formed a (reversible) disulfide bond. The (reversible) disulfide bond is preferably formed by condensation of —SH-moieties of either components $P^1$ and $P^2$, $P^2$ and $P^2$, or $P^2$ and $P^3$, or optionally of further components as defined herein (e.g. L, (AA), $(AA)_q$, $[(AA)_q]_z$, etc); The —SH-moiety may be part of the structure of these components or added by a modification as defined below;

L is an optional ligand, which may be present or not, and may independently be selected from the other components of formula (II) from the group consisting of RGD, transferrin, folate, a signal peptide or signal sequence, a localization signal or sequence, a nuclear localization signal or sequence (NLS), an antibody, a cell penetrating peptide, (e.g. TAT or KALA), a ligand of a receptor (e.g. cytokines, hormones, growth factors etc.), small molecules (e.g. carbohydrates like mannose or galactose or synthetic ligands), small molecule agonists, inhibitors or antagonists of receptors (e.g. RGD peptidomimetic analogs), and any further protein as defined herein, etc.;

p, z and q are the same or different and are integers independently selected from a range of about 1 to 50, preferably from a range of about 1, 2 or 3 to 30, more preferably from a range of about 1, 2, 3, 4, or 5 to 25, or a range of about 1, 2, 3, 4, or 5 to 20, or a range of about 1, 2, 3, 4, or 5 to 15, or a range of about 1, 2, 3, 4, or 5 to 10, including e.g. a range of about 4 to 9, 4 to 10, 3 to 20, 4 to 20, 5 to 20, or 10 to 20, or a range of about 3 to 15, 4 to 15, 5 to 15, or 10 to 15, or a range of about 6 to 11 or 7 to 10. Most preferably, p, z and q are independently selected from a range of about 1, 2, 3, 4, or 5 to 10, more preferably in a range of about 1, 2, 3, or 4 to 9, in a range of about 1, 2, 3, or 4 to 8, or in a range of about 1, 2, or 3 to 7.

In the context of polymeric carrier compounds, the disclosure of WO 2011/026641 is incorporated herein by reference. Each of hydrophilic polymers $P^1$ and $P^3$ typically exhibits at least one —SH-moiety, wherein the at least one —SH-moiety is capable to form a disulfide linkage upon reaction with component $P^2$ or with component (AA) or $(AA)_q$, if used as linker between $P^1$ and $P^2$ or $P^3$ and $P^2$ as defined below and optionally with a further component, e.g. L and/or (AA) or $(AA)_q$, e.g. if two or more —SH-moieties are contained. The following subformulae "$P^1$-S—S—$P^2$" and "$P^2$-S—S—$P^3$" within generic formula (II) above (the brackets are omitted for better readability), wherein any of S, $P^1$ and $P^3$ are as defined hereinabove, typically represent a situation, wherein one-SH-moiety of hydrophilic polymers $P^1$ and $P^3$ was condensed with one —SH-moiety of component $P^2$ of generic formula (II) above, wherein both sulphurs of these —SH-moieties form a disulfide bond —S—S— as defined herein in formula (II). These —SH-moieties are typically provided by each of the hydrophilic polymers $P^1$ and $P^3$, e.g. via an internal cysteine or any further (modified) amino acid or compound which carries a —SH moiety. Accordingly, the subformulae "$P^1$-S—S—$P^2$" and "$P^2$-S—S—$P^3$" may also be written as "$P^1$-Cys-Cys-$P^2$" and "$P^2$-Cys-Cys-$P^3$", if the —SH— moiety is provided by a cysteine, wherein the term Cys-Cys represents two cysteines coupled via a disulfide bond, not via a peptide bond. In this case, the term "—S—S—" in these formulae may also be written as "—S-Cys", as "-Cys-S" or as "-Cys-Cys-". In this context, the term "-Cys-Cys-" does not represent a peptide bond but a linkage of two cysteines via their —SH-moieties to form a disulfide bond. Accordingly, the term "-Cys-Cys-" also may be understood generally as "-(Cys-S)-(S-Cys)-", wherein in this specific case S indicates the sulphur of the —SH-moiety of cysteine. Likewise, the terms "-S-Cys" and "—Cys-S" indicate a disulfide bond between a —SH containing moiety and a cysteine, which may also be written as "-S-(S-Cys)" and "-(Cys-S)-S". Alternatively, the hydrophilic polymers $P^1$ and $P^3$ may be modified with a —SH moiety, preferably via a chemical reaction with a compound carrying a —SH moiety, such that each of the hydrophilic polymers $P^1$ and $P^3$ carries at least one such —SH moiety. Such a compound carrying a —SH moiety may be e.g. an (additional) cysteine or any further (modified) amino acid, which carries a —SH moiety. Such a compound may also be any non-amino compound or moiety, which contains or allows to introduce a —SH moiety into hydrophilic polymers $P^1$ and $P^3$ as defined herein. Such non-amino compounds may be attached to the hydrophilic polymers $P^1$ and $P^3$ of formula (II) of the polymeric carrier compound according to the present invention via chemical reactions or binding of compounds, e.g. by binding of a 3-thio propionic acid or thioimolane, by amide formation (e.g. carboxylic acids, sulphonic acids, amines, etc), by Michael addition (e.g maleinimide moieties, α,β-unsatured carbonyls, etc), by click chemistry (e.g. azides or alkines), by alkene/alkine methatesis (e.g. alkenes or alkines), imine or hydrozone formation (aldehydes or ketons, hydrazins, hydroxylamins, amines), complexation reactions (avidin, biotin, protein G) or components which allow Sn-type substitution reactions (e.g halogenalkans, thiols, alcohols, amines, hydrazines, hydrazides, sulphonic acid esters, oxyphosphonium salts) or other chemical moieties which can be utilized in the attachment of further components. A particularly preferred PEG derivate in this context is alpha-Methoxy-omega-mercapto poly(ethylene glycol). In each case, the SH-moiety, e.g. of a cysteine or of any further (modified) amino acid or compound, may be present at the terminal ends or internally at any position of hydrophilic polymers $P^1$ and $P^3$. As defined herein, each of hydrophilic polymers $P^1$ and $P^3$ typically exhibits at least one —SH-moiety preferably at one terminal end, but may also contain two or even more —SH-moieties, which may be used to additionally attach further components as defined herein, preferably further functional peptides or proteins e.g. a ligand, an amino acid component (AA) or $(AA)_q$, antibodies, cell penetrating peptides or enhancer peptides (e.g. TAT, KALA), etc.

The "complexed RNA"/"RNA-carrier complex" according to the present invention, is preferably prepared according to a first step by complexing the RNA molecules according to the invention with a carrier compound, e.g. with a cationic or polycationic compound and/or with a polymeric carrier, preferably as defined herein, in a specific ratio to form a stable complex. In this context, it is highly preferable, that no free cationic or polycationic compound or polymeric carrier compound or only a negligibly small amount thereof remains in the RNA sample comprising the RNA-carrier complexes after complexing the RNA molecules. Accordingly, the ratio of the RNA molecules and the cationic or polycationic carrier compound and/or the polymeric carrier compound in the complex of the RNA-carrier complexes is typically in a range so that the RNA molecules are entirely complexed and no free or non-complexed cationic or polycationic carrier compound or polymeric carrier compound or only a negligibly small amount thereof remains in the RNA sample.

Preferably, the ratio of the RNA molecules as defined herein to the cationic or polycationic carrier compound and/or the polymeric carrier compound, as defined herein, is selected from a range of about 6:1 (w/w) to about 0.25:1 (w/w), more preferably from about 5:1 (w/w) to about 0.5:1 (w/w), even more preferably of about 4:1 (w/w) to about 1:1 (w/w) or of about 3:1 (w/w) to about 1:1 (w/w), and most preferably a ratio of about 3:1 (w/w) to about 2:1 (w/w). Alternatively, the ratio of the RNA molecules as defined herein to the cationic or polycationic carrier compound and/or the polymeric carrier compound, preferably as defined herein, in the carrier compound part of the RNA-carrier complexes, may also be calculated on the basis of the nitrogen/phosphate ratio (N/P-ratio) of the entire complex. In the context of the present invention, the N/P-ratio is preferably in the range of about 0.1-10, preferably in a range of about 0.3-4 and most preferably in a range of about 0.5-2 or 0.7-2 regarding the ratio of RNA molecules: cationic or polycationic carrier compound and/or polymeric carrier compound, preferably as defined herein, in the complex, and most preferably in a range of about 0.7-1.5, 0.5-1 or 0.7-1, and even most preferably in a range of about 0.3-0.9 or 0.5-0.9, preferably provided that the cationic or polycationic carrier compound in the RNA-carrier complex is a cationic or polycationic cationic or polycationic protein or peptide and/or the polymeric carrier compound as defined above.

According to further particularly preferred embodiments, cationic or polycationic peptides or proteins used to complex the RNA molecules, according to formula (I) as shown above and which comprise or are additionally modified to comprise at least one —SH moiety, may be, without being restricted thereto, selected from the subgroup consisting of generic formulae $Arg_7$ (also termed as $R_7$), $Arg_9$ (also termed Re), $Arg_{12}$ (also termed as $R_{12}$) etc.

According to further particularly preferred embodiments, the cationic or polycationic peptide or protein of the polymeric carrier compound, when defined according to formula {(Arg)$_l$(Lys)$_m$(His)$_r$(Orn)$_o$(Xaa)$_x$} (formula (I)) as shown above, and which comprise or are additionally modified to comprise at least one —SH moiety, may be, without being restricted thereto, selected from subformula (III):

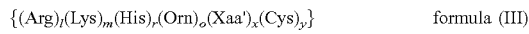

{(Arg)$_l$(Lys)$_m$(His)$_r$(Orn)$_o$(Xaa')$_x$(Cys)$_y$}    formula (III)

wherein (Arg)$_l$(Lys)$_m$(His)$_r$(Orn)$_o$ and x are as defined herein, Xaa' is any amino acid selected from native (=naturally occurring) or non-native amino acids except of Arg, Lys, His, Orn or Cys and y is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80 and 81-90, provided that the overall content of Arg (Arginine), Lys (Lysine), His (Histidine) and Orn (Ornithine) represents at least 10% of all amino acids of the oligopeptide.

This embodiment may apply to situations, wherein the cationic or polycationic peptide or protein of the polymeric carrier, e.g. when defined according to empirical formula {(Arg)$_l$(Lys)$_m$(His)$_r$(Orn)$_o$(Xaa)$_x$} (formula (I)) as shown above, comprises or has been modified with at least one cysteine as —SH moiety in the above meaning (expressed by formula (III)) such that the cationic or polycationic peptide as cationic carrier component comprises at least one cysteine, which is capable to form a disulfide bond with other components of the polymeric carrier compound. Examples may comprise any of the following sequences:

Cys(Arg$_7$) (SEQ ID NO: 17), Cys(Arg$_8$) (SEQ ID NO: 18), Cys(Arg$_9$) (SEQ ID NO: 19), Cys(Arg$_{10}$) (SEQ ID NO: 20), Cys(Arg$_{11}$) (SEQ ID NO: 21), Cys(Arg$_{12}$) (SEQ ID NO: 22), Cys(Arg$_{13}$) (SEQ ID NO: 23), Cys(Arg$_{14}$) (SEQ ID NO: 24), Cys(Arg$_{15}$) (SEQ ID NO: 25), Cys(Arg$_{16}$) (SEQ ID NO: 26), Cys(Arg$_{17}$) (SEQ ID NO: 27), Cys(Arg$_{18}$) (SEQ ID NO: 28), Cys(Arg$_{11}$) (SEQ ID NO: 29), Cys(Arg$_{20}$) (SEQ ID NO: 30).

According to another particularly preferred embodiment, the cationic or polycationic peptide or protein of the polymeric carrier compound, when defined according to formula {(Arg)$_l$;(Lys)$_m$;(His)$_r$;(Orn)$_o$;(Xaa)$_x$} (formula (I)) as shown above, may be, without being restricted thereto, selected from subformula (IV):

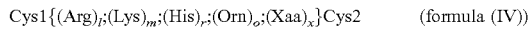

Cys1{(Arg)$_l$;(Lys)$_m$;(His)$_r$;(Orn)$_o$;(Xaa)$_x$}Cys2    (formula (IV))

wherein empirical formula {(Arg)$_l$;(Lys)$_m$;(His)$_r$;(Orn)$_o$; (Xaa)$_x$} (formula (I)) is as defined herein and forms a core of an amino acid sequence according to (semiempirical) formula (IV) and wherein Cys1 and Cys2 are flanking cysteines proximal to, or terminal to (Arg)$_l$;(Lys)$_m$;(His)$_r$; (Orn)$_o$;(Xaa)$_x$. Examples may comprise any of the above sequences flanked by two Cys and following sequences:

Cys(Arg$_7$)Cys (SEQ ID NO: 31), Cys(Arg$_8$)Cys (SEQ ID NO: 32), Cys(Arg$_9$)Cys (SEQ ID NO: 33), Cys(Arg$_{10}$)Cys (SEQ ID NO: 34), Cys(Arg$_{11}$)Cys (SEQ ID NO: 35), Cys(Arg$_{12}$)Cys (SEQ ID NO: 36), Cys(Arg$_{13}$)Cys (SEQ ID NO: 37), Cys(Arg$_{14}$)Cys (SEQ ID NO: 38), Cys(Arg$_{15}$)Cys (SEQ ID NO: 39), Cys(Arg$_{16}$)Cys (SEQ ID NO: 40), Cys(Arg$_{17}$)Cys (SEQ ID NO: 41), Cys(Arg$_{18}$)Cys (SEQ ID NO: 42), Cys(Arg$_{19}$)Cys (SEQ ID NO: 43), Cys(Arg$_{20}$)Cys (SEQ ID NO: 44).

This embodiment is useful in situations, wherein the cationic or polycationic peptide or protein of the polymeric carrier, e.g. when defined according to empirical formula (Arg)$_l$(Lys)$_m$(His)$_r$(Orn)$_o$(Xaa)$_x$ (formula (I)) as shown above, has been modified with at least two cysteines as —SH moieties in the above meaning such that the cationic or polycationic peptide of the inventive polymeric carrier compound as cationic carrier compound carries at least two (terminal) cysteines, which are capable to form a disulfide bond with other compounds of the polymeric carrier compounds.

In preferred embodiments, the polymeric carrier compound is formed by, comprises or consists of the peptide CysArg$_{12}$Cys (CRRRRRRRRRRRRC; SEQ ID NO: 36) or CysArg$_{12}$ (CRRRRRRRRRRRR; SEQ ID NO: 22).

In embodiments where the complexed RNA is complexed with cationic or polycationic peptides or proteins as the carrier compound the nitrogen/phosphate ratio of the complexed RNA ranges from about 0.1 to about 20, or from about 0.2 to about 15, or from about 2 to about 15, or from about 2 to about 12, wherein the N/P ratio is defined as the mole ratio of the nitrogen atoms of the basic groups of the cationic peptide or polymer to the phosphate groups of the RNA.

In another preferred embodiment, the at least one of the one or more coding RNA molecules (the complexed RNA molecule) is complexed with one or more cationic or polycationic peptides, wherein the cationic or polycationic peptide is preferably protamine. More preferably, the complexed RNA is complexed with protamine by addition of protamine-trehalose solution to the RNA sample at a RNA:protamine weight to weight ratio of 2:1.

In a specific embodiment, the complexed RNA molecules are complexed with a polymer (e.g., a polymeric carrier compound as defined herein) comprising HO-PEG5000-S-(S-CHHHHHHRRRRHHHHHHC-S-)$_7$-S-PEG5000-OH (CHHHHHHRRRRHHHHHHC is exemplarily depicted in SEQ ID NO: 45), wherein PEG5000 denotes a polyethylene glycol (PEG) moiety having a molecular weight of approx. 5,000 Da.

If the carrier compound comprises PEG, the molecular weight of the PEG moiety may be selected from the range of 500 to 100,000 Da, more preferably of 1,000 to 50,000 Da, even more preferably from 2,000 to 10,000 Da and most preferably of 4,000 to 6,000 Da.

For analyzing an RNA sample comprising complexed RNA molecules, i.e. RNA-carrier complexes, the inventive method may comprise further steps prior to step a) in which the RNA sample is prepared for the quality control analysis. To remove RNA molecules which are not properly complexed or e.g. encapsulated in a liposome or LNP, but bound to the surface of the RNA-carrier complex or of an RNA molecule free carrier complex, the method further comprises prior to step a) a step of d) contacting the RNA sample with salt ("high salt treatment step") to release RNA molecules which are bound to the surface of the RNA-carrier complex. After step d) the RNA sample may contain RNA molecules which are present in complexed form (=bound in RNA-carrier complexes) and free RNA molecules. The population of free RNA molecules is made up of RNA molecules which were bound to the surface of the carrier compound complexes prior to step d) and of RNA molecules which never bound to the carrier complexes. Based on this, it is possible to obtain a quality control parameter on the complexed RNA molecule sample.

Hence, the present invention also relates to a method for quality control analysis of an RNA sample comprising free RNA molecules and complexed RNA molecules belonging to n different RNA molecules, thereby determining at least one quality parameter as defined above.

A suitable salt for performing this "high salt treatment step" may be NaCl. The salt, preferably NaCl, may be used in a range from 500 mM to 5 M, preferably from 1 M to 5

M, more preferably from 0.75 M to 3 M, most preferably NaCl is used in a concentration of about 1 to 2 M. If protamine is present, 1.5 M NaCl is a suitable concentration. The step of dissociating the complexed RNA may additionally require the incubation at elevated temperatures.

A suitable temperature for the dissociation step may be at about 60° C. to 95° C., preferably at about 70° C. to 90° C., more preferably at about 80° C. to 90° C., most preferably at about 85° C.

To remove free RNA molecules in the RNA samples, the method further comprises prior to step a) and, if present, after step d), a step of
- e) contacting the RNA sample with at least one ribonuclease (RNase) under conditions suitable for said at least one ribonuclease to degrade RNA molecules which are not present in complexed form, and/or
- f) subjecting the RNA sample to a method selected from the group consisting of gel filtration chromatography, molecular weight cut-off filtration, ultracentrifugation, and combinations thereof, to remove RNA molecules which are not present in complexed form.

The RNase may be selected from the group consisting of RNase A, RNase T1, RNase I and combinations thereof.

The method may also comprise after step e) and prior to step a) a step of ee) inactivating the ribonuclease. Optionally, step ee) employs one or more members selected from the group consisting of RNase inhibitors, uridine 2',3'-cyclic vanadate, 5'-diphosphoadenosine 3'-phophate, 5'-diphosphoadenosine 2'-phophate, diethyl pyrocarbonate, guanidinium thiocyanate, 2-mercaptoethanol, heavy metal ions, mononucleotides, e.g. 2'-GMP or 3'-GMP, guanilyl-2',5'-guanosine, SDS, and combinations thereof.

For analysis purposes, the RNA-carrier complexes may be partitioned and specifically selected prior to step a) and thus prior to steps b) and c). "partitioning" and "partitioned" in the sense of the present invention is to be understood as a method step to separate single RNA-carrier complexes and/or group a specific number of RNA-carrier complexes, e.g. 50 RNA-carrier complexes. Partitioning may be useful for quality control of a single RNA-carrier complex to check quantity, integrity, presence and quantitative ratio of the complexed RNA molecules in the specific single RNA-carrier complex or, if a defined number of RNA-carrier complexes is partitioned, of the group of selected, i.e. partitioned, RNA-carrier complexes. For example, 1, 3, 4, 5, 6, 7, 8, 9, 10, 12, 15, 17, 20, 25, 30, 35, 40, 45, 50, 55, 60, 75, 80, 100, 125, 150 or more RNA-carrier complexes may be partitioned to be analyzed together. The inventive method thus, further comprises prior to step a) and, if present, after any one of steps d), e), f), and/or ee), a step of g) partitioning of the RNA-carrier complexes.

In a preferred embodiment, partitioning is performed using a fluorescence activated cell sorting (FACS, e.g. a FACSCanto II (BD Biosciences, Franklin Lakes, NJ, USA) based assay and/or using acoustic liquid handling according to the manufacturer's instructions. Examples of acoustic liquid handlers are Echo® Liquid Handler, such as Echo® 555 Liquid Handler (LabCyte Inc., Sunnyvale, CA, USA) or an ATS Acoustic Liquid Dispenser (EDC Biosystems, Fremont, CA, USA). Moreover, the FACS based assay comprises contacting the RNA-carrier complexes with an antibody and/or a fluorescent probe. Preferably, the antibody binds to the RNA-carrier complex and is labelled with a detectable probe, such as a fluorescent probe. Alternatively, a secondary antibody being directed to a first antibody is used which is labelled with a detectable probe, such as a fluorescent probe. If a positive (fluorescence) signal is detected, the respective RNA-carrier complex is separated i.e. partitioned.

In a particularly preferred embodiment, the RNA-carrier complex comprises PEG. In this case, it is possible to separate the RNA-carrier complexes by contacting the RNA-carrier complexes with a first anti-PEG antibody and/or a secondary antibody comprising a fluorescent probe, preferably in combination with FACS.

The partitioned RNA-carrier complexes are preferably partitioned onto a target plate, more preferably onto a target (dd)PCR compatible plate, and analysed according to the method described herein, subsequently.

After partitioning, the RNA-carrier complexes are either separated into single RNA-carrier complexes, i.e. a single RNA-carrier complex per well on a target plate or similar (single RNA-carrier complex analysis), or a specific number of, such as 50, RNA-carrier complexes are grouped together in a single well on a target plate (group RNA-carrier complex analysis). In both cases, the RNA molecules need to be released from the carrier compound for further analysis according to the inventive method, such as in steps a), a1), b) and c).

To release the complexed RNA molecules from the RNA-carrier-complexes for subsequent quality control analysis, prior to step a) or a1) and, if present, after any one of steps d), e), f), ee), and/or g), a step of h) contacting the RNA sample with a detergent, heparin, SDS, and/or salt (e.g. high salt treatment as described above) to release the at least one of the one or more coding RNA molecules which is present in complexed form in the RNA-carrier complexes, and/or a step i) of capturing the released one or more coding RNA molecules.

In embodiments where cationic or polycationic peptides or proteins are used for complexation of the RNA, the dissociation step may be performed by a high salt treatment as explained above, SDS treatment, or heparin treatment.

In embodiments where lipids are used for complexation of the RNA (e.g. LNP encapsulation), the dissociation step may be performed by detergent treatment (Triton X-100, Tween-20) e.g. using 1%-5% TritonX100, preferably 2% TritonX100.

Released RNA may be captured in an optional step i) using common methods known in the art prior to cDNA synthesis. Preferably, Agencourt® AMPure® XP beads (Beckman Coulter, Brea, CA, USA) are used to capture the released RNA.

In embodiments, where one or more single RNA-carrier complexes are analyzed per well on a target plate, the released RNA molecules from the RNA-carrier complex are preferably analyzed according to step b3). For this purpose, the RNA sample containing the RNA molecules released from the RNA-carrier complexes is divided by the number of RNA molecule species to be analyzed and each RNA molecule species is analyzed in a separate reaction vessel. In this case, the same or different detectable probes may be used. In embodiments, where a group of RNA-carrier complexes is analyzed per well on a target plate, analysis is preferably performed in a single reaction vessel for all RNA molecule species. In this case, for each RNA molecule species to be analyzed a different detectable probe should be used.

EXAMPLES

The following examples are intended to illustrate the invention in a further way. They are merely illustrative and not intended to limit the subject matter of the invention.

Example 1: Preparation of DNA Encoding Haemagglutinin (HA) Proteins of Several Serotypes For the present examples, DNA sequences encoding different haemagglutinin proteins, a glycoprotein found on the surface of influenza viruses (Influenza A and Influenza B), were generated. HA proteins of various serotypes were used (see Table 1 below). The DNA sequences were prepared by modifying the wild type encoding DNA sequence by introducing a GC-optimized sequence for stabilization. Sequences were introduced into the same vector backbone, a pUC19 derived vector and modified to comprise a 5'-UTR derived from the 32L4 ribosomal protein (32L4 TOP 5'-UTR) and a 3'-UTR derived from albumin, a histone-stem-loop structure, and a stretch of 64 adenosines at the 3'-terminal end. The RNA sequences as well as the plasmid DNA sequences are provided in the sequence protocol (SEQ ID NOs: 1-8).

TABLE 1

HA-constructs used in the experiments

| HA protein description | SEQ ID NO Plasmid DNA | SEQ ID NO RNA |
|---|---|---|
| HA Influenza A (California) | 1 | 5 |
| HA Influenza B (Brisbane) | 2 | 6 |
| HA Influenza B (Phuket) | 3 | 7 |
| HA Influenza A (Hongkong) | 4 | 8 |

If not stated otherwise, the DNA plasmids obtained in Example 1 were linearized using EcoRI and transcribed in vitro using DNA dependent T7 RNA polymerase in the presence of a nucleotide mixture under respective buffer conditions. The obtained mRNAs were purified using PureMessenger® as described in WO 2008/077592 A1.

Example 2: RT-ddPCR to Identify One RNA Molecule Species in a Sample Comprising Four RNA Molecule Species Droplet digital PCR (ddPCR) measures absolute quantities by counting nucleic acid molecules encapsulated in discrete, volumetrically defined water-in-oil droplet partitions. A ddPCR reaction is divided into around 20,000 droplets that either contain or not contain template leading to PCR positive and negative droplets that are counted allowing for quantitation of template concentration using Poisson distribution algorithm. ddPCR enables more precise absolute quantification as compared to relative quantitation (qPCR) which is limited due to the doubling during each cycle.

2.1 Generation of an RNA Sample with RNA Molecules Belonging to Four Different RNA Molecule Species Coding for Four Different HA Antigens Four plasmid DNA constructs (SEQ ID NOs 1-4) harboring four different antigens were used as a template for PCR amplification, using a standard PCR program commonly known in the art. Obtained PCR-products were purified using common protocols known in the art. Purified PCR products were used as a template for DNA dependent RNA in vitro transcription using T7 RNA polymerase in the presence of a nucleotide mixture and a cap analogue under respective buffer conditions. The obtained mRNAs were purified as described in WO 2008/077592 A1.

2.2 Reverse Transcription (RT) of an mRNA-Mixture to Obtain a cDNA-Mixture Using M-MLV RT Four different RNAs (=RNA molecules of four different RNA molecule species) of example 2.1 (SEQ ID NOs: 5-8) were adjusted to a concentration of 50 ng/μl and mixed equimolar. In separate reactions, 5 μl of the RNA mixture were added to 8 μl Oligo(dT)-dNTP-mix (volumes for a single reaction: 1 μl Oligo $(dT)_{12-18}$ primer (50 μM)+1 μl random hexamer primer+1 μl dNTP mix (10 mM)+5 μl RNase/DNase free water). The reaction was incubated at 65° C. for 5 min and placed on ice for 1 min. Then 7 μl of RT buffer (volumes for a single reaction: 4 μl First Strand Buffer (5λ)+2 μl DTT (0.1 M)+1 μl RNaseOUT™ (40 U/μl)) was added. The reaction mix was gently mixed followed by a brief centrifugation step to spin down the solution. After an incubation step of 2 min at 37° C., 1 μl M-MLV (Moloney Murine Leukemia Virus) reverse transcriptase (M-MLV RT) was added. The reverse transcription reaction was performed at 37° C. for 50 min and terminated at 70° C. for 15 min. After a short incubation step on ice followed by a brief centrifugation to spin down the solution, 1 μl RNase H was added and incubated for 20 min at 37° C.

2.3 Droplet Digital PCR (ddPCR) to Identify One Target-cDNA

The obtained cDNA mixture was diluted into a copy range of 1,000-1,500 copies per μl in a master mix consisting of QX200 ddPCR EvaGreen® Supermix diluted to 1× using WFI. The master mix was then aliquoted and respective specific primers (see Table 2 below) were added to a final concentration of 100 nM. The setup for a 1× ddPCR reaction is shown in Table 3.

TABLE 2

Specific primer pairs used for PCR amplification and ddPCR amplification

| Target | SEQ ID NO | Name | Sequence |
|---|---|---|---|
| HA Influenza B (Brisbane) | 9 | R2361-1-F | TCGCCATCTTCGTGGTGTA |
| HA Influenza B (Brisbane) | 10 | 3'UTR-1-R | CCATCGGGCTAGTCAGTCTTAT |
| HA Influenza B (Pukhet) | 11 | R4904-1-F | CACCATCCTGCTGTACTACTC |
| HA Influenza B (Pukhet) | 12 | 3'UTR-1-R | CCATCGGGCTAGTCAGTCTTAT |
| HA Influenza A (Hongkong) | 13 | R4936-1-F | CTGCTGGGCTTCATCATGT |
| HA Influenza A (Hongkong) | 14 | 3'UTR-1-R | CCATCGGGCTAGTCAGTCTTAT |
| HA Influenza A (California) | 15 | R5218-1-F | CTACCAGATCCTGGCGATCTAC |
| HA Influenza A (California) | 16 | 3'UTR-1-R | CCATCGGGCTAGTCAGTCTTAT |

TABLE 3

Set up of 1x ddPCR reaction

| | |
|---|---|
| 2x QX200 ddPCR EvaGreen ® Supermix (µl) | 11 µl |
| WFI (µl) | 4.4 µl |
| Forward primer (1 µM stock) (µl) | 2.2 µl |
| Reverse primer (1 µM stock) (µl) | 2.2 µl |
| Template (10,000 copies/µl) (µl) | 2.2 µl |
| Total (µl) | 22 µl |

From the master mix, 17.6 µl were combined with 2.2 µl of forward and 2.2 µl of reverse primer (1 µM) per reaction to yield a volume of 22 µl. Then 20 µl were transferred to a droplet generator cartridge followed by 70 µl droplet generator oil in the corresponding well. The cartridge was placed into a droplet generator and the produced droplets were transferred to a PCR plate. PCR was performed under conditions shown in Table 4. After PCR was complete, the plate was placed into a QX200™ droplet reader to analyze the fluorescence signals of droplets. Copy number was determined using QuantaSoft™ (BioRad).

TABLE 4 ddPCR Conditions

| Cycling Step | Temp (° C.) | Time | Ramp Rate | Number of cycles |
|---|---|---|---|---|
| Enzyme activation | 95 | 5 min | 2° C./sec | 1 |
| Denaturation | 95 | 30 sec | | 40 |
| Annealing + extension | 60 | 1 min | | 40 |
| Signal stabilization | 4 | 5 min | | 1 |
| | 90 | 5 min | | 1 |
| Hold | 4 | infinite | | 1 |

2.4 Results

Figure 2:
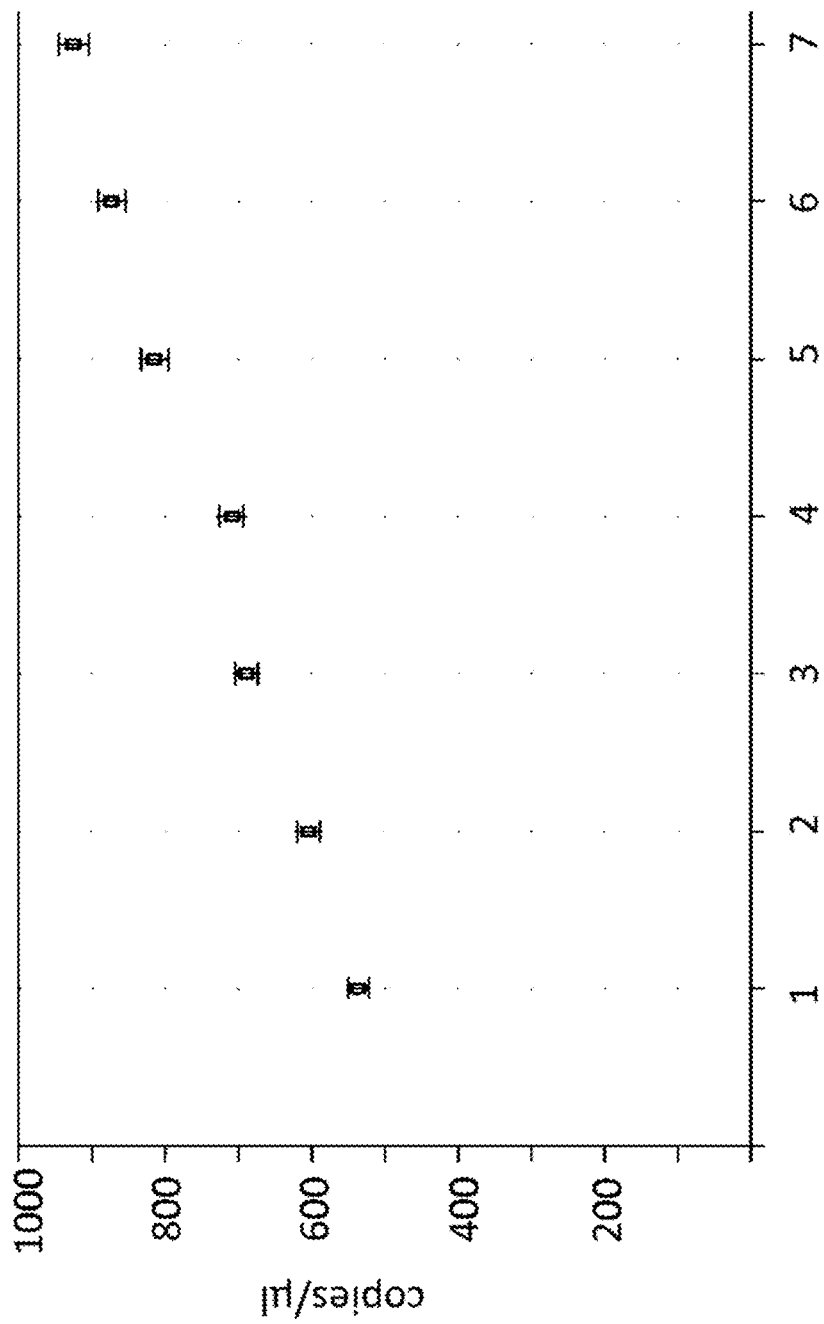
FIG. 2: Precision of cDNA measurements within an mRNA mixture. The measured values represent the concentrations of target cDNA in copies/µL of each sample 1 to 7. Measurements correlate linearly with the target cDNA dilution. All reactions were single measurements and error bars are calculated from the Poisson error. A detailed description of the experiment is provided in Example 2.

The results of FIG. 1 show that using ddPCR, a target cDNA of interest can be amplified specifically within a mix of four different cDNA species using target specific primers. Furthermore, as shown in FIG. 2 ddPCR is a robust tool to determine the concentration of one target cDNA in a mix of four different cDNA species precisely. The specific primer pairs were used to perform the analysis of four RNA species in a mixture of four similar RNA species (see Example 3). The results suggest that RT-ddPCR is a robust method to analyze different RNA species in an RNA mixture in terms of presence and quantity.

Example 3: RT-ddPCR to Identify Four RNA Molecule Species in a Mixture of Four RNA Molecule Species To evaluate the specific presence and quantity for each individual RNA molecule species within an RNA mixture of four different RNA molecule species (SEQ ID NOs: 5-8), RT-ddPCR was performed on RNA mixtures generated according to Example 2.1.

3.1. Reverse Transcription of an mRNA-Mixture to Obtain a cDNA-Mixture Using Superscript IV VILO For the reverse transcription of 2 ng mRNA mixture (4 different HA mRNAs), the RNA mixture was incubated with SuperScript® IV VILO master mix (Thermo Fisher, Waltham, MA, USA) and incubated at 25° C. for 10 minutes, 50° C. for 10 minutes and 85° C. for 5 minutes according to the manufacturer's protocol.

3.2. Droplet Digital PCR (ddPCR) to Identify Each Target-cDNA in a Mixture

Four separate ddPCR reactions were performed on the obtained cDNA mixture using unique primer pairs for each of the four cDNA species (see Table 2). The ddPCR reactions were performed essentially as described in Example 2.3. After ddPCR reactions were complete, the plate was placed into a QX200™ droplet reader to analyze the fluorescence signals of droplets. Copy number for each target cDNA and presence were determined using QuantaSoft™ (BioRad, Hercules, CA, USA).

Figure 3:
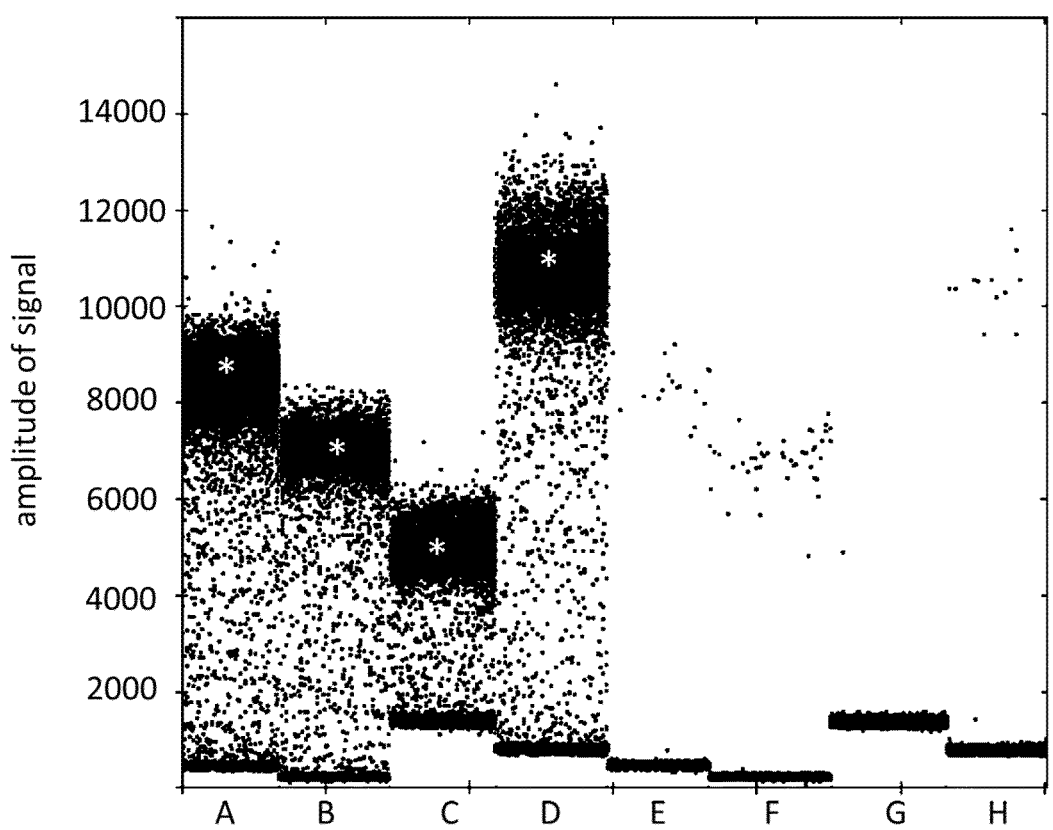
FIG. 3: ddPCR 1-D-plot of specificity testing of primer combinations specific for the respective cDNAs. A-D show the positive signals of primer combinations for RNAs HA Influenza B (Brisbane) (A), HA Influenza B (Pukhet) (B), HA Influenza A (Hongkong) (C), HA Influenza A (California) (D), respectively, detecting the target cDNA in a mix of all four cDNAs. E-H show the results using the same primer combinations as A-D, respectively. However, samples E-H contained all cDNAs except the target one. Sample E contained all cDNAs except HA Influenza B (Brisbane), sample F contained all cDNAs except HA Influenza B (Pukhet), sample G contained all cDNAs except HA Influenza A (Hongkong) and sample H contained all cDNAs except HA Influenza A (California). The ratio of positive droplets (black, thick bands between 4000 and 12000 amplitude of signal; indicated by asterisks) to negative droplets (black bands below 2000) is then converted to target copies per µL reaction using Poisson's distribution algorithm. A detailed description of the experiment is provided in Example 3.

To additionally test the specificity of the primers for their target cDNA, a mix including all but the target cDNA were analyzed using ddPCR (FIG. 3).

Figure 4:
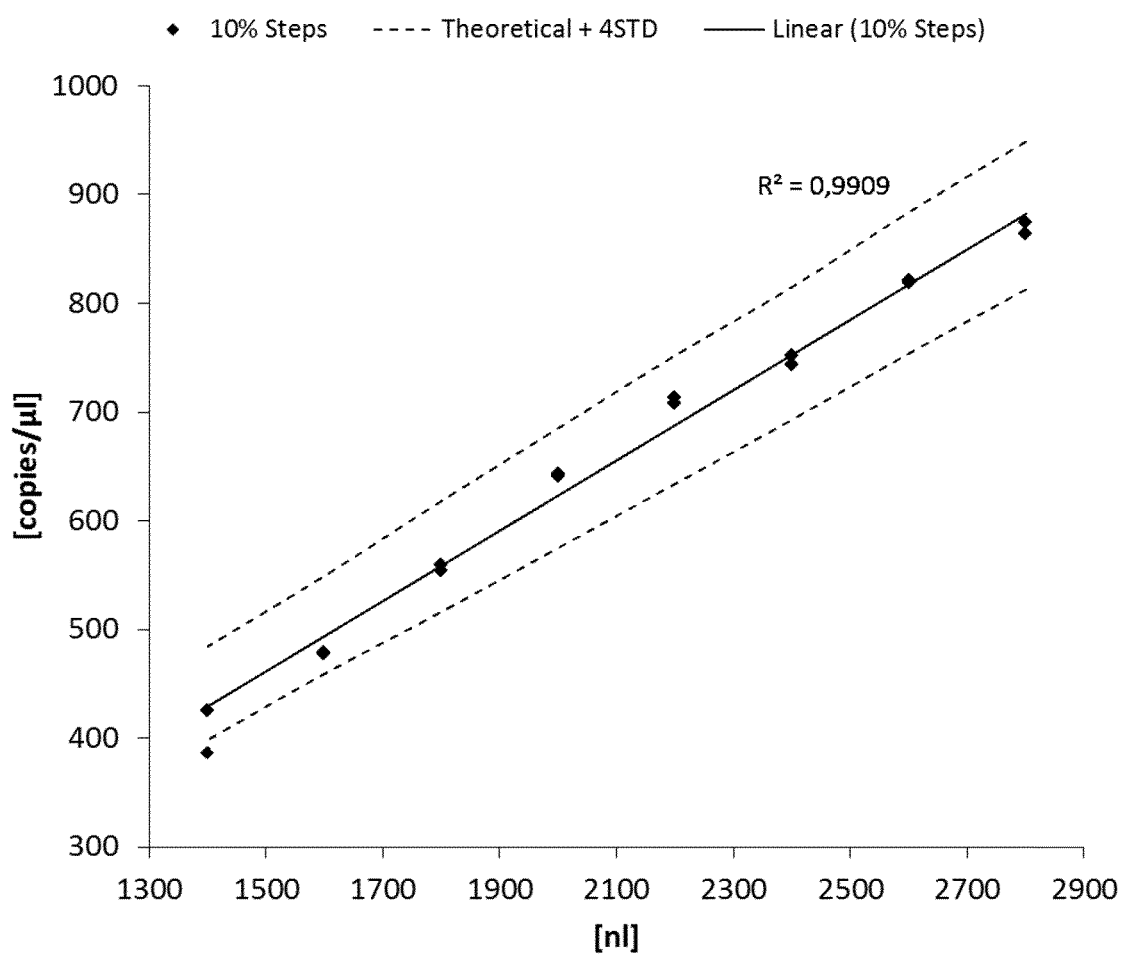
FIG. 4: Precision of cDNA measurements within an mRNA mixture. The measured values represent the concentrations of target cDNA in copies/µL in relation to the volume of the cDNA sample used for dPCR. The measurements correlate linearly with the set-up cDNA dilutions (measured copies/µL and are within standard deviation indicated by dashed lines). All reactions were performed in duplicates. A detailed description of the experiment is provided in Example 3.

To test the precision of the system, the ddPCR was performed on mixes that contained three non-target cDNA at constant concentration (1.0) and one respective target cDNA at concentrations varying in 10% difference steps (0.7-1.3) (FIG. 4).

Figure 5:
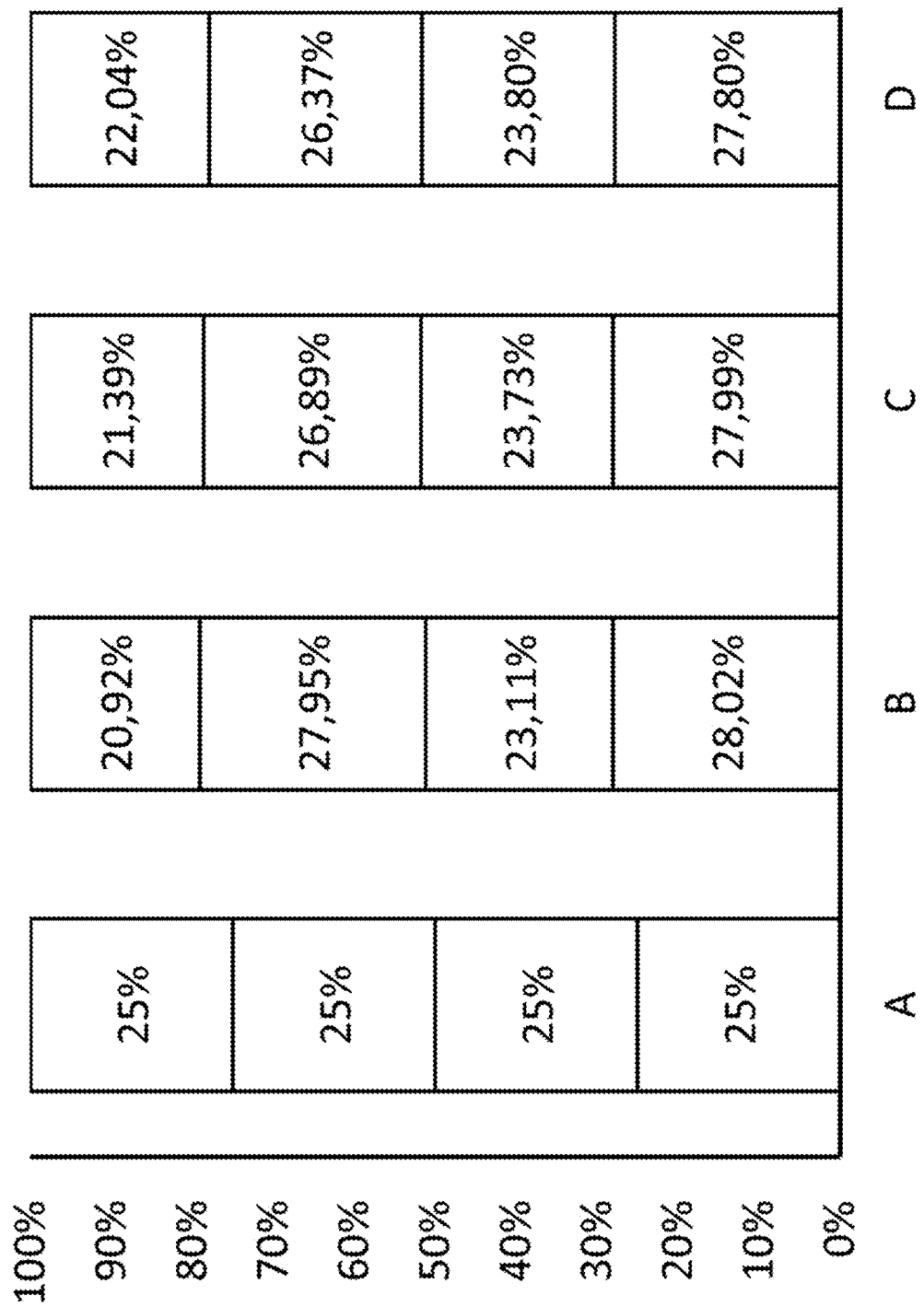
FIG. 5: Robustness of cDNA measurements of an mRNA mixture, i.e. an RNA sample comprising more than one RNA molecule species. Three independent ddPCR measurements on a sample comprising 4 different mRNAs (about 2 ng per mRNA species) were performed. A: Theoretically expected ratio of the four mRNA species; B-D: measured relative ratios of the mRNA species. A detailed description of the experiment is provided in Example 3.

To test the robustness of the system, three individual ddPCR experiments were performed on mixes that contained cDNAs at constant ratios (25:25:25:25) (FIG. 5).

3.3 Results

The results of FIG. 3 show that using ddPCR, each target cDNA of interest was specifically amplified within a mix of four different cDNA species using target specific primers. Furthermore, the absence of the target cDNA in the mixture led to a disappearance of the signal, indicating that the ddPCR setup was highly specific and that there were no off-target amplifications even though the mixture contained very similar non-target cDNA species.

FIG. 4 shows that the established assay for the analysis of RNA mixtures is highly sensitive and robust, because the step-wise increase (10% steps) of one target cDNA in the mixture could be precisely determined and the measured concentration for said cDNA species matched the expected concentration.

FIG. 5 shows that the established assay for the analysis of RNA mixtures is highly robust, because the variation between the three individual ddPCR experiments was negligible. The discrepancy of the obtained ratios (datasets B-D) to the expected 25:25:25:25 ratio (A) can be explained by inaccuracies introduced in the process of sample mRNA mixture preparation (manual pipetting of 2 ng of four different HA mRNAs).

Overall, the herein presented results show that dPCR is perfectly suited as robust, reliable, sensitive and reproducible quality control method for the analysis of RNA mixtures, particularity of pharmaceutical RNA mixtures.

Example 4: Testing of Different Annealing Temperatures for ddPCR

The results of the example show that the ddPCR reaction is very robust and provides reliable results over a broad range of annealing temperatures.

An RNA mixture comprising four different RNA species (obtained according to previous Example) was used as template to further evaluate the robustness of RT-ddPCR as a quality control. Reverse transcription and ddPCR was essentially performed as explained in the previous Examples.

Figure 6:
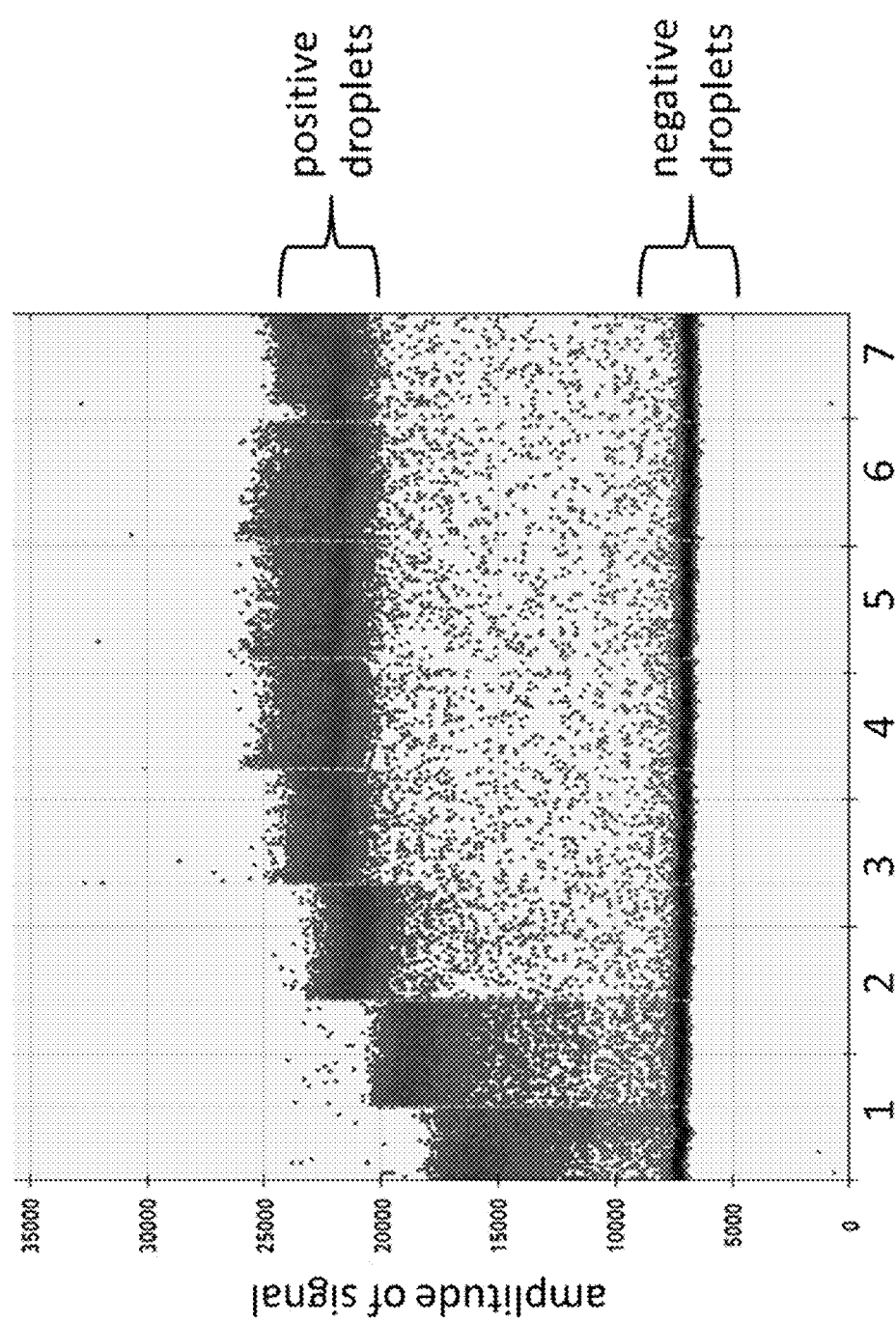
FIG. 6: ddPCR 1-D-plot of specificity testing of a representative primer pair at temperatures from 65 to 55° C. The annealing temperature of 61° C. is the highest temperature which leads to optimal separation of positive and negative population of droplets. 1: 65.0° C.; 2: 64.4° C.; 3: 63.1° C.; 4: 61.2° C.; 5: 59.0° C.; 6: 57.1° C.; 7: 55.8° C.; 8: 55° C. A detailed description of the experiment is provided in Example 4.

The results for one exemplary primer pair (see FIG. 6) show that the specific target sequence in the mixture of four different sequences was reliably and specifically detected over a broad primer annealing temperature range (1: 65.0° C.; 2: 64.4° C.; 3: 63.1° C.; 4: 61.2° C.; 5: 59.0° C.; 6: 57.1° C.; 7: 55.8° C.; 8: 55° C.).

The results show that the method is particularly suitable as a quality control in a regulated environment as robust and reliable results are obtained over a broad range of different primer annealing temperatures. This is particularly advantageous e.g. compared to qPCR where small differences in temperature conditions have a huge impact on the results.

Example 5: Testing of Specificity with Respect to Discrimination Between Target and Non-Target Sequences for EvaGreen Based ddPCR The results show that ddPCR reactions are very specific with very few non-target false positive results.

One of the most critical method parameters of PCR is specificity. Unspecific amplification leads to erroneous quantification of target template which is often the case for qPCR based methods.

An RNA mixture comprising four different RNA species, containing the target RNA, was used as a target mixture. An RNA mixture comprising three different RNA species, lacking the target RNA, was used as a non-target mixture. Reverse transcription and ddPCR was essentially performed as explained in examples above.

Figure 7:
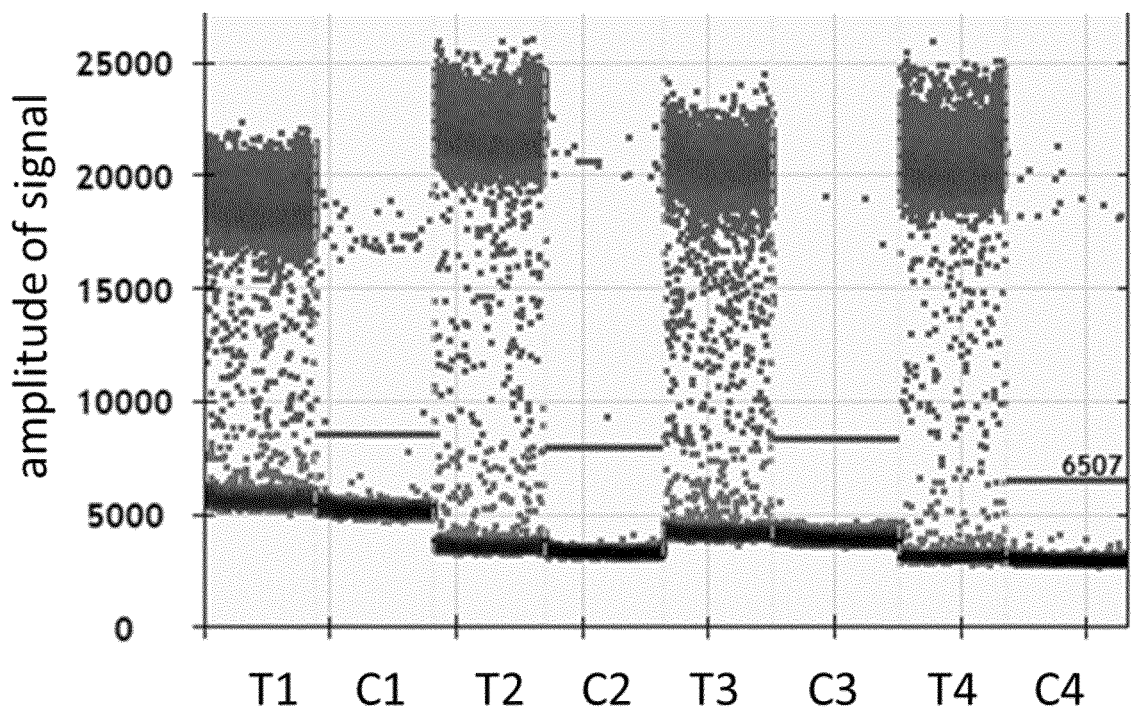
FIG. 7: ddPCR 1-D-plot of specificity testing of specific primer pairs on different mixtures comprising the target sequence (T1, T2, T3, T4) or lacking the target sequence (C1, C2, C3, C4) at target concentration of 500 cp/ul. A detailed description of the experiment is provided in Example 5.

The specificity of the method was tested in several experiments by comparing RT-ddPCR results for a specific primer set on mixtures comprising all four species (including the target; T1, T2, T3, T4 in FIG. 7) and control mixtures comprising only three species (lacking the target; C1, C2, C3, C4 in FIG. 7). The results of the experiment are shown in FIG. 7. The results show that the RT-ddPCR is specific, as a specific signal was detected only in the reaction comprising the target cDNA. This is particularly advantageous e.g. compared to RT-qPCR, where reactions on very similar sequences have a huge impact on the reliability, robustness and quality of the results.

Figure 8:
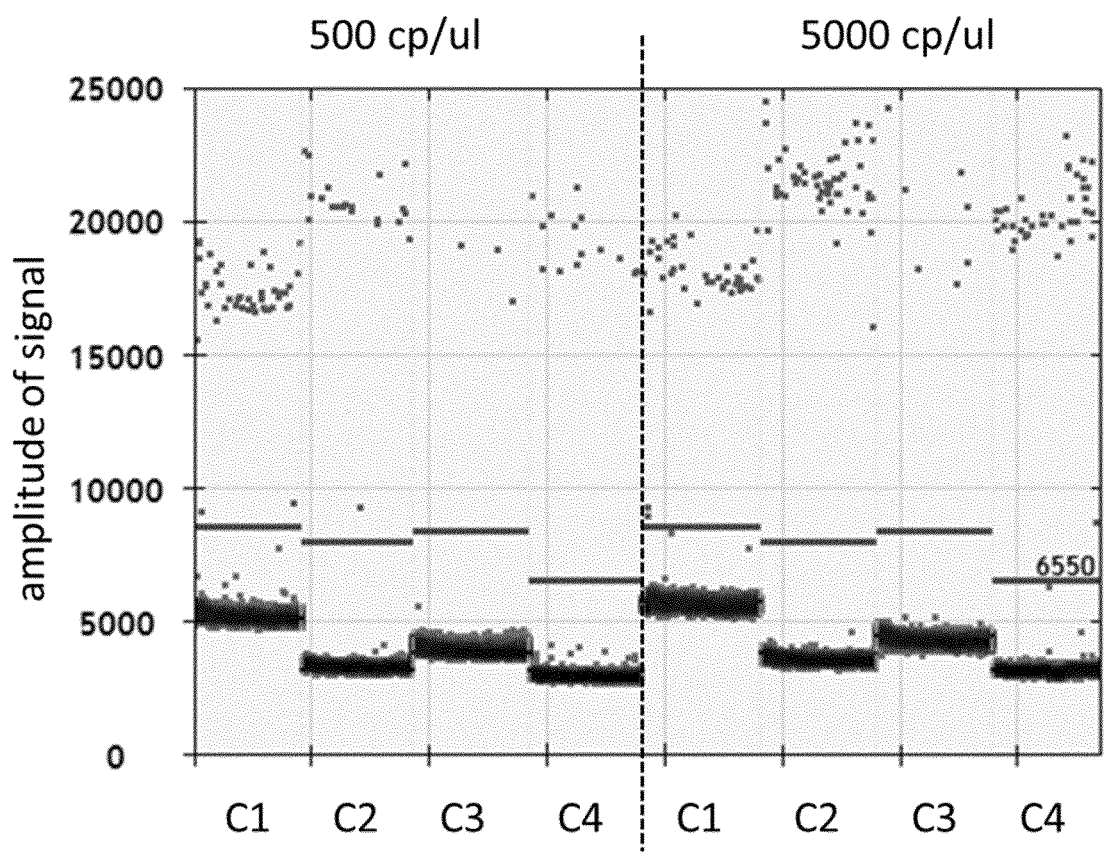
FIG. 8: ddPCR 1-D-plot of specificity testing of a specific primer pair on mixtures lacking the target sequence (C1, C2, C3, C4) to determine background positive reactions. Experiment was performed using different concentrations (500 cp/ul; 5000 cp/ul). A detailed description of the experiment is provided in Example 5.

To further determine background positive droplets, mixtures comprising three species (lacking the target) were tested at different cDNA concentrations (500 cp/µl and 5,000 cp/µl). The results are shown in FIG. 8. The results show that the RT-ddPCR method is highly specific as even with high non-target template concentrations (5,000 cp/µl) there were very few positive events detectable. This is particularly advantageous e.g. compared to RT-qPCR where reactions on very similar sequences have a huge impact on the reliability, robustness and quality of the results.

Example 6: Linearity of the RT-ddPCR Method

The results show that the ddPCR method is linear over a broad concentration range and provides reliable and robust results even when pipetting steps are performed by hand.

An RNA mixture comprising four different RNA species (obtained according to previous Example) was used as template to further evaluate the robustness of RT-ddPCR as quality control. Reverse transcription and ddPCR were essentially performed as explained in the previous Examples. Correlation of nominal vs. measured cp/µl of a target sequence at different intervals (10% (squares), 5% (diamonds) difference interval) pipetted by hand (without acoustic pipetting) was determined. The results are shown in FIG. 9.

Figure 9:
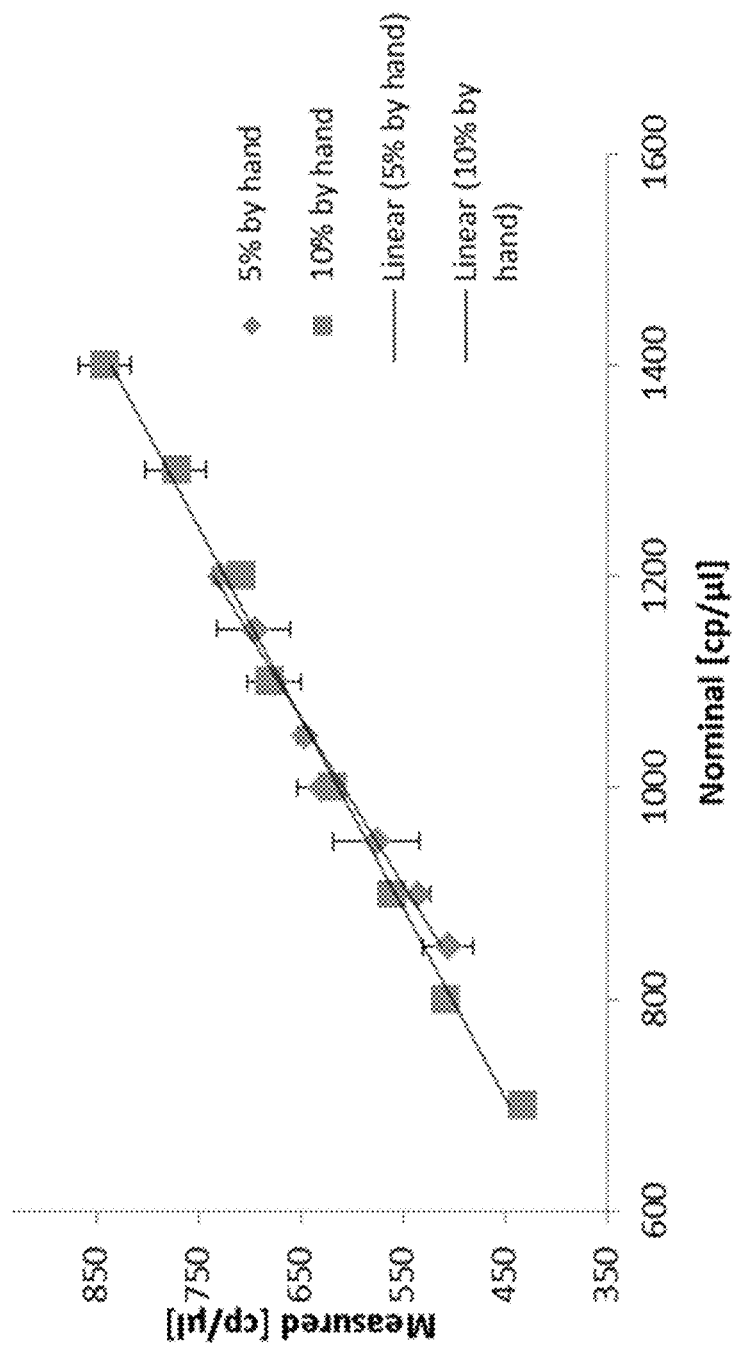
FIG. 9: Correlation of nominal and measured concentrations (cp/ul) of a representative construct at different intervals. A detailed description of the experiment is provided in Example 6.

As shown in FIG. 9, measured and nominal values correlate (indicated by the linearity of the results). The results show that RT-ddPCR provides reliable results in a broad range of concentrations.

Example 7: Testing Repeatability and Intermediate Precision of the RT-ddPCR Method Repeatability and intermediate precision are critical method parameters that define the acceptance criteria and suitability of the method as quality control. In order to test the precision of the method all 4 RNAs were mixed and the mixture was reverse transcribed before cDNA was aliquoted into 4 separate reactions which then were supplemented with the respective primers for the respective target (ddPCR performed as described above).

TABLE 5

Intermediate precision of the RT-ddPCR of Tetraflu RNA mixture for two template concentrations (A: 500 cp/µl upper table and B: 1,000 cp/µl lower table). The experiment has been performed on different days and by different analysts.

| | A | | | | |
|---|---|---|---|---|---|
| | Person 1 | Person 2 | CV inter person/500 cp/µl | | |
| RNA | 500 cp/µl | 500 cp/µl | Mean | Stdev | CV |
| T1 | 21.77% | 23.62% | 22.69% | 0.013 | 5.75% |
| T2 | 26.27% | 24.89% | 25.58% | 0.010 | 3.82% |
| T3 | 21.68% | 23.94% | 22.81% | 0.016 | 6.98% |
| T4 | 30.28% | 27.56% | 28.92% | 0.019 | 6.64% |

| | B | | | | |
|---|---|---|---|---|---|
| | Person 1 | Person 2 | CV inter person/1000 cp/µl | | |
| RNA | 1000 cp/µl | 1000 cp/µl | Mean | Stdev | CV |
| T1 | 23.84% | 22.94% | 23.39% | 0.006 | 2.72% |
| T2 | 23.39% | 25.66% | 24.52% | 0.016 | 6.53% |
| T3 | 25.64% | 23.63% | 24.63% | 0.014 | 5.78% |
| T4 | 27.13% | 27.78% | 27.45% | 0.005 | 1.67% |

TABLE 6

Repeatability experiment performed on different days by the same analyst starting with the same RNA mixture. RT A and RT B were performed by one analyst. The variation between RT reactions pipetted on two different days is 0.07% for T1, 1.86% for T2, 2.73% for T3 and 1.57% for T4.

| RNA | RTA | RTB | MEAN | STDEV | CV [%] |
|---|---|---|---|---|---|
| R5697 | 28.02% | 27.99% | 28.01% | 0.0002 | 0.07% |
| R5698 | 23.11% | 23.73% | 23.42% | 0.0044 | 1.86% |
| R4936 | 27.95% | 26.89% | 27.42% | 0.0075 | 2.73% |
| R5218 | 20.92% | 21.39% | 21.15% | 0.0033 | 1.57% |

As shown in Tables 10 and 11 the ddPCR method of the invention is particularly suitable for use as a quality control as variation in the obtained results is low.

Example 8: Influence of Lipid Components of LNPs on the Performance of the RT-ddPCR For the formulation of an RNA drug product, the RNA may be encapsulated using e.g. four different lipids that form lipid nanoparticles (LNPs) enabling a more efficient cellular uptake of the RNA. For the RNA analysis of LNPs, a separation method is used that involves solubilization of the lipid components using Triton-X-100 detergent and purification of RNA using magnetic beads (BE-005216). As relative content should also be determined for the drug product, the impact of Triton-X-100 and lipid components in different dilutions on the performance of the ddPCR was tested. This was done as risk mitigation for the case that, after purification, remnants of lipids and Triton-X-100 might be present in the purified RNA.

Figure 10:
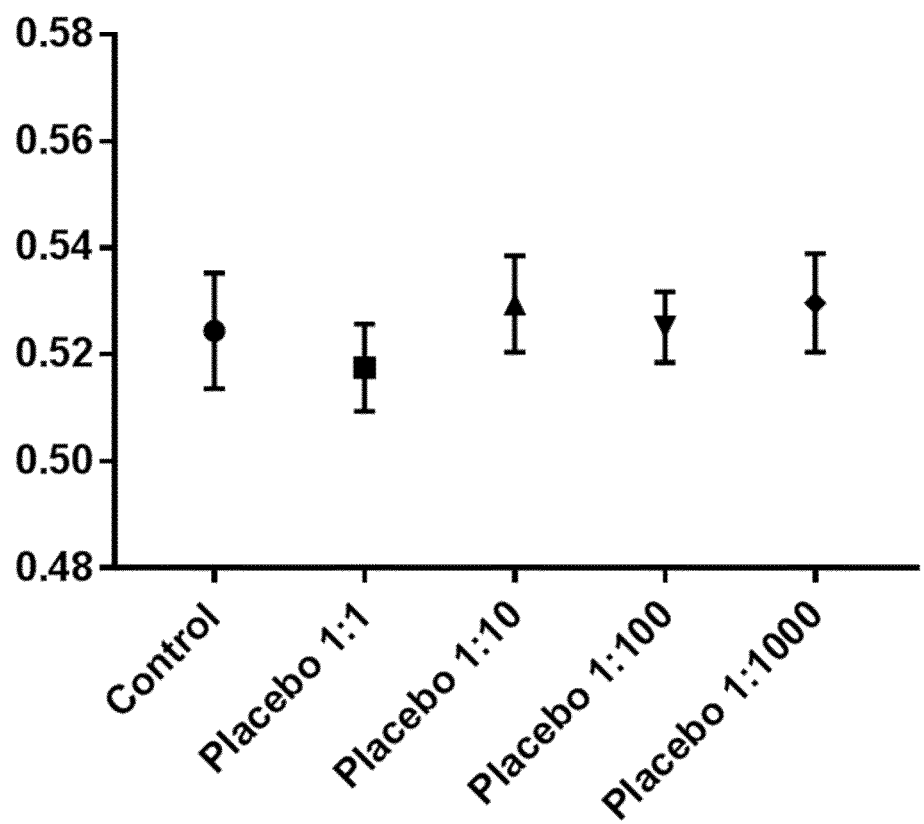
FIG. 10: shows that lipid components or detergent spiking has no impact on the precision of the RT-ddPCR method. A detailed description of the experiment is provided in Example 8.

Triton-X-100 and empty liposomes (placebo LNP) composed of 4 lipids were mixed at a concentration that is usually used for the separation of RNA from LNP. For this, 12 µl placebo stock was mixed with 88 µl water for injection and 20 µl 20% Triton-X-100 (⅕ of total volume) resulting in a concentration that corresponds to 100 ng/µl RNA in filled LNPs with the addition of Triton-X-100. This mixture was then serially diluted 1:10, 1:100, 1:1000 using WFI and 10 µl of each dilution was combined with the equal molar RNA mixture containing RNA at a constant total concentration of 10 ng/µl. The highest concentration of LNP/Triton-X-100 is thus simulating the first step of separation of LNP and RNA with the difference that all components are 10-fold diluted when combined (e.g. 10 ng/µl instead of 100 ng/µl for RNA). The serial dilution of the LNP/Triton-X-100 mimics the depletion during the separation of LNPs and RNAs. The mixture was then further diluted to obtain total amount of 2 ng total RNA for reverse transcription. The results are shown in FIG. 10 and Table 7.

TABLE 7

P values of multiple comparisons of control vs. the different dilutions of LNP (placebo)/Triton-X-100 spiked samples.

| Dunnett's multiple comparisons test using one way ANOVA | P value |
| --- | --- |
| Control vs. Placebo 1:1 | 0.8543 |
| Control vs. Placebo 1:10 | 0.9428 |
| Control vs. Placebo 1:100 | 0.9999 |
| Control vs. Placebo 1:1000 | 0.9004 |

Result:

Even in the presence of a high amount of lipids and Triton-X-100 there was no detectable impact on the precision/robustness of the ddPCR results. The results show that the ddPCR method is particularly suitable for the characterization of an LNP complexed RNA mixture (see e.g. Example 9).

Example 9: Characterization of an LNP Complexed RNA Mixture Using RT-ddPCR

The goal of this experiment is to analyze the content of lipid nanoparticles (LNP) in terms of presence and quantity that have been formulated with a mixture of different RNA molecule species, e.g. mRNA molecule species. This is an important quality control step for LNP-formulated mRNA mixtures.

9.1 Formulation of Different RNA Molecule Species Complexed in LNPs

A lipid nanoparticle (LNP)-complexed mRNA molecule species mixture is prepared using an ionizable amino lipid (cationic lipid), phospholipid, cholesterol and a PEGylated lipid. LNPs are prepared as follows. Cationic lipid, 1,2-distearoyl-sn-glycero-3-phosphocholine (DSPC), cholesterol and PEG-lipid are solubilized in ethanol. Briefly, the mRNA mixture is diluted to a total concentration of 0.05 mg/mL in 50 mM citrate buffer, pH 4. Syringe pumps are used to mix the ethanolic lipid solution with the mRNA mixture at a ratio of about 1:6 to 1:2 (vol/vol). The ethanol is then removed and the external buffer replaced with PBS by dialysis. Finally, the lipid nanoparticles are filtered through a 0.2 µm pore sterile filter. Lipid nanoparticle particle diameter size is determined by quasi-elastic light scattering using a Malvern Zetasizer Nano (Malvern Instruments Ltd, Malvern, UK).

9.2 Analysis of the LNP Formulated RNA Mixture:

A sample of LNP formulated RNA mixture is treated with detergent (about 2% Triton™ X100) to dissociate the LNPs. Optionally, released RNA is captured using Agencourt® AMPure® XP beads (Beckman Coulter, Brea, CA, USA) essentially according to the manufacturer's instructions. Following preparation of the RNA, cDNA is generated essentially as described in Example 3 followed by ddPCR analysis performed essentially as described in Examples 2 and 3.

9.3 Separation of LNPs Using PEG-FACS and Analysis of LNP Content Using RT-ddPCR A sample of LNPs is treated with ribonuclease RNaseA to degrade non-complexed RNA molecules which are bound onto the surface of the LNP or remain soluble in the LNP solution. After degradation of the RNA, RiboGreen® dye is added to confirm the completeness of the digest. The RNA-free LNP sample is treated with RNase inhibitor. The RNA free and RNase free LNP solution is then contacted with a primary PEG-antibody, followed by a secondary antibody labelled with a fluorescent probe. The LNP solution is subjected to FACS sorting to obtain single discrete LNPs. The LNPs are sorted into a PCR compatible multi well plate (one LNP per well). After detergent treatment of the LNP samples, complexed RNA molecules are released and a reverse transcription reaction is performed to obtain a cDNA molecule mixture. The cDNA molecule mixture is used to perform target specific ddPCR reactions (for each target with a different spectrometrically distinguishable intercalating dye). The ddPCR reactions are performed essentially as described in Examples 2 and 3. After ddPCR, the plate is placed into a multi-channel droplet reader to analyze the fluorescence signals of droplets. The copy number for each target cDNA molecule and presence per LNP are determined using QuantaSoft™ (BioRad Laboratories, Hercules, CA, USA).

In another setup, the RNA free and RNase free LNP solution is subjected to FACS sorting to obtain samples comprising 50 LNPs. The LNPs are sorted into a PCR compatible multi well plate (50 LNPs per well). After detergent treatment of the LNP samples, complexed RNA molecules are released and a reverse transcription reaction is performed to obtain a cDNA molecule mixture. The cDNA mixture is used to perform multiplexed ddPCR reactions (for each target a separate reaction with EvaGreen® as an intercalating dye). The ddPCR reactions are performed essentially as described in Example 2 and 3. After ddPCR, the plate is placed into a single-channel droplet reader to analyze the fluorescence signals of droplets. The copy number for each target cDNA species and thus of each RNA molecule species and presence per LNP are determined using QuantaSoft™ (BioRad, Laboratories, Hercules, CA, USA).

9.4 Separation of LNPs Using PEG-FACS and Analysis of LNP Content Using RT-qPCR

After separation of LNPs, detergent treatment of the LNP samples and RNA recovery as described above, RNA is released and a two-step RT-qPCR is performed. In a two-step RT-qPCR, cDNA synthesis and qPCR are performed in different reactions in separate reaction vessels. cDNA synthesis is performed using the obtained RNA. 1 µl random hexamer primers (0.2 µg/µl; Fermentas, Thermo Fisher Scientific, Waltham, MA, USA), 1 µl 10 mM dNTP mix and the respective volume of RNA is denatured in a total volume of 14 µl for 5 minutes at 65° C.cDNA synthesis is performed according to the SuperScript III reverse transcriptase manual (Invitrogen), subsequently. The obtained cDNA in a concentration range of 50 fg/µl to 5 ng/µl is used for RT-qPCR using SsoAdvanced™ Universal SYBR® Green Supermix (Bio-Rad Laboratories, Hercules, CA, USA) according to the manufacturer's protocol using respective sequence specific primers.

9.5 Separation of LNPs Using Acoustic Liquid Handler and Analysis of LNP Content Using RT-ddPCR RNA free and RNAse free LNP solution is obtained essentially according to Example 9.2. Separation of LNPs is performed using acoustic liquid transfer with a Labcyte Echo® 555 acoustic liquid transfer device onto the destination plate.

The LNP sample is diluted to a concentration of 1 LNP/volume unit. The diluted LNP solution is spotted on a target plate (1 volume unit per well). After detergent treatment of the single LNP samples, complexed RNA molecules are released and a reverse transcription reaction is performed to obtain a cDNA molecule mixture. The cDNA molecule mixture is used to perform ddPCR reactions. The ddPCR reactions, using multiple intercalating dyes, are performed essentially as described in Example 2.3. After ddPCR, the plate is placed into a multi-channel droplet reader to analyze the fluorescence signals of the droplets. The copy number for each target cDNA molecule species and thus of each RNA molecule species and presence per LNP are determined using QuantaSoft (BioRad, Laboratories, Hercules, CA, USA).

Alternatively, RT-qPCR is used to characterize the separated LNPs, essentially as described in Example 4.4.

Example 10: Characterization of a Protein-Polymer-Complexed RNA Molecule Species Mixture Using RT-ddPCR The goal of this experiment is to analyze the content of polymeric nanoparticles in terms of presence and quantity that have been complexed with a mixture of different mRNA molecule species. This is an important quality control step for nanoparticle-complexed mRNA molecule species mixtures.

10.1 Formulation of a Polyvalent HA Vaccine, Encapsulated in Polymeric Nanoparticles 20 mg peptide (CHHHHHHRRRRHHHHHHC-NH$_2$, SEQ ID NO: 45) TFA salt is dissolved in 2 ml borate buffer pH 8.5 and stirred at room temperature for approximately 18 hours. Then, 12.6 mg PEG-SH 5000 (Sunbright) dissolved in N-methylpyrrolidone is added to the peptide solution and filled up to 3 ml with borate buffer pH 8.5. After 18 hours incubation at room temperature, the reaction mixture is purified and concentrated by centricon procedure (MWCO 10 kDa), washed against water and lyophilized. After lyophilization, the lyophilizate is dissolved in ELGA water and the concentration is adjusted to 10 mg/ml. The obtained polyethylenglycol/peptide polymers (HO-PEG5000-S-(S-CHHHHHHRRRRHHHHHHC-S-)7-S-PEG5000-OH) are used for further formulation with the RNA molecule species mixture.

First, ringer lactate buffer and respective amounts of the obtained polymer are mixed to generate polymer carriers. Then, the final mRNA carrier system is assembled by mixing the mRNA molecule species mixture with respective amounts of polymer-lipid carrier. After 10 minutes incubation at room temperature, polymer-complexed mRNA particles are formed.

10.2 Separation of Nanoparticles Using PEG-FACS and Analysis Using RT-ddPCR

A sample of nanoparticles is treated with ribonucleases to degrade non-complexed RNA which is bound onto the surface of the nanoparticles or remains soluble in solution. As ribonuclease, RNase A, RNase T1, or RNase I is used. Alternatively, a combination of different ribonucleases is used. After degradation of the RNA, RiboGreen® dye is added to assess the completeness of the digest. RNA-free nanoparticle samples are treated with RNase inhibitor. The RNA free and RNase free nanoparticle solution is then subjected to a primary PEG-antibody, followed by a secondary fluorescently labelled antibody. The nanoparticle solution is subjected to FACS sorting to obtain single discrete nanoparticles. The nanoparticles are sorted into a PCR compatible multi well plate. After high salt treatment and/or heparin treatment of nanoparticles, complexed RNA is released and a reverse transcription reaction is performed to obtain a cDNA mixture. The cDNA mixture is used to perform ddPCR different target specific reactions (for each target with a different spectrometrically distinguishable intercalating dye). The ddPCR reactions are performed essentially as described in Example 2.3. After ddPCR, the plate is placed into a multi-channel droplet reader to analyze the fluorescence signals of droplets. The copy number for each target cDNA and presence per LNP are determined using QuantaSoft™ (BioRad, Laboratories, Hercules, CA, USA).

In another setup, the RNA free and RNase free nanoparticle solution is subjected to FACS sorting. The nanoparticles are sorted into a PCR compatible multi well plate (50 nanoparticles per well). After salt treatment of the nanoparticle samples, complexed RNA is released and a reverse transcription reaction is performed to obtain a cDNA molecule species mixture. The cDNA molecule species mixture is used to perform multiplexed ddPCR reactions (for each target a separate reaction with EvaGreen® as an intercalating dye). The ddPCR reactions are performed essentially as described in Example 2.3. After ddPCR, the plate is placed into a single-channel droplet reader to analyze the fluorescence signals of droplets. The copy number for each target cDNA and presence per nanoparticle are determined using QuantaSoft™ (BioRad, Laboratories, Hercules, CA, USA).

The invention claimed is:

1. A method for quality control analysis of an RNA sample comprising n different RNA molecule species using reverse transcription and a polymerase chain reaction (PCR) based assay, wherein each of the n different RNA molecule species comprises one or more coding RNA molecules of synthetic origin, wherein n is an integer in the range of 3 to 200, comprising the following steps:
   a) simultaneously reverse transcribing the one or more coding RNA molecules of at least one RNA molecule species of the n different RNA molecule species in a single reaction vessel, thereby providing a cDNA sample comprising at least one cDNA molecule species, wherein each cDNA molecule species corresponds to one of the at least one RNA molecule species,
   b) subjecting the cDNA sample to the PCR based assay, and
   c) determining the at least one quality parameter of the RNA sample,
wherein the PCR based assay is digital PCR (dPCR), and wherein the at least one quality parameter is selected from the group consisting of (i) quantity of the one or more coding RNA molecules of the at least one RNA molecule species, (ii) presence of the one or more coding RNA molecules of the at least one RNA molecule species, (iii) integrity of the one or more coding RNA molecules of the at least one RNA molecule species, and (iv) quantitative ratio between the one or more coding RNA molecules of at least two RNA molecule species.

2. The method according to claim 1, wherein the RNA sample is a pharmaceutical RNA sample and further comprises a pharmaceutically acceptable carrier.

3. The method according to claim 1, wherein the digital PCR is droplet digital PCR (ddPCR).

4. The method according to claim 1, wherein n is an integer of 3 to 100.

5. The method according to claim 1, wherein step b) comprises a step of
   b1) simultaneous analysis of all cDNA molecule species in a single reaction vessel, or,
   b2) simultaneous analysis of two or more cDNA molecule species in a single reaction vessel, or b3) analysis of each cDNA molecule species in a separate reaction vessel.

6. The method according to claim 1, wherein the PCR based assay employs a detectable label.

7. The method according to claim 1, wherein the PCR based assay employs a sequence specific detectable label.

8. The method according to claim 5, wherein in step b1) for each cDNA molecule species a different detectable label is used, or wherein in step b2) for each cDNA molecule species to be analyzed in a single reaction vessel a different detectable label is used.

9. The method according to claim 1, wherein the one or more coding RNA molecules are obtained by an in vitro method.

10. The method according to claim 9, wherein the in vitro method is in vitro transcription or chemical RNA synthesis.

11. The method according to claim 1, wherein prior to step a) the one or more coding RNA molecules are purified using a method selected from the group consisting of high-performance liquid chromatography (HPLC), tangential flow filtration, oligo d(T) purification, ion exchange chromatography, hydroxyapatite chromatography, core bead flow-through chromatography, and combinations thereof.

12. The method according to claim 1, wherein the one or more coding RNA molecules of each RNA molecule species encode a different amino acid sequence.

13. The method according to claim 1, wherein the one or more coding RNA molecules of each of the n different RNA molecule species encode for one of n different peptides.

14. The method according to claim 1, wherein the RNA sequences of the one or more coding RNA molecules of each of the n different RNA molecule species are at least 80% identical to each other.

15. The method according to claim 1, wherein the n different RNA molecule species are selected from a group consisting of n different RNA molecule species encoding n different proteins or peptides derived from different serotypes or strains of a pathogen, n different RNA molecule species encoding n different antigens from one pathogen, n different RNA molecule species encoding n different antigens from different pathogens, n different RNA molecule species encoding n different isoforms or variants of an antigen, preferably a cancer antigen, n different RNA molecule species encoding n different epitopes of an antigen, n different RNA molecule species encoding n different cancer specific and/or patient specific cancer antigens, n different RNA molecule species encoding n different antibodies or antibody chains, n different RNA molecule species encoding n different proteins of one or more metabolic pathways, n different RNA molecule species encoding for n different isoforms of a protein for molecular therapy, n different RNA molecule species encoding for n different therapeutically active RNA molecule species, and combinations thereof.

16. The method according to claim 1, wherein at least one of the one or more coding RNA molecules is present in complexed form with at least one carrier compound, thereby forming at least one RNA-carrier complex.

17. The method according to claim 16, wherein the at least one RNA-carrier complex comprises more than one of the one or more coding RNA molecules and/or comprises one or more coding RNA molecules of different RNA molecule species.

18. The method according to claim 16, wherein the at least one carrier compound is a member selected from the group consisting of peptides, polymers, carbohydrates, cholesterol, polyethylene glycol (PEG), lipids, phospholipids, PEGylated lipids, cationic and polycationic compounds, and combinations thereof.

19. The method according to claim 16, wherein the at least one RNA-carrier complex comprises a member selected from the group consisting of liposome, lipid nanoparticle (LNP), and PEGylated peptide-based polymer complex and mixtures thereof.

20. The method according to claim 1, wherein n is an integer in the range of 4 to 50.

21. The method according to claim 4, wherein the n different RNA molecule species encode n different proteins derived from different serotypes or strains of a pathogen.

22. The method according to claim 21, wherein the n different proteins comprise hemagglutinin (HA) antigens from influenza viruses.

23. The method according to claim 22, wherein the n different proteins comprise HA antigens from influenza A and B viruses.

24. The method according to claim 23, wherein n is 3.

25. The method according to claim 4, wherein the n different RNA molecule species differ from each other in length by no more than 5%.

26. The method according to claim 25, wherein n different RNA molecule species are at least 80% identical to each other.

27. The method according to claim 25, wherein prior to step a) the one or more coding RNA molecules are purified by tangential flow filtration.

28. The method according to claim 27, the RNA molecules are complexed with lipid nanoparticles (LNPs).

29. The method according to claim 27, the RNA molecules are mRNA molecules.

30. The method according to claim 27, wherein the n different RNA molecule species encode n different proteins derived from different serotypes or strains of a pathogen.

31. The method according to claim 30, wherein the n different proteins comprise hemagglutinin (HA) antigens from influenza viruses.

32. The method according to claim 31, wherein the n different proteins comprise HA antigens from influenza A and B viruses.

33. The method according to claim 32, wherein n is 3.

34. The method according to claim 27, wherein the digital PCR is droplet digital PCR (ddPCR).

* * * * *

UNITED STATES PATENT AND TRADEMARK OFFICE
CERTIFICATE OF CORRECTION

PATENT NO. : 12,297,489 B2
APPLICATION NO. : 16/614127
DATED : May 13, 2025
INVENTOR(S) : Heinz et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 910 days.

Signed and Sealed this
Sixteenth Day of September, 2025

Coke Morgan Stewart
*Acting Director of the United States Patent and Trademark Office*

SEQUENCE LISTING

<160> NUMBER OF SEQ ID NOS: 45

<210> SEQ ID NO 1
<211> LENGTH: 3955
<212> TYPE: DNA
<213> ORGANISM: artificial
<220> FEATURE:

<223> OTHER INFORMATION: Influenza A (California) pDNA

<400> SEQUENCE: 1

```
cagctgcatt aatgaatcgg ccaacgcgcg gggagaggcg gtttgcgtat tgggcgctct     60
tccgcttcct cgctcactga ctcgctgcgc tcggtcgttc ggctgcggcg agcggtatca    120
gctcactcaa aggcggtaat acggttatcc acagaatcag gggataacgc aggaaagaac    180
atgtgagcaa aaggccagca aaaggccagg aaccgtaaaa aggccgcgtt gctggcgttt    240
ttccataggc tccgcccccc tgacgagcat cacaaaaatc gacgctcaag tcagaggtgg    300
cgaaacccga caggactata aagataccag gcgtttcccc ctggaagctc cctcgtgcgc    360
tctcctgttc cgaccctgcc gcttaccgga tacctgtccg cctttctccc ttcgggaagc    420
gtggcgcttt ctcatagctc acgctgtagg tatctcagtt cggtgtaggt cgttcgctcc    480
aagctgggct gtgtgcacga accccccgtt cagcccgacc gctgcgcctt atccggtaac    540
tatcgtcttg agtccaaccc ggtaagacac gacttatcgc cactggcagc agccactggt    600
aacaggatta gcagagcgag gtatgtaggc ggtgctacag agttcttgaa gtggtggcct    660
aactacggct acactagaag aacagtattt ggtatctgcg ctctgctgaa gccagttacc    720
ttcggaaaaa gagttggtag ctcttgatcc ggcaaacaaa ccaccgctgg tagcggtggt    780
tttttgttt gcaagcagca gattacgcgc agaaaaaaag gatctcaaga agatcctttg    840
atcttttcta cggggtctga cgctcagtgg aacgaaaact cacgttaagg gattttggtc    900
atgagattat caaaaaggat cttcacctag atccttttaa attaaaaatg aagttttaaa    960
tcaatctaaa gtatatatga gtaaacttgg tctgacagtt accaatgctt aatcagtgag   1020
gcacctatct cagcgatctg tctatttcgt tcatccatag ttgcctgact ccccgtcgtg   1080
tagataacta cgatacggga gggcttacca tctggcccca gtgctgcaat gataccgcga   1140
gacccacgct caccggctcc agatttatca gcaataaacc agccagccgg aagggccgag   1200
cgcagaagtg gtcctgcaac tttatccgcc tccatccagt ctattaattg ttgccgggaa   1260
gctagagtaa gtagttcgcc agttaatagt ttgcgcaacg ttgttgccat tgctacaggc   1320
atcgtggtgt cacgctcgtc gtttggtatg gcttcattca gctccggttc ccaacgatca   1380
aggcgagtta catgatcccc catgttgtgc aaaaaagcgg ttagctcctt cggtcctccg   1440
atcgttgtca gaagtaagtt ggccgcagtg ttatcactca tggttatggc agcactgcat   1500
aattctctta ctgtcatgcc atccgtaaga tgcttttctg tgactggtga gtactcaacc   1560
aagtcattct gagaatagtg tatgcggcga ccgagttgct cttgcccggc gtcaatacgg   1620
gataataccg cgccacatag cagaacttta aaagtgctca tcattggaaa acgttcttcg   1680
gggcgaaaac tctcaaggat cttaccgctg ttgagatcca gttcgatgta acccactcgt   1740
gcacccaact gatcttcagc atcttttact ttcaccagcg tttctgggtg agcaaaaaca   1800
ggaaggcaaa atgccgcaaa aaagggaata agggcgacac ggaaatgttg aatactcata   1860
ctcttccttt ttcaatatta ttgaagcatt tatcagggtt attgtctcat gagcggatac   1920
atatttgaat gtatttagaa aaataaacaa ataggggttc cgcgcacatt tccccgaaaa   1980
gtgccacctg acgtctaata cgactcacta tagggagaaa gcttaccatg aaggccatcc   2040
tggtggtcct cctgtacacc ttcgccaccg cgaacgccga cacgctgtgc atcggctacc   2100
acgccaacaa cagcaccgac accgtggaca ccgtgctcga gaagaacgtc acggtgaccc   2160
actccgtgaa cctgctggag gacaagcaca acgggaagct ctgcaagctg cggggcgtcg   2220
ccccgctgca cctcgggaag tgcaacatcg ccggctggat cctggggaac ccggagtgcg   2280
```
agagcctgtc caccgcgagc tcctggagct acatcgtgga gaccccctcc agcgacaacg 2340
gcacgtgcta ccccggcgac ttcatcgact acgaggagct ccgcgagcag ctgtccagcg 2400
tgtccagctt cgagcggttc gagatcttcc ccaagacctc cagctggccg aaccacgact 2460
ccaacaaggg ggtcaccgcc gcctgccccc acgccggcgc gaagagcttc tacaagaacc 2520
tgatctggct cgtgaagaag gggaactcct accccaagct gagcaagtcc tacatcaacg 2580
acaagggcaa ggaggtgctg gtcctctggg ggatccacca ccccagcacc agcgccgacc 2640
agcagtccct gtaccagaac gccgacgcct acgtgttcgt gggcagctcc cgctacagca 2700
agaagttcaa gccggagatc gccatccggc ccaaggtccg cgaccaggag ggccgcatga 2760
actactactg gaccctggtg gagcccgggg acaagatcac cttcgaggcg accggcaacc 2820
tcgtggtccc ccggtacgcc ttcgccatgg agcgcaacgc cgggtccggc atcatcatca 2880
gcgacacgcc ggtgcacgac tgcaacacca cctgccagac ccccaagggc gccatcaaca 2940
cgtccctgcc cttccagaac atccacccca tcaccatcgg gaagtgcccg aagtacgtga 3000
agagcaccaa gctgcggctc gcgaccggcc tgcgcaacat cccctccatc cagagccggg 3060
ggctgttcgg cgccatcgcc gggttcatcg agggcggctg gacggggatg gtcgacggct 3120
ggtacgggta ccaccaccag aacgagcagg gcagcgggta cgccgccgac ctcaagtcca 3180
cgcagaacgc gatcgacgag atcaccaaca aggtgaacag cgtcatcgag aagatgaaca 3240
cccagttcac cgccgtgggc aaggagttca accacctgga gaagcggatc gagaacctga 3300
acaagaaggt cgacgacggc ttcctcgaca tctggacgta caacgccgag ctgctggtgc 3360
tcctggagaa cgagcgcacc ctggactacc acgactccaa cgtgaagaac ctctacgaga 3420
aggtccggag ccagctgaag aacaacgcca aggagatcgg gaacggctgc ttcgagttct 3480
accacaagtg cgacaacacc tgcatggagt ccgtgaagaa cgggacctac gactacccca 3540
agtacagcga ggaggccaag ctgaaccgcg aggagatcga cggcgtgaag ctcgagtcca 3600
cgcggatcta ccagatcctg gcgatctaca gcaccgtcgc cagctccctg gtgctcgtgg 3660
tcagcctggg ggccatctcc ttctggatgt gcagcaacgg ctccctgcag tgccgcatct 3720
gcatctgagg actagttata agactgacta gcccgatggg cctcccaacg ggccctcctc 3780
ccctccttgc accgagatta ataaaaaaaa aaaaaaaaaa aaaaaaaaaa aaaaaaaaaa 3840
aaaaaaaaaa aaaaaaaaaa aaaaaatgca tccccccccc cccccccccc cccccccccc 3900
ccaaaggctc ttttcagagc caccagaatt cggatactct agacatatgc ttaag 3955

<210> SEQ ID NO 2
<211> LENGTH: 4012
<212> TYPE: DNA
<213> ORGANISM: artificial
<220> FEATURE:
<223> OTHER INFORMATION: HA Influenza B (Brisbane) pDNA

<400> SEQUENCE: 2
cagctgcatt aatgaatcgg ccaacgcgcg gggagaggcg gtttgcgtat tgggcgctct 60
tccgcttcct cgctcactga ctcgctgcgc tcggtcgttc ggctgcggcg agcggtatca 120
gctcactcaa aggcggtaat acggttatcc acagaatcag gggataacgc aggaaagaac 180
atgtgagcaa aaggccagca aaaggccagg aaccgtaaaa aggccgcgtt gctggcgttt 240
ttccataggc tccgcccccc tgacgagcat cacaaaaatc gacgctcaag tcagaggtgg 300
cgaaacccga caggactata aagataccag gcgtttcccc ctggaagctc cctcgtgcgc 360

```
tctcctgttc cgaccctgcc gcttaccgga tacctgtccg cctttctccc ttcgggaagc    420
gtggcgcttt ctcatagctc acgctgtagg tatctcagtt cggtgtaggt cgttcgctcc    480
aagctgggct gtgtgcacga acccccgtt cagcccgacc gctgcgcctt atccggtaac    540
tatcgtcttg agtccaaccc ggtaagacac gacttatcgc cactggcagc agccactggt    600
aacaggatta gcagagcgag gtatgtaggc ggtgctacag agttcttgaa gtggtggcct    660
aactacggct acactagaag aacagtattt ggtatctgcg ctctgctgaa gccagttacc    720
ttcggaaaaa gagttggtag ctcttgatcc ggcaaacaaa ccaccgctgg tagcggtggt    780 tttttgttt gcaagcagca gattacgcgc agaaaaaaag gatctcaaga agatcctttg    840
atcttttcta cggggtctga cgctcagtgg aacgaaaact cacgttaagg gattttggtc    900
atgagattat caaaaaggat cttcacctag atccttttaa attaaaaatg aagttttaaa    960
tcaatctaaa gtatatatga gtaaacttgg tctgacagtt accaatgctt aatcagtgag   1020
gcacctatct cagcgatctg tctatttcgt tcatccatag ttgcctgact ccccgtcgtg   1080
tagataacta cgatacggga gggcttacca tctggcccca gtgctgcaat gataccgcga   1140
gacccacgct caccggctcc agatttatca gcaataaacc agccagccgg aagggccgag   1200
cgcagaagtg gtcctgcaac tttatccgcc tccatccagt ctattaattg ttgccgggaa   1260
gctagagtaa gtagttcgcc agttaatagt ttgcgcaacg ttgttgccat tgctacaggc   1320
atcgtggtgt cacgctcgtc gtttggtatg gcttcattca gctccggttc caacgatca   1380 aggcgagtta catgatcccc catgttgtgc aaaaaagcgg ttagctcctt cggtcctccg   1440
atcgttgtca gaagtaagtt ggccgcagtg ttatcactca tggttatggc agcactgcat   1500
aattctctta ctgtcatgcc atccgtaaga tgcttttctg tgactggtga gtactcaacc   1560
aagtcattct gagaatagtg tatgcggcga ccgagttgct cttgcccggc gtcaatacgg   1620
gataataccg cgccacatag cagaacttta aaagtgctca tcattggaaa acgttcttcg   1680
gggcgaaaac tctcaaggat cttaccgctg ttgagatcca gttcgatgta acccactcgt   1740
gcacccaact gatcttcagc atcttttact ttcaccagcg tttctgggtg agcaaaaaca   1800
ggaaggcaaa atgccgcaaa aaagggaata agggcgacac ggaaatgttg aatactcata   1860
ctcttccttt ttcaatatta ttgaagcatt tatcagggtt attgtctcat gagcggatac   1920
atatttgaat gtatttagaa aaataaacaa ataggggttc cgcgcacatt tccccgaaaa   1980
gtgccacctg acgtctaata cgactcacta tagggagaaa gcttaccatg aaggccatca   2040
tcgtgctgct catggtcgtg accagcaacg ccgaccggat ctgcaccggc atcacgtcca   2100
gcaactcccc gcacgtggtc aagaccgcga cccaggggga ggtgaacgtg accggcgtca   2160
tcccgctgac gaccaccccc accaagagcc acttcgccaa cctgaagggg acggagaccc   2220
gcggcaagct ctgccccaag tgcctgaact gcaccgacct ggacgtggcc ctcgggcggc   2280
ccaagtgcac cggcaagatc ccgtccgccc gcgtgagcat cctgcacgag gtccggcccg   2340
tgacgtccgg ctgcttcccc atcatgcacg accgcaccaa gatccggcag ctgcccaacc   2400
tcctgcgcgg gtacgagcac atccggctga gcacccacaa cgtgatcaac gccgagaacg   2460
cgccgggcgg gccctacaag atcggcacct ccggagctg ccccaacatc acgaacggca   2520
acggcttctt cgccaccatg gcctgggccg tccccaagaa cgacaagaac aagaccgcga   2580
ccaacccgct cacgatcgag gtgcccctac tctgcaccga gggggaggac cagatcaccg   2640 tgtgggctt ccactccgac aacgagaccc agatggccaa gctgtacggg gacagcaagc   2700
cccagaagtt cacgtccagc gccaacggcg tcaccaccca ctacgtgtcc cagatcggcg   2760
```

```
ggttccccaa ccagaccgag gacggcgggc tgccgcagag cggccgcatc gtggtcgact   2820
acatggtgca gaagtccggg aagacgggca ccatcaccta ccagcggggc atcctcctgc   2880
cccagaaggt gtggtgcgcc agcgggcgct ccaaggtcat caagggcagc ctgcccctca   2940
tcggggaggc cgactgcctg cacgagaagt acggcgggct gaacaagagc aagccctact   3000
acaccggcga gcacgcgaag gccatcggca actgcccgat ctgggtgaag acgcccctca   3060
agctggccaa cgggaccaag taccggcccc ccgccaagct gctcaaggag cgcggcttct   3120
tcggggccat cgcgggcttc ctggagggcg ggtgggaggg catgatcgcc gggtggcacg   3180
gctacacctc ccacggggcc cacggcgtgg ccgtcgccgc ggacctgaag agcacccagg   3240
aggccatcaa caagatcacg aagaacctca actccctgag cgagctggag gtgaagaacc   3300
tccagcggct gtccggcgcc atggacgagc tgcacaacga gatcctcgag ctggacgaga   3360
aggtcgacga cctgcgcgcc gacaccatca gctcccagat cgagctcgcc gtgctgctga   3420
gcaacgaggg gatcatcaac tccgaggacg agcacctcct ggcgctggag cggaagctca   3480
agaagatgct gggcccgagc gccgtggaga tcgggaacgg ctgcttcgag accaagcaca   3540
agtgcaacca gacctgcctg gaccgcatcg ccgccgggac cttcgacgcg ggcgagttct   3600
ccctccccac gttcgacagc ctgaacatca ccgccgcctc cctgaacgac gacggcctgg   3660
acaaccacac catcctcctg tactacagca ccgccgcctc cagcctggcg gtcacgctca   3720
tgatcgccat cttcgtggtg tacatggtct cccgggacaa cgtgagctgc tccatctgcc   3780
tgtgaggact agttataaga ctgactagcc cgatgggcct cccaacgggc cctcctcccc   3840
tccttgcacc gagattaata aaaaaaaaaa aaaaaaaaaa aaaaaaaaaa aaaaaaaaaa   3900
aaaaaaaaaa aaaaaaaaaa aaatgcatcc cccccccccc cccccccccc cccccccccca   3960 aaggctcttt tcagagccac cagaattcgg atactctaga catatgctta ag           4012
```

```
<210> SEQ ID NO 3
<211> LENGTH: 4009
<212> TYPE: DNA
<213> ORGANISM: artificial
<220> FEATURE:
<223> OTHER INFORMATION: HA Influenza B (Phuket) pDNA

<400> SEQUENCE: 3
cagctgcatt aatgaatcgg ccaacgcgcg gggagaggcg gtttgcgtat tgggcgctct     60
tccgcttcct cgctcactga ctcgctgcgc tcggtcgttc ggctgcggcg agcggtatca    120
gctcactcaa aggcggtaat acggttatcc acagaatcag gggataacgc aggaaagaac    180
atgtgagcaa aaggccagca aaaggccagg aaccgtaaaa aggccgcgtt gctggcgttt    240
ttccataggc tccgcccccc tgacgagcat cacaaaaatc gacgctcaag tcagaggtgg    300
cgaaacccga caggactata aagataccag gcgtttcccc ctggaagctc cctcgtgcgc    360
tctcctgttc cgaccctgcc gcttaccgga tacctgtccg cctttctccc ttcgggaagc    420
gtggcgcttt ctcatagctc acgctgtagg tatctcagtt cggtgtaggt cgttcgctcc    480
aagctgggct gtgtgcacga accccccgtt cagcccgacc gctgcgcctt atccggtaac    540
tatcgtcttg agtccaaccc ggtaagacac gacttatcgc cactggcagc agccactggt    600
aacaggatta gcagagcgag gtatgtaggc ggtgctacag agttcttgaa gtggtggcct    660
aactacggct acactagaag aacagtattt ggtatctgcg ctctgctgaa gccagttacc    720
ttcggaaaaa gagttggtag ctcttgatcc ggcaaacaaa ccaccgctgg tagcggtggt    780
```

```
tttttttgttt gcaagcagca gattacgcgc agaaaaaaag gatctcaaga agatcctttg    840
atcttttcta cggggtctga cgctcagtgg aacgaaaact cacgttaagg gattttggtc    900
atgagattat caaaaaggat cttcacctag atccttttaa attaaaaatg aagttttaaa    960
tcaatctaaa gtatatatga gtaaacttgg tctgacagtt accaatgctt aatcagtgag   1020
gcacctatct cagcgatctg tctatttcgt tcatccatag ttgcctgact ccccgtcgtg   1080
tagataacta cgatacggga gggcttacca tctggcccca gtgctgcaat gataccgcga   1140
gacccacgct caccggctcc agatttatca gcaataaacc agccagccgg aagggccgag   1200
cgcagaagtg gtcctgcaac tttatccgcc tccatccagt ctattaattg ttgccgggaa   1260
gctagagtaa gtagttcgcc agttaatagt ttgcgcaacg ttgttgccat tgctacaggc   1320
atcgtggtgt cacgctcgtc gtttggtatg gcttcattca gctccggttc caacgatca    1380 aggcgagtta catgatcccc catgttgtgc aaaaaagcgg ttagctcctt cggtcctccg   1440
atcgttgtca gaagtaagtt ggccgcagtg ttatcactca tggttatggc agcactgcat   1500
aattctctta ctgtcatgcc atccgtaaga tgcttttctg tgactggtga gtactcaacc   1560
aagtcattct gagaatagtg tatgcggcga ccgagttgct cttgcccggc gtcaatacgg   1620
gataataccg cgccacatag cagaacttta aaagtgctca tcattggaaa acgttcttcg   1680
gggcgaaaac tctcaaggat cttaccgctg ttgagatcca gttcgatgta acccactcgt   1740
gcacccaact gatcttcagc atcttttact ttcaccagcg tttctgggtg agcaaaaaca   1800
ggaaggcaaa atgccgcaaa aaagggaata agggcgacac ggaaatgttg aatactcata   1860
ctcttccttt ttcaatatta ttgaagcatt tatcagggtt attgtctcat gagcggatac   1920
atatttgaat gtatttagaa aaataaacaa ataggggttc cgcgcacatt tccccgaaaa   1980
gtgccacctg acgtctaata cgactcacta tagggagaaa gcttaccatg aaggccatca   2040
tcgtgctgct catggtcgtg accagcaacg ccgaccgcat ctgcaccggc atcacgtcca   2100
gcaactcccc gcacgtggtc aagaccgcga cccaggggga ggtgaacgtg accggcgtca   2160 tcccccctgac gaccaccccc accaagagct acttcgccaa cctgaagggg acgcggaccc   2220
gcggcaagct ctgcccccgac tgcctgaact gcaccgacct ggacgtggcc ctcgggcggc   2280
ccatgtgcgt gggcaccacg ccgtccgcca aggccagcat cctgcacgag gtccgccccg   2340
tgacctccgg ctgcttcccc atcatgcacg accggaccaa gatccgccag ctgcccaacc   2400
tcctgcgggg gtacgagaag atccgcctga gcacccagaa cgtgatcgac gcggagaagg   2460
ccccgggcgg gccctaccgg ctcggcacgt ccgggagctg ccccaacgcc acctccaaga   2520
tcggcttctt cgccaccatg gcgtgggccg tccccaagga caactacaag aacgccacca   2580
acccgctgac ggtggaggtg ccctacatct gcaccgaggg cgaggaccag atcaccgtct   2640
gggggttcca cagcgacaac aagacccaga tgaagtccct gtacggcgac agcaaccccc   2700
agaagttcac gtccagcgcc aacggggtga ccacccacta cgtgtcccag atcggcgact   2760
tccccgacca gaccgaggac ggcggggctcc cgcagagcgg ccgcatcgtc gtggactaca   2820
tgatgcagaa gccgggaaag acgggcacca tcgtgtacca gcgggcgtc ctgctgcccc   2880 agaaggtgtg gtgcgcctcc gggcgcagca aggtgatcaa gggcagcctc cccctgatcg   2940
gggaggcgga ctgcctgcac gaggagtacg gcgggctcaa caagtccaag ccgtactaca   3000
ccggcaagca cgccaaggcc atcgggaact gccccatctg ggtcaagacc ccgctgaagc   3060
tggccaacgg cacgaagtac cggccccggg ccaagctcct gaaggagcgc ggcttcttcg   3120 ggcgatcgc cggcttcctg gagggcgggt gggagggat gatcgccggc tggcacggct   3180
```

```
acaccagcca cggggcccac ggcgtggccg tcgcggccga cctcaagtcc acccaggagg   3240
ccatcaacaa gatcaccaag aacctgaaca gcctgtccga gctcgaggtg aagaacctgc   3300
agcggctgag cggggccatg gacgagctcc acaacgagat cctggagctg gacgagaagg   3360
tggacgacct ccgcgccgac acgatctcca gccagatcga gctggcggtc ctgctctcca   3420
acgagggcat catcaacagc gaggacgagc acctcctggc cctcgagcgg aagctgaaga   3480
agatgctggg cccctccgcc gtggacatcg ggaacggctg cttcgagacc aagcacaagt   3540
gcaaccagac ctgcctcgac cgcatcgccg cggggacctt caacgccggc gagttcagcc   3600
tgcccacctt cgactccctg aacatcacgg ccgccagcct gaacgacgac gggctcgaca   3660
accacaccat cctgctgtac tactccaccg ccgcgagctc cctcgccgtg accctgatgc   3720
tggccatctt catcgtctac atggtgagcc gggacaacgt gtcctgcagc atctgcctct   3780
gaggactagt tataagactg actagcccga tgggcctccc aacgggccct cctcccctcc   3840
ttgcaccgag attaataaaa aaaaaaaaaa aaaaaaaaaa aaaaaaaaaa aaaaaaaaaa   3900
aaaaaaaaaa aaaaaaaaaa tgcatccccc cccccccccc cccccccccc ccccccaaag   3960
gctcttttca gagccaccag aattcggata ctctagacat atgcttaag               4009
```

<210> SEQ ID NO 4
<211> LENGTH: 3955
<212> TYPE: DNA
<213> ORGANISM: artificial
<220> FEATURE:
<223> OTHER INFORMATION: HA Influenza A (Honkong)

<400> SEQUENCE: 4

```
cagctgcatt aatgaatcgg ccaacgcgcg gggagaggcg gtttgcgtat tgggcgctct     60
tccgcttcct cgctcactga ctcgctgcgc tcggtcgttc ggctgcggcg agcggtatca    120
gctcactcaa aggcggtaat acggttatcc acagaatcag gggataacgc aggaaagaac    180
atgtgagcaa aaggccagca aaaggccagg aaccgtaaaa aggccgcgtt gctggcgttt    240
ttccataggc tccgcccccc tgacgagcat cacaaaaatc gacgctcaag tcagaggtgg    300
cgaaacccga caggactata aagataccag gcgtttcccc ctggaagctc cctcgtgcgc    360
tctcctgttc cgaccctgcc gcttaccgga tacctgtccg cctttctccc ttcgggaagc    420
gtggcgcttt ctcatagctc acgctgtagg tatctcagtt cggtgtaggt cgttcgctcc    480
aagctgggct gtgtgcacga accccccgtt cagcccgacc gctgcgcctt atccggtaac    540
tatcgtcttg agtccaaccc ggtaagacac gacttatcgc cactggcagc agccactggt    600
aacaggatta gcagagcgag gtatgtaggc ggtgctacag agttcttgaa gtggtggcct    660
aactacggct acactagaag aacagtattt ggtatctgcg ctctgctgaa gccagttacc    720
ttcggaaaaa gagttggtag ctcttgatcc ggcaaacaaa ccaccgctgg tagcggtggt    780
tttttgttt gcaagcagca gattacgcgc agaaaaaaag gatctcaaga agatcctttg     840
atcttttcta cggggtctga cgctcagtgg aacgaaaact cacgttaagg gattttggtc    900
atgagattat caaaaaggat cttcacctag atccttttaa attaaaaatg aagttttaaa    960
tcaatctaaa gtatatatga gtaaacttgg tctgacagtt accaatgctt aatcagtgag   1020
gcacctatct cagcgatctg tctatttcgt tcatccatag ttgcctgact ccccgtcgtg   1080
tagataacta cgatacggga gggcttacca tctggcccca gtgctgcaat gataccgcga   1140
gacccacgct caccggctcc agatttatca gcaataaacc agccagccgg aagggccgag   1200
```

```
cgcagaagtg gtcctgcaac tttatccgcc tccatccagt ctattaattg ttgccgggaa      1260
gctagagtaa gtagttcgcc agttaatagt ttgcgcaacg ttgttgccat tgctacaggc      1320
atcgtggtgt cacgctcgtc gtttggtatg gcttcattca gctccggttc ccaacgatca      1380
aggcgagtta catgatcccc catgttgtgc aaaaaagcgg ttagctcctt cggtcctccg      1440
atcgttgtca gaagtaagtt ggccgcagtg ttatcactca tggttatggc agcactgcat      1500
aattctctta ctgtcatgcc atccgtaaga tgcttttctg tgactggtga gtactcaacc      1560
aagtcattct gagaatagtg tatgcggcga ccgagttgct cttgcccggc gtcaatacgg      1620
gataataccg cgccacatag cagaacttta aaagtgctca tcattggaaa acgttcttcg      1680
gggcgaaaac tctcaaggat cttaccgctg ttgagatcca gttcgatgta acccactcgt      1740
gcacccaact gatcttcagc atcttttact tcaccagcg tttctgggtg agcaaaaaca       1800
ggaaggcaaa atgccgcaaa aaagggaata agggcgacac ggaaatgttg aatactcata      1860
ctcttccttt ttcaatatta ttgaagcatt tatcagggtt attgtctcat gagcggatac      1920
atatttgaat gtatttagaa aaataaacaa ataggggttc cgcgcacatt tccccgaaaa      1980
gtgccacctg acgtctaata cgactcacta tagggagaaa gcttaccatg aagaccatca      2040
tcgccctgag ctacatcctc tgcctggtgt cgcccagaa gatccccggc aacgacaact       2100
ccaccgcgac gctgtgcctc gggcaccacg ccgtcccgaa cggcaccatc gtgaagacca      2160
tcaccaacga ccgcatcgag gtgacgaacg ccaccgagct ggtccagaac agctccatcg      2220 ggagatctg cgacagcccc caccagatcc tggacggcga gaactgcacc ctcatcgacg       2280
ccctgctggg ggaccccag tgcgacggct tccagaacaa gaagtgggac ctcttcgtgg       2340
agcggtccaa ggcctacagc aactgctacc cctacgacgt gccggactac cgtgtccctgc     2400 gcagcctggt cgcctccagc ggcacccctcg agttcaacaa cgagtccttc aactggacgg     2460
gggtgaccca gaacggcacc agctccgcct gcatccggcg cagctccagc tccttcttca     2520 gccgctgaa ctggctgacc cacctcaact acaagtaccc cgccctgaac gtgacgatgc       2580
ccaacaacga gcagttcgac aagctgtaca tctggggcgt ccaccacccc gggaccgaca      2640
aggaccagat cttcccgtac gcgcagtcca gcggggcgcat catcgtgagc accaagcggt    2700
cccagcaggc cgtgatcccc aacatcggca gccgcccccg gatccgcgac atcccgtccc    2760
ggatcagcat ctactggacc atcgtcaagc cgggcgacat cctcctgatc aactccacgg     2820
ggaacctgat cgccccgcgc ggctacttca agctccggag cgggaagtcc agcatcatgc    2880
gctccgacgc ccccatcggc aagtgcaaga gcgagtgcat cacccccaac ggctccatcc    2940
cgaacgacaa gcccttccag aacgtgaacc ggatcaccta cggggcctgc cccgctacg     3000 tgaagcacag caccctgaag ctggcgacgg gcatgcggaa cgtccccgag aagcagaccc     3060
gcgggatctt cggcgccatc gccgggttca tcgagaacgg ctgggagggc atggtggacg    3120
ggtggtacgg cttccggcac cagaactccg aggggcgcgg ccaggccgcc gacctcaaga    3180
gcacccaggc ggccatcgac cagatcaacg gaaagctgaa ccgcctgatc ggcaagacca    3240
acgagaagtt ccaccagatc gagaaggagt ctccgaggt ggagggccgc atccaggacc     3300 tcgaagta cgtcgaggac acgaagatcg acctgtggag ctacaacgcc gagctgctcg      3360
tggccctgga gaaccagcac accatcgacc tgaccgactc cgagatgaac aagctcttcg    3420
agaagaccaa gaagcagctg cgcgagaacg ccgaggacat ggggaacggc tgcttcaaga    3480 tctaccaca gtgcgacaac gcgtgcatcg ggagcatccg gaacggcacg tacgaccaca    3540
acgtgtaccg cgacgaggcc ctgaacaacc ggttccagat caaggggggtc gagctcaagt   3600
```

-continued

```
ccggctacaa ggactggatc ctgtggatca gcttcgccat cagctgcttc ctgctctgcg   3660
tggccctgct gggcttcatc atgtgggcct gccagaaggg gaacatccgc tgcaacatct   3720
gcatctgagg actagttata agactgacta gcccgatggg cctcccaacg ggccctcctc   3780
ccctccttgc accgagatta ataaaaaaaa aaaaaaaaaa aaaaaaaaaa aaaaaaaaaa   3840
aaaaaaaaaa aaaaaaaaaa aaaaaatgca tccccccccc cccccccccc cccccccccc   3900
ccaaaggctc ttttcagagc caccagaatt cggatactct agacatatgc ttaag        3955
```

```

<210> SEQ ID NO 5
<211> LENGTH: 1918
<212> TYPE: RNA
<213> ORGANISM: artificial
<220> FEATURE:
<223> OTHER INFORMATION: Influenza A (California) RNA

<400> SEQUENCE: 5
gggagaaagc uuaccaugaa ggccauccug gugguccucc uguacaccuu cgccaccgcg     60
aacgccgaca cgcugugcau cggcuaccac gccaacaaca gcaccgacac cguggacacc    120
gugcucgaga agaacgucac ggugacccac uccgugaacc ugcuggagga caagcacaac    180
gggaagcucu gcaagcugcg gggcgucgcc ccgcugcacc ucgggaagug caacaucgcc    240
ggcuggaucc uggggaaccc ggagugcgag agccugucca ccgcgagcuc cuggagcuac    300
aucguggaga cccccuccag cgacaacggc acgugcuacc ccggcgacuu caucgacuac    360
gaggagcucc gcgagcagcu guccagcgug uccagcuucg agcgguucga gaucuucccc    420
aagaccucca gcuggccgaa ccacgacucc aacaaggggg ucaccgccgc cugcccccac    480
gccggcgcga agagcuucua caagaaccug aucuggcucg ugaagaaggg gaacuccuac    540
cccaagcuga gcaaguccua caucaacgac aagggcaagg aggugcuggu ccucuggggg    600
auccaccacc ccagcaccag cgccgaccag caguccccugu accagaacgc cgacgccuac    660
guguucgugg gcagcucccg cuacagcaag aaguucaagc cggagaucgc cauccggccc    720
aagguccgcg accaggaggg ccgcaugaac uacuacugga cccuggugga gcccggggac    780
aagaucaccu ucgaggcgac cggcaaccuc guggucccccc gguacgccuu cgccauggag    840
cgcaacgccg gguccggcau caucaucagc gacacgccgg ugcacgacug caacaccacc    900
ugccagaccc ccaagggcgc caucaacacg ucccugcccu uccagaacau ccaccccauc    960
accaucggga agugcccgaa guacgugaag agcaccaagc ugcggcucgc gaccggccug   1020
cgcaacaucc ccuccaucca gagccggggg cuguucggcg ccaucgccgg guucaucgag   1080
ggcggcugga cggggauggu cgacggcugg uacggguacc accaccagaa cgagcagggc   1140
agcggguacg ccgccgaccu caaguccacg cagaacgcga ucgacgagau caccaacaag   1200
gugaacagcg ucaucgagaa gaugaacacc caguucaccg ccgugggcaa ggaguucaac   1260
caccuggaga agcggaucga gaaccugaac aagaaggucg acgacggcuu ccucgacauc   1320
uggacguaca acgccgagcu gcuggugcuc cuggagaacg agcgcacccu ggacuaccac   1380
gacuccaacg ugaagaaccu cuacgagaag guccggagcc agcugaagaa caacgccaag   1440
gagaucggga acggcugcuu cgaguucuac cacaagugcg acaacaccug cauggagucc   1500
gugaagaacg ggaccuacga cuaccccaag uacagcgagg aggccaagcu gaaccgcgag   1560
gagaucgacg gcgugaagcu cgaguccacg cggaucuacc agauccuggc gaucuacagc   1620
accgucgcca gcucccuggu gcucguggguc agccuggggg ccaucuccuu cuggaugugc   1680
```

| | |
|---|---:|
| agcaacggcu cccugcagug ccgcaucugc aucgaggac uaguuauaag acugacuagc | 1740 |
| ccgaugggcc ucccaacggg cccuccuccc cuccuugcac cgagauuaau aaaaaaaaaa | 1800 |
| aaaaaaaaaa aaaaaaaaaa aaaaaaaaaa aaaaaaaaaa aaaaaaaaaa aaaaugcauc | 1860 |
| ccccccccc ccccccccc ccccccccc aaaggcucuu uucagagcca ccagaauu | 1918 |

```
<210> SEQ ID NO 6
<211> LENGTH: 1975
<212> TYPE: RNA
<213> ORGANISM: artificial
<220> FEATURE:
<223> OTHER INFORMATION: InfluenzaB (Brisbane)RNA

<400> SEQUENCE: 6
```

| | |
|---|---:|
| gggagaaagc uuaccaugaa ggccaucauc gugcugcuca uggucgugac cagcaacgcc | 60 |
| gaccggaucu gcaccggcau cacguccagc aacuccccgc acguggucaa gaccgcgacc | 120 |
| caggggagg ugaacgugac cggcgucauc ccgcugacga ccaccccac caagagccac | 180 |
| uucgccaacc ugaaggggac ggagacccgc ggcaagcucu gccccaagug ccugaacugc | 240 |
| accgaccugg acguggcccu cgggcggccc aagugcaccg gcaagauccc guccgcccgc | 300 |
| gugagcaucc ugcacgaggu ccggcccgug acguccggcu gcuucccau caugcacgac | 360 |
| cgcaccaaga uccggcagcu gcccaaccuc cugcgcgggu acgagcacau ccggcugagc | 420 |
| acccacaacu gaucaacgc cgagaacgcg ccgggcgggc cuacaagau cggcaccucc | 480 |
| gggagcugcc ccaacaucac gaacggcaac ggcuucuucg ccaccauggc cugggccguc | 540 |
| cccaagaacac aagaacaa gaccgcgacc aacccgcuca cgaucgaggu gcccuacauc | 600 |
| ugcaccgagg ggaggacca gaucaccgug uggggcuucc acuccgacaa cgagacccag | 660 |
| auggccaagc uguacgggga cagcaagccc cagaaguuca cguccagcgc caacggcguc | 720 |
| accacccacu acguguccca gaucggcggg uuccccaacc agaccgagga cggcgggcug | 780 |
| ccgcagagcg ccgcaucgu ggucgacuac auggugcaga gucccgggaa gacgggcacc | 840 |
| aucaccuacc agcggggcau ccuccugccc cagaaggugu ggugcgccag cgggcgcucc | 900 |
| aaggucauca agggcagccu gccccucauc ggggaggccg acugccugca cgagaaguac | 960 |
| ggcgggcuga acaagagcaa gcccuacuac accggcgagc acgcgaaggc caucggcaac | 1020 |
| ugcccgaucu ggugaagac gccccucaag cuggccaacg ggaccaagua ccggcccccc | 1080 |
| gccaagcugc ucaaggagcg cggcuucuuc ggggccaucg cgggcuuccu ggagggcggg | 1140 |
| ugggagggca ugaucgccgg guggcacggc uacaccuccc acggggccca cggcguggcc | 1200 |
| gucgccgcgg accugaagag caccaggag gccaucaaca agaucacgaa gaaccucaac | 1260 |
| ucccugagcg agcuggaggu gaagaaccuc cagcggcugu ccggcgccau ggacgagcug | 1320 |
| cacaacgaga uccucgagcu ggacgagaag gucgacgacc ugcgcgccga caccaucagc | 1380 |
| ucccagaucg agcucgccgu gcugcugagc aacgagggga ucaucaacuc cgaggacgag | 1440 |
| caccuccugg cgcuggagcg gaagcucaag aagaugcugg gccgagcgc cguggagauc | 1500 |
| gggaacggcu gcuucgagac caagcacaag ugcaaccaga ccugccugga ccgcaucgcc | 1560 |
| gccgggaccu cgacgcggg cgaguucucc cuccccacgu cgacagccu gaacaucacc | 1620 |
| gccgccucc ugaacgacga cggccuggac aaccaccacca uccuccugua cuacagcacc | 1680 |
| gccgccucca gccugcggu cacgcucaug aucgccaucu cguggugua cauggucucc | 1740 |
| cgggacaacg ugagcugcuc caucugccug ugaggacuag uuauaagacu gacuagcccg | 1800 |
| auggccuucc caacgggccc uccucccuc cuugcaccga gauuaauaaa aaaaaaaaaa | 1860 | aaaaaaaaaa aaaaaaaaaa aaaaaaaaaa aaaaaaaaaa aaaaaaaaaa augcaucccc    1920 cccccccccc cccccccccc ccccccccaaa ggcucuuuuc agagccacca gaauu         1975

<210> SEQ ID NO 7
<211> LENGTH: 1972
<212> TYPE: RNA
<213> ORGANISM: artificial
<220> FEATURE:
<223> OTHER INFORMATION: InfluenzaB(Pukhet)RNA

<400> SEQUENCE: 7
gggagaaagc uuaccaugaa ggccaucauc gugcugcuca uggucgugac cagcaacgcc 60
gaccgcaucu gcaccggcau cacguccagc aacuccccgc acguggucaa gaccgcgacc 120
cagggggagg ugaacgugac cggcgucauc ccccugacga ccaccccac caagagcuac 180 uucgccaacc ugaaggggac gcggacccgc ggcaagcucu gccccgacug ccugaacugc 240
accgaccugg acguggcccu cgggcggccc augugcgugg gcaccacgcc guccgccaag 300
gccagcaucc ugcacgaggu ccgccccgug accuccggcu gcuuccccau caugcacgac 360
cggaccaaga uccgccagcu gcccaaccuc cugcgggggu acgagaagau ccgccugagc 420
acccagaacg ugaucgacgc ggagaaggcc ccgggcgggc ccuaccggcu cggcacgucc 480
gggagcugcc ccaacgccac cuccaagauc ggcuucuucg ccaccauggc gugggccguc 540
cccaaggaca acuacaagaa cgccaccaac ccgcugacgg uggaggugcc cuacaucugc 600
accgagggcg aggaccagau caccgucugg ggguuccaca gcgacaacaa gacccagaug 660
aagucccugu acggcgacag caaccccag aaguucacgu ccagcgccaa cggggugacc 720
acccacuacg ugucccagau cggcgacuuc cccgaccaga ccgaggacgg cgggcucccg 780
cagagcggcc gcaucgucgu ggacuacaug augcagaagc ccgggaagac gggcaccauc 840
guguaccagc ggggcguccu gcugccccag aaggugugguu gcgccuccgg gcgcagcaag 900
gugaucaagg gcagccuccc ccugaucggg gaggcggacu gccugcacga ggaguacggc 960
gggcucaaca aguccaagcc guacuacacc ggcaagcacg ccaaggccau cgggaacugc 1020
cccaucuggg ucaagacccc gcugaagcug gccaacggca cgaaguaccg gcccccggcc 1080
aagcuccuga aggagcgcgg cuucuucggg gcgaucgccg gcuuccugga gggcgggugg 1140
gaggggauga ucgccggcug gcacggcuac accagccacg gggcccacgg cguggccguc 1200
gcggccgacc ucaaguccac ccaggaggcc aucaacaaga ucaccaagaa ccugaacagc 1260
cuguccgagc ucgaggugaa gaaccugcag cggcugagcg gggccaugga cgagcuccac 1320
aacgagaucc uggagcugga cgagaaggug gacgaccucc gcgccgacac gaucuccagc 1380
cagaucgagc uggcgguccu gcucuccaac gagggcauca ucaacagcga ggacgagcac 1440
cuccuggccc ucgagcggaa gcugaagaag augcugggcc ccuccgccgu ggacaucggg 1500
aacggcugcu ucgagaccaa gcacaagugc aaccagaccu gccucgaccg caucgccgcg 1560
gggaccuuca acgccggcga guucagccug cccaccuucg acucccugaa caucacggcc 1620
gccagccuga acgacgacgg gcucgacaac cacaccaucc ugcuguacua cuccaccgcc 1680
gcgagcuccc ucgccgugac ccugaugcug gccaucuuca ucgucuacau ggugagccgg 1740
gacaacgugu ccugcagcau cugccucuga ggacuaguua uaagacugac uagcccgaug 1800
ggccucccaa cgggcccucc uccccuccuu gcaccgagau uaauaaaaaa aaaaaaaaaa 1860
aaaaaaaaaa aaaaaaaaaa aaaaaaaaaa aaaaaaaaaa aaaaaaaaug cauccccccc 1920
cccccccccc cccccccccc ccccaaaggc ucuuucaga gccaccagaa uu        1972

<210> SEQ ID NO 8
<211> LENGTH: 1918
<212> TYPE: RNA
<213> ORGANISM: artificial
<220> FEATURE:
<223> OTHER INFORMATION: Influenza A (Hongkong)RNA

<400> SEQUENCE: 8
gggagaaagc uuaccaugaa gaccaucauc gcccugagcu acauccucug ccugguguuc        60
gcccagaaga uccccggcaa cgacaacucc accgcgacgc ugugccucgg gcaccacgcc       120
gucccgaacg gcaccaucgu gaagaccauc accaacgacc gcaucgaggu gacgaacgcc       180
accgagcugg uccagaacag cuccaucggg gagaucugcg acagccccca ccagauccug       240
gacggcgaga acugcacccu caucgacgcc cugcgggggg accccagug cgacggcuuc         300
cagaacaaga agugggaccu cuucguggag cgguccaagg ccuacagcaa cugcuacccc       360
uacgacgugc cggacuacgc gucccugcgc agccuggucg ccuccagcgg cacccucgag       420
uucaacaacg aguccuucaa cuggacgggg gugacccaga acggcaccag uccgccugc         480
auccggcgca gcuccagcuc cuucuucagc cggcugaacu ggcugacccca ccuaacuac       540
aaguaccccg cccugaacgu gacgaugccc aacaacgagc aguucgacaa gcuguacauc       600
ugggggcguc caccccccgg gaccgacaag gaccagaucu cccguacgc gcaguccagc         660
gggcgcauca ucgugagcac caagcggucc cagcaggccg ugauccccaa caucggcagc       720
cgccccggga uccgcgacau cccgucccgg aucagcaucu acuggaccau cgucaagccg       780
ggcgacaucc uccugaucaa cuccacgggg aaccugaucg cccgcgcgg cuacuucaag       840
cuccggagcg ggaaguccag caucaugcgc uccgacgccc ccaucggcaa ugcaagagc         900
gagugcauca cccccaacgg cuccaucccg aacgacaagc ccuuccagaa cgugaaccgg       960
aucaccuacg gggccugccc ccgcuacgug aagcacagca cccugaagcu ggcgacgggc       1020
augcggaacg uccccgagaa gcagacccgc gggaucuucg gcgccaucgc cgggguucauc     1080
gagaacggcu gggagggcau gguggacggg ugguacggcu ccggcaccca gaaucccgag       1140
gggcgcggcc aggccgccga ccucaagagc acccaggcgg ccaucgacca gaucaacggg       1200
aagcugaacc ggcugaucgg caagaccaac gagaaguucc accagaucga gaaggaguuc       1260
uccgaggugg agggccgcau ccaggaccuc gagaaguacg ucgaggacac gaagaucgac       1320
cuguggagcu acaacgccga gcugcucgug gcccuggaga accagcacac caucgaccug       1380
accgacuccg agaugaacaa gcucuucgag aagaccaaga gcagcugcg cgagaacgcc       1440
gaggacaugg ggaacggcug cuucaagauc uaccacaagu gcgacaacgc gugcaucggg       1500
agcauccgga acggcacgua cgaccacaac guguaccgcg acgaggcccu gaacaaccgg       1560
uuccagauca gggggucga gcucaagucc ggcuacaagg acuggauccu guggaucagc       1620
uucgccauca gcugcuuccu gcucuacgug cccugcugg gcuucaucau guggccugc         1680
cagaagggga acauccgcug caacaucugc aucugaggac uaguuauaag acugacuagc       1740
ccgauggggcc uccaacggg cccuccuccc uccuugcac cgagauuaau aaaaaaaaaa       1800
aaaaaaaaaa aaaaaaaaaa aaaaaaaaaa aaaaaaaaaa aaaaaaaaaa aaaaugcauc       1860
cccccccccc cccccccccc cccccccccc aaaggcucuu ucagagcca ccagaauu         1918

<210> SEQ ID NO 9
<211> LENGTH: 19

```
<212> TYPE: DNA
<213> ORGANISM: artificial
<220> FEATURE:
<223> OTHER INFORMATION: fw brisbane

<400> SEQUENCE: 9
tcgccatctt cgtggtgta                                         19

<210> SEQ ID NO 10
<211> LENGTH: 22
<212> TYPE: DNA
<213> ORGANISM: artificial
<220> FEATURE:
<223> OTHER INFORMATION: rev brisbane

<400> SEQUENCE: 10
ccatcgggct agtcagtctt at                                     22

<210> SEQ ID NO 11
<211> LENGTH: 21
<212> TYPE: DNA
<213> ORGANISM: artificial
<220> FEATURE:
<223> OTHER INFORMATION: fw pukhet

<400> SEQUENCE: 11
caccatcctg ctgtactact c                                      21

<210> SEQ ID NO 12
<211> LENGTH: 22
<212> TYPE: DNA
<213> ORGANISM: artificial
<220> FEATURE:
<223> OTHER INFORMATION: rev pukhet

<400> SEQUENCE: 12
ccatcgggct agtcagtctt at                                     22

<210> SEQ ID NO 13
<211> LENGTH: 19
<212> TYPE: DNA
<213> ORGANISM: artificial
<220> FEATURE:
<223> OTHER INFORMATION: fw hongkong

<400> SEQUENCE: 13
ctgctgggct tcatcatgt                                         19

<210> SEQ ID NO 14
<211> LENGTH: 22
<212> TYPE: DNA
<213> ORGANISM: artificial
<220> FEATURE:
<223> OTHER INFORMATION: rev hongkong

<400> SEQUENCE: 14
ccatcgggct agtcagtctt at                                     22

<210> SEQ ID NO 15
<211> LENGTH: 22
<212> TYPE: DNA
<213> ORGANISM: artificial
<220> FEATURE:
<223> OTHER INFORMATION: fw california

<400> SEQUENCE: 15
```

```
ctaccagatc ctggcgatct ac                                          22
```

<210> SEQ ID NO 16
<211> LENGTH: 22
<212> TYPE: DNA
<213> ORGANISM: artificial
<220> FEATURE:
<223> OTHER INFORMATION: rev california

<400> SEQUENCE: 16

```
ccatcgggct agtcagtctt at                                          22
```

<210> SEQ ID NO 17
<211> LENGTH: 8
<212> TYPE: PRT
<213> ORGANISM: artificial
<220> FEATURE:
<223> OTHER INFORMATION: Cys-Pep

<400> SEQUENCE: 17

```
Cys Arg Arg Arg Arg Arg Arg Arg
1               5
```

<210> SEQ ID NO 18
<211> LENGTH: 9
<212> TYPE: PRT
<213> ORGANISM: artificial
<220> FEATURE:
<223> OTHER INFORMATION: Cys-Pep

<400> SEQUENCE: 18

```
Cys Arg Arg Arg Arg Arg Arg Arg Arg
1               5
```

<210> SEQ ID NO 19
<211> LENGTH: 10
<212> TYPE: PRT
<213> ORGANISM: artificial
<220> FEATURE:
<223> OTHER INFORMATION: Cys-Pep

<400> SEQUENCE: 19

```
Cys Arg Arg Arg Arg Arg Arg Arg Arg Arg
1               5                   10
```

<210> SEQ ID NO 20
<211> LENGTH: 11
<212> TYPE: PRT
<213> ORGANISM: artificial
<220> FEATURE:
<223> OTHER INFORMATION: Cys-pep

<400> SEQUENCE: 20

```
Cys Arg Arg Arg Arg Arg Arg Arg Arg Arg Arg
1               5                   10
```

<210> SEQ ID NO 21
<211> LENGTH: 12
<212> TYPE: PRT
<213> ORGANISM: artificial
<220> FEATURE:
<223> OTHER INFORMATION: Cys-pep

<400> SEQUENCE: 21

```
Cys Arg Arg Arg Arg Arg Arg Arg Arg Arg Arg Arg
1               5                   10
```

<210> SEQ ID NO 22
<211> LENGTH: 13
<212> TYPE: PRT
<213> ORGANISM: artificial
<220> FEATURE:
<223> OTHER INFORMATION: Cys-pep

<400> SEQUENCE: 22

Cys Arg Arg Arg Arg Arg Arg Arg Arg Arg Arg Arg Arg
1               5                   10

<210> SEQ ID NO 23
<211> LENGTH: 14
<212> TYPE: PRT
<213> ORGANISM: artificial
<220> FEATURE:
<223> OTHER INFORMATION: Cys-pep

<400> SEQUENCE: 23

Cys Arg Arg Arg Arg Arg Arg Arg Arg Arg Arg Arg Arg Arg
1               5                   10

<210> SEQ ID NO 24
<211> LENGTH: 15
<212> TYPE: PRT
<213> ORGANISM: artificial
<220> FEATURE:
<223> OTHER INFORMATION: Cys-pep

<400> SEQUENCE: 24

Cys Arg Arg Arg Arg Arg Arg Arg Arg Arg Arg Arg Arg Arg Arg
1               5                   10                  15

<210> SEQ ID NO 25
<211> LENGTH: 16
<212> TYPE: PRT
<213> ORGANISM: artificial
<220> FEATURE:
<223> OTHER INFORMATION: Cys-pep

<400> SEQUENCE: 25

Cys Arg Arg Arg Arg Arg Arg Arg Arg Arg Arg Arg Arg Arg Arg Arg
1               5                   10                  15

<210> SEQ ID NO 26
<211> LENGTH: 17
<212> TYPE: PRT
<213> ORGANISM: artificial
<220> FEATURE:
<223> OTHER INFORMATION: Cys-pep

<400> SEQUENCE: 26

Cys Arg Arg Arg Arg Arg Arg Arg Arg Arg Arg Arg Arg Arg Arg Arg
1               5                   10                  15

Arg

<210> SEQ ID NO 27
<211> LENGTH: 18
<212> TYPE: PRT
<213> ORGANISM: artificial
<220> FEATURE:
<223> OTHER INFORMATION: Cys-pep

<400> SEQUENCE: 27

Cys Arg Arg Arg Arg Arg Arg Arg Arg Arg Arg Arg Arg Arg Arg Arg
1               5                   10                  15

Arg Arg

<210> SEQ ID NO 28
<211> LENGTH: 19
<212> TYPE: PRT
<213> ORGANISM: artificial
<220> FEATURE:
<223> OTHER INFORMATION: Cys-pep

<400> SEQUENCE: 28

Cys Arg Arg Arg Arg Arg Arg Arg Arg Arg Arg Arg Arg Arg Arg Arg
1               5                   10                  15

Arg Arg Arg

<210> SEQ ID NO 29
<211> LENGTH: 20
<212> TYPE: PRT
<213> ORGANISM: artificial
<220> FEATURE:
<223> OTHER INFORMATION: Cys-pep

<400> SEQUENCE: 29

Cys Arg Arg Arg Arg Arg Arg Arg Arg Arg Arg Arg Arg Arg Arg Arg
1               5                   10                  15

Arg Arg Arg Arg
            20

<210> SEQ ID NO 30
<211> LENGTH: 21
<212> TYPE: PRT
<213> ORGANISM: artificial
<220> FEATURE:
<223> OTHER INFORMATION: Cys-pep

<400> SEQUENCE: 30

Cys Arg Arg Arg Arg Arg Arg Arg Arg Arg Arg Arg Arg Arg Arg Arg
1               5                   10                  15

Arg Arg Arg Arg Arg
            20

<210> SEQ ID NO 31
<211> LENGTH: 9
<212> TYPE: PRT
<213> ORGANISM: artificial
<220> FEATURE:
<223> OTHER INFORMATION: Cys-pep

<400> SEQUENCE: 31

Cys Arg Arg Arg Arg Arg Arg Arg Cys
1               5

<210> SEQ ID NO 32
<211> LENGTH: 10
<212> TYPE: PRT
<213> ORGANISM: artificial
<220> FEATURE:
<223> OTHER INFORMATION: Cys-pep

<400> SEQUENCE: 32

Cys Arg Arg Arg Arg Arg Arg Arg Arg Cys
1               5                   10

<210> SEQ ID NO 33
<211> LENGTH: 11

-continued

<212> TYPE: PRT
<213> ORGANISM: artificial
<220> FEATURE:
<223> OTHER INFORMATION: Cys-pep

<400> SEQUENCE: 33

Cys Arg Arg Arg Arg Arg Arg Arg Arg Cys
1               5                   10

<210> SEQ ID NO 34
<211> LENGTH: 12
<212> TYPE: PRT
<213> ORGANISM: artificial
<220> FEATURE:
<223> OTHER INFORMATION: Cys-pep

<400> SEQUENCE: 34

Cys Arg Arg Arg Arg Arg Arg Arg Arg Arg Cys
1               5                   10

<210> SEQ ID NO 35
<211> LENGTH: 13
<212> TYPE: PRT
<213> ORGANISM: artificial
<220> FEATURE:
<223> OTHER INFORMATION: Cys-pep

<400> SEQUENCE: 35

Cys Arg Arg Arg Arg Arg Arg Arg Arg Arg Arg Cys
1               5                   10

<210> SEQ ID NO 36
<211> LENGTH: 14
<212> TYPE: PRT
<213> ORGANISM: artificial
<220> FEATURE:
<223> OTHER INFORMATION: Cys-pep

<400> SEQUENCE: 36

Cys Arg Arg Arg Arg Arg Arg Arg Arg Arg Arg Arg Cys
1               5                   10

<210> SEQ ID NO 37
<211> LENGTH: 15
<212> TYPE: PRT
<213> ORGANISM: artificial
<220> FEATURE:
<223> OTHER INFORMATION: Cys-pep

<400> SEQUENCE: 37

Cys Arg Arg Arg Arg Arg Arg Arg Arg Arg Arg Arg Arg Cys
1               5                   10                  15

<210> SEQ ID NO 38
<211> LENGTH: 16
<212> TYPE: PRT
<213> ORGANISM: artificial
<220> FEATURE:
<223> OTHER INFORMATION: Cys-pep

<400> SEQUENCE: 38

Cys Arg Arg Arg Arg Arg Arg Arg Arg Arg Arg Arg Arg Arg Cys
1               5                   10                  15

<210> SEQ ID NO 39
<211> LENGTH: 17
<212> TYPE: PRT

```
<213> ORGANISM: artificial
<220> FEATURE:
<223> OTHER INFORMATION: Cys-pep

<400> SEQUENCE: 39

Cys Arg Arg Arg Arg Arg Arg Arg Arg Arg Arg Arg Arg Arg Arg
1               5                   10                  15

Cys

<210> SEQ ID NO 40
<211> LENGTH: 18
<212> TYPE: PRT
<213> ORGANISM: artificial
<220> FEATURE:
<223> OTHER INFORMATION: Cys-pep

<400> SEQUENCE: 40

Cys Arg Arg Arg Arg Arg Arg Arg Arg Arg Arg Arg Arg Arg Arg
1               5                   10                  15

Arg Cys

<210> SEQ ID NO 41
<211> LENGTH: 19
<212> TYPE: PRT
<213> ORGANISM: artificial
<220> FEATURE:
<223> OTHER INFORMATION: Cys-pep

<400> SEQUENCE: 41

Cys Arg Arg Arg Arg Arg Arg Arg Arg Arg Arg Arg Arg Arg Arg
1               5                   10                  15

Arg Arg Cys

<210> SEQ ID NO 42
<211> LENGTH: 20
<212> TYPE: PRT
<213> ORGANISM: artificial
<220> FEATURE:
<223> OTHER INFORMATION: Cys-pep

<400> SEQUENCE: 42

Cys Arg Arg Arg Arg Arg Arg Arg Arg Arg Arg Arg Arg Arg Arg
1               5                   10                  15

Arg Arg Arg Cys
            20

<210> SEQ ID NO 43
<211> LENGTH: 21
<212> TYPE: PRT
<213> ORGANISM: artificial
<220> FEATURE:
<223> OTHER INFORMATION: Cys-pep

<400> SEQUENCE: 43

Cys Arg Arg Arg Arg Arg Arg Arg Arg Arg Arg Arg Arg Arg Arg
1               5                   10                  15

Arg Arg Arg Arg Cys
            20

<210> SEQ ID NO 44
<211> LENGTH: 22
<212> TYPE: PRT
<213> ORGANISM: artificial
<220> FEATURE:
```

```
<223> OTHER INFORMATION: Cys-pep

<400> SEQUENCE: 44

Cys Arg Arg Arg Arg Arg Arg Arg Arg Arg Arg Arg Arg Arg Arg
1               5                   10                  15

Arg Arg Arg Arg Arg Cys
            20

<210> SEQ ID NO 45
<211> LENGTH: 18
<212> TYPE: PRT
<213> ORGANISM: artificial
<220> FEATURE:
<223> OTHER INFORMATION: Cys-pep

<400> SEQUENCE: 45

Cys His His His His His His Arg Arg Arg Arg His His His His His
1               5                   10                  15

His Cys
```